(12) United States Patent
Gross et al.

(10) Patent No.: US 6,872,813 B1
(45) Date of Patent: Mar. 29, 2005

(54) GENES CODING FOR TOMATO β-GALACTOSIDASE POLYPEPTIDES

(75) Inventors: Kenneth C. Gross, Ellicott City, MD (US); David L. Smith, Columbia, MD (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 09/701,868

(22) PCT Filed: Jun. 8, 1999

(86) PCT No.: PCT/US99/12697

§ 371 (c)(1),
(2), (4) Date: Dec. 5, 2000

(87) PCT Pub. No.: WO99/64564

PCT Pub. Date: Dec. 16, 1999

Related U.S. Application Data

(60) Provisional application No. 60/088,805, filed on Jun. 9, 1998.

(51) Int. Cl.[7] .......................... C12N 15/29; C12N 15/63; C12N 9/38

(52) U.S. Cl. ................ 536/23.6; 435/91.41; 435/320.1; 435/69.1; 424/93.1

(58) Field of Search .......................... 435/91.41, 320.1, 435/69.1, 419, 468; 424/93.1; 536/23.6; 800/278, 298

(56) References Cited

PUBLICATIONS

Ross et al, "Apple B–Galactosidase", 1994, Plant Physiol. vol. 106, pp. 521–528.*

* cited by examiner

*Primary Examiner*—Phuong T. Bui
*Assistant Examiner*—Cynthia Collins
(74) *Attorney, Agent, or Firm*—John D. Fado; Janelle S. Graeter

(57) ABSTRACT

Novel DNA sequences derived from a family of genes encoding β-galactosidases in tomato are disclosed. β-Galactosidase II has demonstrated enzyme activity in cell wall disassembly, leading to loss of tissue integrity and fruit softening. Modification of β-galactosidase II gene expression in plants transformed for expression in the antisense direction results in improvement of the quality of fruit texture and firmness.

10 Claims, 52 Drawing Sheets

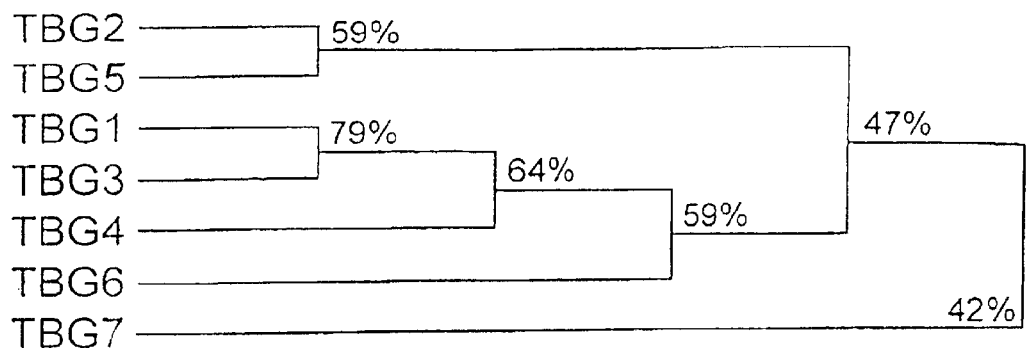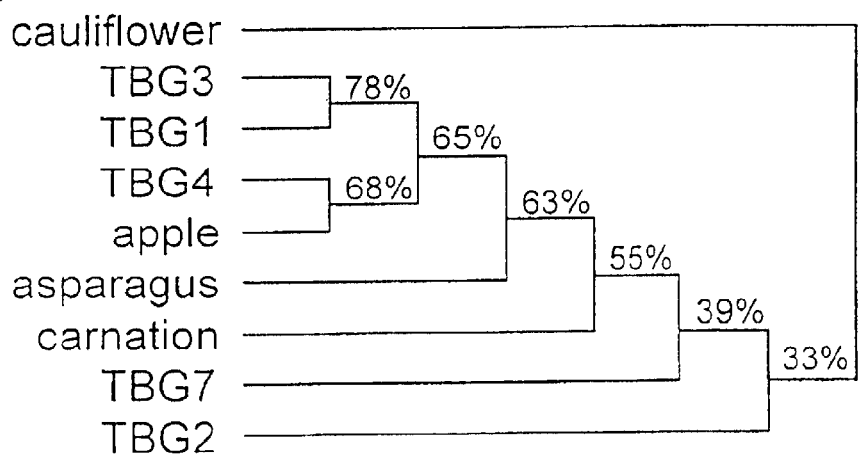
Figure 1. β-Galactosidase phylogenetic tree based on shared amino acid sequence identity. A. Tomato β-galactosidase (TBG) cDNAs. B. Plant β-galactosidases. Higgins-Sharp algorithm (UPGMA method)
FIG. 1

```
 31  AGCCTAGAAGAAGGAAAAAAGAAGTATGGACTAATGGAATAACATAAACATAAAAAGAGAAAAAAGAGAAAAATTCTTCAGACTAG          30
123  AAAACAGCTGTTTCCCTTCACTACTTTTTTTTTCCAATCTCTATATAATTGCAAGAATAAGTTTGCAACTTGATTAAAAAAAA          122
215  GAATAATAAGCTGTGGGGTAGGAGAAGTTAGTTCATTGCCTGTAAAGGCACAATCTTGATTCTTGATTGTTGACAAAT                 214
                                                                                                   305

306  ATG GGT TTT TGG ATG GCA ATG TTG CTG ATG TTA TTG TGT TGT GGA ATT GCT TCT                         374
  1  Met Gly Phe Trp Met Ala Met Leu Leu Met Leu Leu Cys Leu Trp Val Ser Cys Gly Ile Ala Ser         23

375  GTT TCA TAT GAC CAT AAA GCT ATC ATT GTA AAT GGA CAA AGA AAA ATT CTC GGA TCC ATT CAC             443
 24  Val Ser Tyr Asp His Lys Ala Ile Ile Val Asn Gly Gln Arg Lys Ile Leu Gly Ser Ile His             46

444  TAC CCT AGA AGC ACC CCT GAG ATG TGG CCA GAT CTT ATT CAG AAG GCA AAA GAA GGG GGA GTT GAT GTT     512
 47  Tyr Pro Arg Ser Thr Pro Glu Met Trp Pro Asp Leu Ile Gln Lys Ala Lys Glu Gly Gly Val Asp Val    69

513  ATA CAG ACT TAT GTT TTC TGG AAT GGG CAT GAG CCT GAA GAA GGG AAA TAT TTT GAA GAG TAT AGG         581
 70  Ile Gln Thr Tyr Val Phe Trp Asn Gly His Glu Pro Glu Glu Gly Lys Tyr Tyr Phe Glu Glu Tyr Arg    92

582  GAT TTA GTG AAG TTC ATT AAA GTG GTG CAA GAA GCA GGA CTT TAT GTG CAT CTT AGG ATT GGA CCT TAT    650
 93  Asp Leu Val Lys Phe Ile Lys Val Val Gln Glu Ala Gly Leu Tyr Val His Leu Arg Ile Gly Pro Tyr   115

651  GCA TGT GCT GAA TGG AAT TTT GGG GGT TTT CCT GTT TGG CTG AAG TAT GTT CCA GGT ATT AGT TTC AGA    719
116  Ala Cys Ala Glu Trp Asn Phe Gly Gly Phe Pro Val Trp Leu Lys Tyr Val Pro Gly Ile Ser Phe Arg   138

720  ACA AAC GAA GAG CCA TTC AAG ATG GCA ATG TTC ACT ACT AAG CAA TTC ACT ACT TTG GAT ATG ATG AAA GCA 788
139  Thr Asn Glu Glu Pro Phe Lys Met Ala Met Phe Thr Thr Lys Gln Phe Thr Thr Leu Asp Met Met Lys Ala 161

789  GAA AAG CTC TAT GAA ACT CAG GGT CCA ATT ATT CTA TCT CAG ATA ACA GAA AAT GAA TAT GGA CCT ATG    857
162  Glu Lys Leu Tyr Glu Thr Gln Gly Pro Ile Ile Leu Ser Gln Ile Thr Glu Asn Glu Tyr Gly Pro Met   184
```

FIG. 2A-1

| | | | | | | | | | | | |
|---|---|---|---|---|---|---|---|---|---|---|---|
| 858 | GAG | TGG | GAA | CTA | GGT | GAA | CCT | GGT | AAA | GTT | TAC | TCA | GAA | TGG | GCA | GCC | AAA | ATG | GCT | GTG | GAT | CTT | GGC | 926 |
| 185 | Glu | Trp | Glu | Leu | Gly | Glu | Pro | Gly | Lys | Val | Tyr | Ser | Glu | Trp | Ala | Ala | Lys | Met | Ala | Val | Asp | Leu | Gly | 207 |
| 927 | ACT | GGT | GTC | CCA | TGG | ATC | ATG | TGC | AAG | CAA | GAT | GAT | GTC | CCT | GAT | CCT | ATT | AAT | ACT | TGC | AAT | GGT | 995 |
| 208 | Thr | Gly | Val | Pro | Trp | Ile | Met | Cys | Lys | Gln | Asp | Asp | Val | Pro | Asp | Pro | Ile | Asn | Thr | Cys | Asn | Gly | 230 |
| 996 | TTC | TAC | TGT | GAC | TAC | TTC | ACA | CCA | AAT | AAG | GCT | AAT | AAA | CCC | AAG | ATG | TGG | ACT | GAA | GCC | TGG | ACA | GCC | 1064 |
| 231 | Phe | Tyr | Cys | Asp | Tyr | Phe | Thr | Pro | Asn | Lys | Ala | Asn | Lys | Pro | Lys | Met | Trp | Thr | Glu | Ala | Trp | Thr | Ala | 253 |
| 1065 | TGG | TTT | ACC | GAA | TTT | GGA | GGT | CCA | GTT | CCT | TAC | CGT | CCT | GCA | GAG | GAT | GCA | TTT | GCT | GTC | GCA | AGA | 1133 |
| 254 | Trp | Phe | Thr | Glu | Phe | Gly | Gly | Pro | Val | Pro | Tyr | Arg | Pro | Ala | Glu | Asp | Ala | Phe | Ala | Val | Ala | Arg | 276 |
| 1134 | TTT | ATA | CAA | ACG | GGA | GGC | TCC | TTC | ATC | AAT | TAC | TAT | CAT | ATG | TAT | GGA | GGA | ACA | TTT | GGA | AGG | ACT | 1202 |
| 277 | Phe | Ile | Gln | Thr | Gly | Gly | Ser | Phe | Ile | Asn | Tyr | Tyr | His | Met | Tyr | Gly | Gly | Thr | Phe | Gly | Arg | Thr | 299 |
| 1203 | TCT | GGT | GGC | CCA | TTT | ATT | GCT | ACT | AGT | GAT | TAT | GAT | GCA | CCC | CTA | GAT | GCA | CCC | TTT | GAA | TTT | GGG | TCA | TTA | CGG | 1271 |
| 300 | Ser | Gly | Gly | Pro | Phe | Ile | Ala | Thr | Ser | Asp | Tyr | Asp | Ala | Pro | Leu | Asp | Pro | Leu | Asp | Pro | Phe | Glu | Phe | Gly | Ser | Leu | Arg | 322 |
| 1272 | CAG | CCT | AAA | TGG | GGT | CAT | CTG | AAA | GAT | CTA | CAT | AGA | GCA | ATA | AAG | CTC | TGT | GAG | CCA | GCT | TTA | GTA | TCT | 1340 |
| 323 | Gln | Pro | Lys | Trp | Gly | His | Leu | Lys | Asp | Leu | His | Arg | Ala | Ile | Lys | Leu | Cys | Glu | Pro | Ala | Leu | Val | Ser | 345 |
| 1341 | GTA | GAT | CCA | ACT | GTG | ACA | TCC | TTA | GGA | AAC | TAT | CAA | GAG | CGT | GTT | TTC | AAG | TCA | GAG | TCT | GGG | GCC | 1409 |
| 346 | Val | Asp | Pro | Thr | Val | Thr | Ser | Leu | Gly | Asn | Tyr | Gln | Glu | Arg | Val | Phe | Lys | Ser | Glu | Ser | Gly | Ala | 368 |
| 1410 | TGC | GCT | GCC | TTC | CTA | GCA | AAT | TAC | AAC | CAG | CAC | TCT | TTT | GCT | AAA | GTG | GCA | TTT | GGG | AAC | ATG | CAT | TAT | 1478 |
| 369 | Cys | Ala | Ala | Phe | Leu | Ala | Asn | Tyr | Asn | Gln | His | Ser | Phe | Ala | Lys | Val | Ala | Phe | Gly | Asn | Met | His | Tyr | 391 |

FIG. 2A-2

```
1479  AAC TTG CCA CCC TGG TCT ATC AGC ATT CTT CCC GAC TGC AAG AAC ACT GTC TAT AAT ACT GCA AGG GTT  1547
 392  Asn Leu Pro Pro Trp Ser Ile Ser Ile Leu Pro Asp Cys Lys Asn Thr Val Try Asn Thr Ala Arg Val   414

1548  GGT GCT CAA AGT GCT CAG ATG AAG ATG ACT CCA GTC AGT AGA GGA TTC TCA TGG GAG TTC AAT GAA       1616
 415  Gly Ala Gln Ser Ala Gln Met Lys Met Thr Pro Val Ser Arg Gly Phe Ser Trp Glu Phe Asn Glu      437

1617  GAC GCA TCG CAT GAA GAC GAC ACT TTC ACA GTT GTT TTG GAG TTA TTG GAG CAG ATT AAT ATC ACA AGA  1685
 438  Asp Ala Ser His Glu Asp Asp Thr Phe Thr Val Val Leu Glu Leu Leu Glu Gln Ile Asn Ile Thr Arg  460

1686  GAT GTA TCT GAT TAC TTC TAT ATG TGG TTC ACT GAC ATT GAG ATT CCA ACA GAA GGA TTT TTG AAT AGT  1754
 461  Asp Val Ser Asp Tyr Phe Tyr Met Trp Phe Thr Asp Ile Glu Ile Pro Thr Glu Gly Phe Leu Asn Ser  483

1755  GGA AAT TGG CCT TGG CTT ACT GTC TTT TCT GCT GGC CAT GCA TTG CAT GTA TTC GTG AAT GGT CAA TTA  1823
 484  Gly Asn Trp Pro Trp Leu Thr Val Phe Ser Ala Gly His Ala Leu His Val Phe Val Asn Gly Gln Leu  506

1824  GCA GGA ACT GTG TAC GGA AGT TTA GAA AAC CTA AAA CCA GTT GGT CTT GGT ATA AAT TTC AGC AGA GCT  1892
 507  Ala Gly Thr Val Tyr Gly Ser Leu Glu Asn Leu Lys Pro Val Gly Leu Gly Ile Asn Phe Ser Arg Ala  529

1893  GGT GTG AAC AAG ATT TCT CTG CTA AGC ATT GCT GTT GGT CTT CCG AAC GTT GGC CCT CAT TTT GAG ACA  1961
 530  Gly Val Asn Lys Ile Ser Leu Leu Ser Ile Ala Val Gly Leu Pro Asn Val Gly Pro His Phe Glu Thr  552

1962  TGG AAT GCT GTT TCA GGA CCA GTT CTT AAT GGA CTT AAT GAA CTT AAT GGA CAT TTA ACA TGG           2030
 553  Trp Asn Ala Val Ser Gly Pro Val Leu Asn Gly Leu Asn Glu Leu Asn Gly His Leu Thr Trp          575

2031  CAG AAA TGG TTC TAC AAG GTT GGT CTA AAA GGA GAA GCC CTG CTT CAT TCA AGT GGT AGC CCA           2099
 576  Gln Lys Trp Phe Tyr Lys Val Gly Leu Lys Gly Glu Ala Leu Leu His Ser Ser Gly Ser Pro         598
```

FIG. 2A-3

```
2100 TCC GTG GAG TGG GTG GAA GGC TCT TTA GTG GCT CAG AAG CAG CTC CCA AGT TGG TAT AAG ACT ACA TTC 2168
599  Ser Val Glu Trp Val Glu Gly Ser Leu Val Ala Gln Lys Gln Leu Pro Ser Trp Tyr Lys Thr Thr Phe 621

2169 AAT GCT CCA GAT GGA AAT GAA CCT TTG GCT ATG GAT AAT ACC ATG GGC AAA GGT CAA GTA TGG ATA 2237
622  Asn Ala Pro Asp Gly Asn Glu Pro Leu Ala Met Asp Asn Thr Met Gly Lys Gly Gln Val Trp Ile 644

2238 AAT GGT CAG AGC CTC GGA CGC CAC TGG CCT GCA TAT CGC AAA TCA TCT GGA AGT TGT AGT GTC TGT AAC TAT 2306
645  Asn Gly Gln Ser Leu Gly Arg His Trp Pro Ala Tyr Arg Lys Ser Ser Gly Ser Cys Ser Val Cys Asn Tyr 667

2307 ACT GGT TTT GAT GAG AAA AAG TGC CTA ACT AAC TGT GGT GAG GGC TCA CAA AGA TGG CAC TAC CAC GTA 2375
668  Thr Gly Phe Asp Glu Lys Lys Cys Leu Thr Asn Cys Gly Glu Gly Ser Gln Arg Trp His Tyr His Val 690

2376 CCC CGG TCT TGG CTG TAT CCT ACT GGA AAT TTG TTA GTT TTA GTA TTC GAA GGA GGA GAT CCT TAT 2444
691  Pro Arg Ser Trp Leu Tyr Pro Thr Gly Asn Leu Leu Val Leu Val Phe Glu Gly Gly Asp Pro Tyr 713

2445 GGA ATC ACT TTA GTC AAA AGA GAA ATA TAT GCT GTT TGT GCT GAT ATA TAT GAG TGG CAA CCA CAG TTA 2513
714  Gly Ile Thr Leu Val Lys Arg Glu Ile Tyr Ala Val Cys Ala Asp Ile Tyr Glu Trp Gln Pro Gln Leu 736

2514 TTG AAT TGG CAG AGG CTA GTA TCT GGT AAG TTT GAC AGA CCT CTC AGA CCT AAA GCC CAT CTT AAG TGT 2582
737  Leu Asn Trp Gln Arg Leu Val Ser Gly Lys Phe Asp Arg Pro Leu Arg Pro Lys Ala His Leu Lys Cys 759

2583 GCA CCT GGT CAG CAG AAG TTT TCA ATC TCA AAA TTT GCA AGC TTT GGA ACA CCA GAG GTT TGT GGA GTT 2651
760  Ala Pro Gly Gln Gln Lys Phe Ser Ile Ser Lys Phe Ala Ser Phe Gly Thr Pro Glu Val Cys Gly Val 782

2652 TTC CAG CAG GGA AGC CAG TGC CAT CCG CGC TCA TAT GAT GCT TTC AAA AAG AAT TGT GTT GGG AAA GAG 2720
783  Phe Gln Gln Gly Ser Gln Cys His Pro Arg Ser Tyr Asp Ala Phe Lys Lys Asn Cys Val Gly Lys Glu 805
```

FIG. 2A-4

```
2721  TCT TGC TCA GTA CAG GTA ACA CCA GAG AAT TTT GGA GGT GAT CCA TGT CGA AAC GTT CTA AAG AAA CTC   2789
 806  Ser Cys Ser Val Gln Val Thr Pro Glu Asn Phe Gly Gly Asp Pro Cys Arg Asn Val Leu Lys Lys Leu    828

2790  TCA GTG GAA GCC ATT TGT AGT TGA TGATTCTGAGTATACAAGTGAAAAAAATACTGAACCACTCATATAAACATTTTCAAACG     2873
 829  Ser Val Glu Ala Ile Cys Ser ***                                                                836

2874  AGCTACTAGACATCCATTAACCCACTACCATTTTTTGGCTTTGCTGGGGTTGAAGTTGTACAGTTAAGCAACACACCTCTTTGATCAAAG      2965
2966  CTCACCTGATTATGAAGATGATTGTTGTTCTGTACATGTAAGGTTCGTCTAATTACACATTACAGATATGATTCTTGATGAATCGAT        3057
3058  GTGCAAATTTGTTTGTGTTAGGGTGAGAGAGACTTGAAAAGCATTTGCTTTCATGATGTTCTACATTATACAATCATATAATGTAAGTAAGC   3149
3150  AAGCAATAATTCATTGCTTTGCACATTGAAAAATGCATTTTACTATGTTGCAGTACAAAAAAAAAAAAAAAAAAA                    3224
```

3  AGC AGA AAA ACA CTG AAT TTT CCG TTA ATA CTA ACG GTG TTA ACT ATC CAC TTT GTG ATC GTC GCC  71
  1  Ser Arg Lys Thr Leu Asn Phe Pro Leu Ile Leu Thr Val Leu Thr Ile His Phe Val Ile Val Ala  23

72  GGC GAG TAT TTC AAG CCG TTC AAT GTC ACC TAC GAT AAC CGA GCT CTC ATC GGC GGT GGG AAA CGC CGT  140
 24  Gly Glu Tyr Phe Lys Pro Phe Asn Val Thr Tyr Asp Asn Arg Ala Leu Ile Gly Gly Gly Lys Arg Arg  46

141  ATG CTT ATC TCC GCC GGA ATT CAC TAC CCT CGC GCC ACT CCT GAG ATG TGG CCC ACA TTG ATA GCT AGG  209
 47  Met Leu Ile Ser Ala Gly Ile His Tyr Pro Arg Ala Thr Pro Glu Met Trp Pro Thr Leu Ile Ala Arg  69

210  AGC AAA GAA GGT GGT GCA GAT GTC ATC GAG ACT TAT ACA TTT TGG AAT GGT CAT GAG CCA ACC AGG GGA  278
 70  Ser Lys Glu Gly Gly Ala Asp Val Ile Glu Thr Tyr Thr Phe Trp Asn Gly His Glu Pro Thr Arg Gly  92

279  CAG TAC AAT TTT GAA GGA AGA TAT GAT ATT GTC AAG TTC GCA AAG CTA GTC GGA TCT CAT GGA CTG TTC  347
 93  Gln Tyr Asn Phe Glu Gly Arg Tyr Asp Ile Val Lys Phe Ala Lys Leu Val Gly Ser His Gly Leu Phe  115
```

FIG. 2B-1

```
348  CTC TTT ATT CGA ATA GGT CCT TAT GCC TGT GCA GAA TGG AAC TTC GGG GGA TTC CCC ATA TGG CTT CGT  416
116  Leu Phe Ile Arg Ile Gly Pro Tyr Ala Cys Ala Glu Trp Asn Phe Gly Gly Phe Pro Ile Trp Leu Arg  138

417  GAT ATA CCT GGA ATA GAA TTT CGA TTC ACA GAT AAT GCA CCA TTC AAG GAG ATG GAG CGC TAT GTT AAA  485
139  Asp Ile Pro Gly Ile Glu Phe Arg Thr Asp Asn Ala Pro Phe Lys Glu Met Glu Arg Tyr Val Lys  161

486  AAG ATA GTT GAT CTT ATG TCT GAG TCG CTC TTT TCG CAA GGT CCT ATC ATT TTG CTG CAG  554
162  Lys Ile Val Asp Leu Met Ile Ser Glu Ser Leu Phe Ser Gln Gly Pro Ile Ile Leu Leu Gln  184

555  ATT GAA AAT GAA TAT GGA AAT GTT GAA AGC TCA TTC GGT CCC AAG GGG AAG TTA TAT ATG AAA TGG GCT  623
185  Ile Glu Asn Glu Tyr Gly Asn Val Glu Ser Ser Phe Gly Pro Lys Gly Lys Leu Tyr Met Lys Trp Ala  207

624  GCT GAA ATG GCT GTT CTT GGT GCT GGT GTT CCA GTC ATG TGC AGG CAA ACT GAT GCT CCA GAA  692
208  Ala Glu Met Ala Val Leu Gly Ala Gly Val Pro Val Met Cys Arg Gln Thr Asp Ala Pro Glu  230

693  TAC ATC ATA GAT ACT TGT AAT GCA TAT TGT TAT TGT GAT GGG TTC ACG CCG AAT TCC GAG AAG AAA CCG AAA  761
231  Tyr Ile Ile Asp Thr Cys Asn Ala Tyr Tyr Cys Asp Gly Phe Thr Pro Asn Ser Glu Lys Lys Pro Lys  253

762  ATT TGG ACT GAG AAT TGG AAT GGA TGG TTT GCA GAT TGG GGT GAA AGA CTT CCA TAT AGA CCT TCC GAG  830
254  Ile Trp Thr Glu Asn Trp Asn Gly Trp Phe Ala Asp Trp Gly Glu Arg Leu Pro Tyr Arg Pro Ser Glu  276

831  GAT ATT GCA TTT CAA ATT GCT CGT TTC CAA TTT CAG GGC GGC AGC TTA CAG AAC TAT TAT TAT ATG TAT TTT  899
277  Asp Ile Ala Phe Gln Ile Ala Arg Phe Gln Phe Gln Gly Gly Ser Leu Gln Asn Tyr Tyr Met Tyr Phe  299

900  GGT GGG ACA AAT TTT GGC CGG GCT GGT CCA ACT CAA ATC ACT AGC TAT GAT TAT GAT GCT CCA  968
300  Gly Gly Thr Asn Phe Gly Arg Ala Gly Pro Thr Gln Ile Thr Ser Tyr Asp Tyr Asp Ala Pro  322
```

FIG. 2B-2

| | | | | | | | | | | |
|---|---|---|---|---|---|---|---|---|---|---|
| 969 | CTG | GAT | GAA | TAT | GGA | CTA | CTA | CGT | CAA | CCT | AAA | TGG | GGC | CAT | TTG | AAG | GAT | CTG | CAT | GCT | GCT | ATA | AAG | 1037 |
| 323 | Leu | Asp | Glu | Tyr | Gly | Leu | Leu | Arg | Gln | Pro | Lys | Trp | Gly | His | Leu | Lys | Asp | Leu | His | Ala | Ala | Ile | Lys | 345 |
| 1038 | CTT | TGT | GAA | CCA | GCT | CTT | GTT | GCT | GCT | CTT | GAT | TCA | CCT | CAG | TAT | ATT | AAA | CTG | GGA | CCA | AAA | CAG | GAG | GCA | 1106 |
| 346 | Leu | Cys | Glu | Pro | Ala | Leu | Val | Ala | Ala | Leu | Asp | Ser | Pro | Gln | Tyr | Ile | Lys | Leu | Gly | Pro | Lys | Gln | Glu | Ala | 345 |
| 1107 | CAT | GTC | TAT | CGT | GGA | ACA | TCC | CAA | TAT | ATG | TCC | TTA | AAT | GAA | GGC | ATA | GGT | ATC | TGC | GCA | GCA | 1175 |
| 369 | His | Val | Tyr | Arg | Gly | Thr | Ser | Gln | Tyr | Met | Ser | Leu | Asn | Glu | Gly | Ile | Cys | Ala | Ala | 391 |
| 1176 | TTT | ATT | GCA | AAT | ATT | GAT | ATT | GAT | AAT | ATC | GAC | CAT | GAA | TCA | GCA | ACA | GTG | AAA | TTT | TAC | CAA | GAG | TTC | ACT | TTA | CCT | 1244 |
| 392 | Phe | Ile | Ala | Asn | Ile | Asp | His | Glu | Ser | Ala | Thr | Val | Lys | Phe | Tyr | Gln | Glu | Phe | Thr | Leu | Pro | 414 |
| 1245 | CCA | TGG | TCA | GTG | GTA | TTC | TGC | CAG | ATT | GCA | GAA | CAG | CTT | TCA | ACA | CAG | CTA | AGG | TGG | GGG | CAC | AAA | 1313 |
| 415 | Pro | Trp | Ser | Val | Val | Phe | Cys | Gln | Ile | Ala | Glu | Gln | Leu | Ser | Thr | Gln | Leu | Arg | Trp | Gly | His | Lys | 437 |
| 1314 | CTT | CAA | TCA | AAA | CAG | AGC | TCG | CAG | ATT | CTG | TTT | CAG | ATA | ATT | CTT | TGT | TTC | TAC | AAG | TTA | TCA | 1382 |
| 438 | Leu | Gln | Ser | Lys | Gln | Ser | Ser | Gln | Ile | Leu | Phe | Gln | Ile | Ile | Leu | Cys | Phe | Tyr | Lys | Leu | Ser | 460 |
| 1383 | CTA | AAA | GCA | AGC | TCG | GAA | AGT | TTT | TCA | ATG | ACA | TCT | TGG | ATG | ACA | TTG | AAG | GAG | CCA | CTT | GGT | GTG | TGG | GGT | 1451 |
| 461 | Leu | Lys | Ala | Ser | Ser | Glu | Ser | Phe | Ser | Met | Thr | Ser | Trp | Met | Thr | Leu | Lys | Glu | Pro | Leu | Gly | Val | Trp | Gly | 483 |
| 1452 | GAC | AAG | AAT | TTC | ACT | TCT | AAA | GGA | CAT | CTG | GAG | ATA | TTG | AAT | GTG | ACA | AAA | GAC | CAG | TCT | GAT | TAC | CTG | 1520 |
| 484 | Asp | Lys | Asn | Phe | Thr | Ser | Lys | Gly | His | Leu | Glu | Ile | Leu | Asn | Val | Thr | Lys | Asp | Gln | Ser | Asp | Tyr | Leu | 506 |
| 1521 | TGG | TAT | CTG | ACC | AGG | ATA | TAT | ATT | TCT | GAT | GAT | GAC | ATC | TCA | TTT | TGG | GAG | GAA | AAT | GAT | GTT | AGT | CCA | 1589 |
| 507 | Trp | Tyr | Leu | Thr | Arg | Ile | Tyr | Ile | Ser | Asp | Asp | Asp | Ile | Ser | Phe | Trp | Glu | Glu | Asn | Asp | Val | Ser | Pro | 529 |

FIG. 2B-3

```
1590 ACA ATT GAT AGC ATG CGT GAT TTT GTT CGC ATT TTT GTT AAT GGG CAG CTT GCA GGT AGT GTG  1658
 530 Thr Ile Asp Ser Met Arg Asp Phe Val Arg Ile Phe Val Asn Gly Gln Leu Ala Gly Ser Val   552

1659 AAA GGC ATC AAG TGG GTG GTT CAA CCT GTT AAG CTG GTT CAG TAC AAC GAC ATA CTG CTA TTA  1727
 553 Lys Gly Ile Lys Trp Val Val Gln Pro Val Lys Leu Val Gln Tyr Asn Asp Ile Leu Leu Leu   575

1728 TCT GAG ACG GTG GGA TTG CAG AAT TAT GGT GCC TTC TTG GAG AAG GAT GGG GCA GGT TTT AAA GGT CAG  1796
 576 Ser Glu Thr Val Gly Leu Gln Asn Tyr Gly Ala Phe Leu Glu Lys Asp Gly Ala Gly Phe Lys Gly Gln   598

1797 ATA AAG CTT ACA GGA TGC AAA AGC GGG GAT ATC AAT CTC ACA ACA TCT TTA TGG ACC TAC CAG GTG GGG  1865
 599 Ile Lys Leu Thr Gly Cys Lys Ser Gly Asp Ile Asn Leu Thr Thr Ser Leu Trp Thr Tyr Gln Val Gly   621

1866 CTT AGA GGC GAA TTC CTG GAA GTA TAT GAT GTC AAT AGT ACT GAA GCA GGA TGG CCA CCA ACT GAG TTT CCC  1934
 622 Leu Arg Gly Glu Phe Leu Glu Val Tyr Asp Val Asn Ser Thr Glu Ala Gly Trp Pro Pro Thr Glu Phe Pro   644

1935 ACT GGT ACA ACT CCG TCA GTC TTT TCG TGG TAC AAG ACA AAG TTT GAT GCC CCA GGC GGG ACA GAT CCA  2003
 645 Thr Gly Thr Thr Pro Ser Val Phe Ser Trp Tyr Lys Thr Lys Phe Asp Ala Pro Gly Gly Thr Asp Pro   667

2004 GTT GCT CTT GAT TTT AGT AGC ATG GGA AAA GGT CAG GCA TGG GTT AAT GGC CAC CAT GTA GGA AGA TAT  2072
 668 Val Ala Leu Asp Phe Ser Ser Met Gly Lys Gly Gln Ala Trp Val Asn Gly His His Val Gly Arg Tyr   690

2073 TGG ACT TTG GTT GCA CCA CCA AAT GGA TGT TGT GGA AGA ACT GAT TAT CGT GGT GCT TAC CAC TCT GAT  2141
 691 Trp Thr Leu Val Ala Pro Pro Asn Gly Cys Cys Gly Arg Thr Asp Tyr Arg Gly Ala Tyr His Ser Asp   713

2142 AAA TGT AGG ACA AAC TGT CAG GAG ATT ACT CAG TAC CAT CAT ATA CCT ATA TCA TGG CTA AAG ACA  2210
 714 Lys Cys Arg Thr Asn Cys Gln Glu Ile Thr Gln Tyr His His Ile Pro Ile Ser Trp Leu Lys Thr   736
```

FIG. 2B-4

```
2211 TTA AAT AAT GTA CTA GTT ATC TTT GAA GAA ACA GAT AAA ACT CCG TTT GAT ATT TCC ATT TCT ACG CGT  2279
 737 Leu Asn Asn Val Leu Val Ile Phe Glu Glu Thr Asp Lys Thr Pro Phe Asp Ile Ser Ile Ser Thr Arg   759

2280 TCT ACT GAA ACC ATT TGT GCT CAA GTA TCG GAA AAG CAC TAT CCA CCT CTA CAT AAG TGG TCT CAT TCG  2348
 760 Ser Thr Glu Thr Ile Cys Ala Gln Val Ser Glu Lys His Tyr Pro Pro Leu His Lys Trp Ser His Ser   782

2349 GAG TTT GAC AGA AAG TTG TCT ATG GAT AAA ACA GAA CCA CAC TTG CAG TGT GAC GAA GGA CAT           2417
 783 Glu Phe Asp Arg Lys Leu Ser Met Asp Lys Thr Glu Pro His Leu Gln Cys Asp Glu Gly His           805

2418 ACA ATC TCT ATT GAA TTT GCA AGC TAT GGA AGT CCG AAT GGC AGC TGT CAA AAG TTC TCA CAA GGA       2486
 806 Thr Ile Ser Ile Glu Phe Ala Ser Tyr Gly Ser Pro Asn Gly Ser Cys Gln Lys Phe Ser Gln Gly       828

2487 AAA TGC CAT GCT GCA AAT AGC TTG TCT GTT GTA TCT CAG GCT TGT ATA GGA AGA ACT TGC AGT ATT       2555
 829 Lys Cys His Ala Ala Asn Ser Leu Ser Val Val Ser Gln Ala Cys Ile Gly Arg Thr Cys Ser Ile       851

2556 GGC ATT TCC AAT GGT GTA TTT GGA GAT CCA TGT CGA CAC GTT GTG AAG AGT TTG GCT GTT CAA GCA AAA   2624
 852 Gly Ile Ser Asn Gly Val Phe Gly Asp Pro Cys Arg His Val Val Lys Ser Leu Ala Val Gln Ala Lys   874

2625 TGC TCA CCA CCA CCA GAC CTC AGC ACT TCA GCT TCC TCG TGA GGAGACTCGTGTAACACGTTAACCTTTTAGAACGAA  2702
 875 Cys Ser Pro Pro Pro Asp Leu Ser Thr Ser Ala Ser Ser ***                                       888

2703 ACGATCCCTAAAGTCCACTCGTTCCCTGCCCCCGAGCCCTCTGCTACATTTCTCAGATGCCATCGTTACAATCAGGCGGAGAAAACGTAC   2794
2795 ATGGACGATTTTACTTGTAAATATTTGGTTACTGTATATAAAATGAATAAGTGCTATGCATATGAGCTGCAAATTATATGACAA         2886
2887 AGTAACAAATGAAAATAGAAAACTCCTGCTGTCAAAGAATTTAACAACACCATTTATTAAAGTTAGTTAACATGATTAACATGATTAAAAAAAAAAAAAA 2978
2979 AAAAAA                                                                                        2984
```

```
                                                                      AGAGTTCATTATTTTTTGCATTTGAAA    30
  1  AAGAGGAAAAAAATAAGTTAAAGGGGGGAAAAGTTTCATTTGCCTTAAAAAGGCACAATCTTGATAGAAAGGAGATAATTTAC            121

122  ATG GGT TGT ACG CTT ATA CTA ATG TTG AAT GTG TTG TTG GGT TCA TGG GTT TTT TCT GGA           190
  1  Met Gly Cys Thr Leu Ile Leu Met Leu Asn Val Leu Leu Gly Ser Trp Val Phe Ser Gly            23

191  ACA GCT TCT GTT TCA TAT GAC CAT AGG GCT ATT ATT GTA AAT GGA CAA AGA ATA CTT ATT TCT GGT   259
 24  Thr Ala Ser Val Ser Tyr Asp His Arg Ala Ile Ile Val Asn Gly Gln Arg Ile Leu Ile Ser Gly   46

260  TCT GTT CAT TAT CCA AGA AGC ACT CCT GAG ATG TGG CCA GGT ATT ATT CAA AAG GCT AAA GAA GGA GGT   328
 47  Ser Val His Tyr Pro Arg Ser Thr Pro Glu Met Trp Pro Gly Ile Ile Gln Lys Ala Lys Glu Gly Gly   69

329  GTG GAT GTG ATT CAG ACT TAT GTT TTC TGG AAT GGA CAT GAG CAT CAA CAA GGG AAA TAT TAT TTT GAA   397
 70  Val Asp Val Ile Gln Thr Tyr Val Phe Trp Asn Gly His Glu His Gln Gln Gly Lys Tyr Tyr Phe Glu   92

398  GGG AGA TAT GAT TTA GTG AAG TTT ATT AAG CTG GTG CAC CAA GCA GGA CTT TAT GTC CAT CTT AGA GTT   466
 93  Gly Arg Tyr Asp Leu Val Lys Phe Ile Lys Leu Val His Gln Ala Gly Leu Tyr Val His Leu Arg Val   115

467  GGA CCT TAT GCT TGT GCT GAA TGG AAT TTT GGG GGC TTT CCT GTT TGG CTG AAA TAT GTT CCA GGT ATC   535
116  Gly Pro Tyr Ala Cys Ala Glu Trp Asn Phe Gly Gly Phe Pro Val Trp Leu Lys Tyr Val Pro Gly Ile   138

536  AGT TTC AGA ACA GAT GGA CCT TTC AAG GCA ATG CAA AAA TTT ACT GCC AAG ATT GTC AAT ATG           604
139  Ser Phe Arg Thr Asp Gly Pro Phe Lys Ala Met Gln Lys Phe Thr Ala Lys Ile Val Asn Met          161

605  ATG AAA GCG GAA CGT TAT TTG TAT GAA ACT CAG GGG GGG CCA ATA ATT TTA TCT CAG ATT GAG AAT GAA TAT   673
162  Met Lys Ala Glu Arg Tyr Leu Tyr Glu Thr Gln Gly Gly Pro Ile Ile Leu Ser Gln Ile Glu Asn Glu Tyr   184
```

```
674  GGA CCC ATG GAA TGG GAA CTG GGA GCA CCA GGT AAA TCT TAC GCA CAG TGG GCC AAA ATG GCT GTG  742
185  Gly Pro Met Glu Trp Glu Leu Gly Ala Pro Gly Lys Ser Tyr Ala Gln Trp Ala Lys Met Ala Val  207

743  GGT CTT GAC ACT GGT GTC CCA TGG GTT ATG TGC AAG CAA GAC GAT GCC CCT GAT GCC CCT ATT AAT GCT  811
208  Gly Leu Asp Thr Gly Val Pro Trp Val Met Cys Lys Gln Asp Asp Ala Pro Asp Ala Pro Ile Asn Ala  230

812  TGC AAT GGC TTC TAC TGT GAC TAC TTT TCT CCA TAT AAA GCT TAT AAG ATA TGG ACT GAA GCC  880
231  Cys Asn Gly Phe Tyr Cys Asp Tyr Phe Ser Pro Tyr Lys Ala Tyr Lys Ile Trp Thr Glu Ala  253

881  TGG ACT GCA TGG TTT ACT GGT TTT GGA AAT CCA GTT CCT TAC CGT CCT GCT GAG GAC TTG GCA TTT TCT  949
254  Trp Thr Ala Trp Phe Thr Gly Phe Gly Asn Pro Val Pro Tyr Arg Pro Ala Glu Asp Leu Ala Phe Ser  276

950  GTT GCA AAA TTT ATA CAG AAG GGT TCC TTC ATC AAT TAT TAC ATG TAT CAT GGA GGA ACA AAC TTT  1018
277  Val Ala Lys Phe Ile Gln Lys Gly Ser Phe Ile Asn Tyr Tyr Met Tyr His Gly Gly Thr Asn Phe  299

1019 GGA CGG ACT GCT GGT GGT CCA TTT ATT GCT ACT AGT GAC TAT GAT GCA CCA CTT GAT GAA TAT GGA  1087
300  Gly Arg Thr Ala Gly Gly Pro Phe Ile Ala Thr Ser Asp Tyr Asp Ala Pro Leu Asp Glu Tyr Gly  322

1088 TTA TTG CGA CAA CCA AAA TGG CAC CTG AAA GAT CTG CAT AGA GCA ATA AAG CTT TGT GAA CCA GCT  1156
323  Leu Leu Arg Gln Pro Lys Trp His Leu Lys Asp Leu His Arg Ala Ile Lys Leu Cys Glu Pro Ala  345

1157 TTA TCT TCT GGA GAT CCA ACA GCT GTG GAC CTT GGA CAC CAG CAG GAG GCC CAT GTT TTT AGG TCG AAG  1225
346  Leu Ser Ser Gly Asp Pro Thr Ala Val Asp Leu Gly His Gln Gln Glu Ala His Val Phe Arg Ser Lys  368

1226 GCT GGC TCT TGT GCT GCA TTC CTT GCT GCA TAC AAC TAC GAC CAA CAC TCT TTT GCT ACT GTG TCA TTT GCA AAC  1294
369  Ala Gly Ser Cys Ala Ala Phe Leu Ala Ala Tyr Asn Tyr Asp Gln His Ser Phe Ala Thr Val Ser Phe Ala Asn  391
```

FIG. 2C-2

```
1295 AGG CAT TAC AAC TTG CCA CCA TGG TCA ATC AGC ATT CTT CCC GAC TGC AAG AAC ACT GTA TTT AAT ACA 1363
 392 Arg His Tyr Asn Leu Pro Pro Trp Ser Ile Ser Ile Leu Pro Asp Cys Lys Asn Thr Val Phe Asn Thr  414

1364 GCA CGG ATC GGT GCT CAA AGT GCT CAG ATG AAG ACT CCA AGC AGA GGA TTG CCC TGG CAG TCA 1432
 415 Ala Arg Ile Gly Ala Gln Ser Ala Gln Met Lys Thr Pro Ser Arg Gly Leu Pro Trp Gln Ser  437

1433 TTC AAT GAA GAG ACA TCA TCT TAT GAA GAC AGT AGT TTT ACA GTT GTT GGG CTA GAA CAG ATA AAT 1501
 438 Phe Asn Glu Glu Thr Ser Ser Tyr Glu Asp Ser Ser Phe Thr Val Val Gly Leu Glu Gln Ile Asn  460

1502 ACA AGA GAC GTG TCT GAT GTG TCT TAT TGG TTG TAT TCA ACA GAT GTC AAG ATT GAT TCA AGA GAA AAG TTT 1570
 461 Thr Arg Asp Val Ser Asp Val Ser Tyr Trp Leu Tyr Ser Thr Asp Val Lys Ile Asp Ser Arg Glu Lys Phe  483

1571 TTG AGA GGC GGA AAA TGG CCT TGG CTT ACG ATC ATG TCA GCT GGG CAT GCA TTG CAT GTT TTT GTG AAT 1639
 484 Leu Arg Gly Gly Lys Trp Pro Trp Leu Thr Ile Met Ser Ala Gly His Ala Leu His Val Phe Val Asn  506

1640 GGT CAA TTA GCA GGA ACT GGT GTT AAC AAG ATT TCT CTA CTG AAA CCG CTT GCT GTT GGC AAT GCC GTA AAT 1708
 507 Gly Gln Leu Ala Gly Thr Gly Val Asn Lys Ile Ser Leu Leu Lys Pro Leu Ala Val Gly Asn Ala Val Asn  529

1709 CTG AGA GCA GGT GTT AAT GCT GGT GTT CTT CTA ACT GGC ATT GCT CTA ACT TTC AGC CCG AAT ATC GGC CCA CAT 1777
 530 Leu Arg Ala Gly Val Asn Ala Gly Val Leu Leu Thr Gly Ile Ala Leu Thr Phe Ser Pro Asn Ile Gly Pro His  552

1778 TTT GAG ACA TGG AAT GCT GGT CTT GGG CCA GTC TCA ACT GGT CTT GAC GAG CTT GAC GGG AAA AGA GAT 1846
 553 Phe Glu Thr Trp Asn Ala Gly Leu Gly Pro Val Ser Thr Gly Leu Asp Glu Leu Asp Gly Lys Arg Asp  575

1847 TTA ACA TGG CAG AAA TGG TAC AAG GTT GGT CTA AAA GGA GAA GCC TTG AGC CTC CAT TCA CTC AGT 1915
 576 Leu Thr Trp Gln Lys Trp Tyr Lys Val Gly Leu Lys Gly Glu Ala Leu Ser Leu His Ser Leu Ser  598
```

FIG. 2C-3

| Pos | | | | | | | | | | | | | | | | | | | | | | | Pos |
|---|---|---|---|---|---|---|---|---|---|---|---|---|---|---|---|---|---|---|---|---|---|---|---|
| 1916 | GGT Gly | AGC Ser | TCG Ser | TCA Ser | GTT Val | GAG Glu | TGG Trp | GTC Val | GAG Glu | GGT Gly | TCT Ser | TTA Leu | GTG Val | GCT Ala | CAG Gln | AGA Arg | CAG Gln | CCA Pro | CTC Leu | ACA Thr | TGG Trp | TAC Tyr | AAG Lys | 1984 |
| 599 | | | | | | | | | | | | | | | | | | | | | | | 621 |
| 1985 | AGC Ser | ACT Thr | TTT Phe | AAT Asn | GCT Ala | CCA Pro | GCT Ala | GGA Gly | AAT Asn | GAT Asp | CCT Pro | TTG Leu | GCT Ala | TTA Leu | GAC Asp | TTG Leu | AAT Asn | ACC Thr | ATG Met | GGC Gly | AAA Lys | GGA Gly | CAA Gln | 2053 |
| 622 | | | | | | | | | | | | | | | | | | | | | | | 644 |
| 2054 | GTG Val | TGG Trp | ATA Ile | AAT Asn | GGT Gly | CAA Gln | AGC Ser | CTC Leu | CGA Arg | CGC Gly | TAT Tyr | CCT Pro | GGA Gly | TAT Tyr | AAA Lys | GCA Ala | TCT Ser | GGT Gly | AAC Asn | TGC Cys | GGT Gly | GCC Ala | 2122 |
| 645 | | | | | | | | | | | | | | | | | | | | | | | 667 |
| 2123 | TGT Cys | AAC Asn | TAT Tyr | GCA Ala | GGC Gly | TGG Trp | TTT Phe | AAT Asn | GAG Glu | GTT Val | AAA Lys | TGC Cys | CTA Leu | AGT Ser | AAC Asn | TGT Cys | GGA Gly | GAG Glu | GCT Ala | TCA Ser | CAA Gln | CGA Arg | TGG Trp | 2191 |
| 668 | | | | | | | | | | | | | | | | | | | | | | | 690 |
| 2192 | TAT Tyr | CAT His | GTT Val | CCC Pro | CGT Arg | TCT Ser | TGG Trp | CTG Leu | TAT Tyr | CCT Pro | ACT Thr | GGA Gly | AAT Asn | TTG Leu | TTA Leu | GTT Val | CTA Leu | TTT Phe | GAG Glu | GTT Val | TGG Trp | GGA Gly | GGA Gly | 2260 |
| 691 | | | | | | | | | | | | | | | | | | | | | | | 713 |
| 2261 | GAG Glu | CCT Pro | CAT His | GGA Gly | ATC Ile | TCT Ser | TTG Leu | GTA Val | AAA Lys | AGA Arg | GAA Glu | GTT Val | GCA Ala | AGT Ser | GTT Val | TGT Cys | GCA Ala | GAT Asp | ATA Ile | AAC Asn | GAA Glu | TGG Trp | CAA Gln | 2329 |
| 714 | | | | | | | | | | | | | | | | | | | | | | | 736 |
| 2330 | CCA Pro | CAG Gln | TTG Leu | GTG Val | AAT Asn | TGG Trp | CAA Gln | ATG Met | GCA Ala | TCT Ser | GGT Gly | AAA Lys | GTT Val | GAC Asp | AAA Lys | CCA Pro | CTG Leu | AGA Arg | CCT Pro | AAA Lys | GCT Ala | CAC His | 2398 |
| 737 | | | | | | | | | | | | | | | | | | | | | | | 759 |
| 2399 | CTC Leu | TCG Ser | TGT Cys | GCT Ala | TCT Ser | GGT Gly | GGA Gly | CAG Gln | CAG Gln | AAG Lys | ATT Ile | ACT Thr | TCA Ser | ATC Ile | AAA Lys | TTT Phe | GCA Ala | AGC Ser | TTT Phe | GGA Gly | ACA Thr | CCA Pro | GTC Val | 2467 |
| 760 | | | | | | | | | | | | | | | | | | | | | | | 782 |
| 2468 | TGC Cys | GGA Gly | AGC Ser | TTC Phe | CGT Arg | GAA Glu | AGC Ser | TGC Cys | CAC His | TTC Phe | CAC His | TCA Ser | TAT Tyr | GCC Ala | TTC Phe | GAT Asp | GCT Ala | TTT Phe | GAA Glu | TAT Tyr | TGC Cys | ATC Ile | 2536 |
| 783 | | | | | | | | | | | | | | | | | | | | | | | 805 |

FIG. 2C-4

```
2537 GGG CAA AAC TCG TGC TCA GTA CCT GTA ACA CCA GAG ATC TTT GGA GGT GAT CCA TGT CCA CAT GTT ATG    2605
 806 Gly Gln Asn Ser Cys Ser Val Pro Val Thr Pro Glu Ile Phe Gly Gly Asp Pro Cys Pro His Val Met     828

2606 AAG AAA CTC TCA GTT GAG GTT ATT TGC AGT TGA TGACACTGAGGAGAAACAAATAAAAGTGTTTCAGTTAGTGTCTGAA     2686
 829 Lys Lys Leu Ser Val Glu Val Ile Cys Ser ***                                                     840

2687 CATATCAAAAAGTTGGCTTTGATGGAGGTGAAGTTGTACAGATATGCAACACACCTTTCCATTTGAGGCACATATGAATTGCAATGGCCCAA    2778
2779 GATTCTGTACATATGTGGTTACTGTGTCAAGTTGGTTATTGGTTTGCAAATGTAAAACAGTAGTCATTGGTTCAAGTGCGCATCGAG         2870
2871 ATTGTGCTAGTGGGAGGTAGTAGTAGTACCGATCGATCATCGTTGTTTGCACAAGCTGGGCTTGCACAAGCTATTATTATAACAAGAAAGC    2962
2963 ACAATGAGACTGATTCTTGATTAGTCCATGTGTAGATATTGTTACTGTTGATTTGCAAATCTTGTGATTTCAGCAAAAAAAAAAAAAAAA     3054
3055 AAAAAAAAAAAAA                                                                                    3069
```

FIG. 2C-5

```
1                                                       AAAAAAGTTTCAATTTTTTCTAAATAAAAAAAATTCATTTTTTTGAATGTGGAAAAA              63

64   ATG CTA AGG ACT AAT GTG TTG TTA TTA GTT ATT TGT TTA TTG GAT TTT TTT TCT TCA GTG AAA GCT            132
1    Met Leu Arg Thr Asn Val Leu Leu Leu Val Ile Cys Leu Leu Asp Phe Phe Ser Ser Val Lys Ala            23

133  AGT GTT TCT TAT GAT GAC AGA GCT ATA ATC ATA AAT GGG AAA AGA AAA ATT CTT ATT TCT GGT TCA ATT        201
24   Ser Val Ser Tyr Asp Asp Arg Ala Ile Ile Ile Asn Gly Lys Arg Lys Ile Leu Ile Ser Gly Ser Ile        46

202  CAT TAT CCA AGA AGC ACT CCA CAG ATG TGG CCT GAT CTT ATA CAA AAG GCT AAA GAT GGA GGC TTA GAT        270
47   His Tyr Pro Arg Ser Thr Pro Gln Met Trp Pro Asp Leu Ile Gln Lys Ala Lys Asp Gly Gly Leu Asp        69

271  GTT ATT GAA ACT TAT GTT TTC TGG AAT GGA CAT GAG CCT TCT CCT GGA AAA TAT AAT TTT GAA GGA AGA        339
70   Val Ile Glu Thr Tyr Val Phe Trp Asn Gly His Glu Pro Ser Pro Gly Lys Tyr Asn Phe Glu Gly Arg        92

340  TAT GAT CTT GTT AGA TTC ATC AAA ATG GTA CAA AGA GCA GGA CTT TAT GTC AAT TTA CGT ATT GGC CCT        408
93   Tyr Asp Leu Val Arg Phe Ile Lys Met Val Gln Arg Ala Gly Leu Tyr Val Asn Leu Arg Ile Gly Pro        115
```

FIG. 2D-1

```
409  TAC GTC TGT GCT GAA TGG AAC TTT GGG GGA TTC CCT GTT TGG CTA AAA TAT GTG CCT GGT ATG GAA TTT   477
116  Tyr Val Cys Ala Glu Trp Asn Phe Gly Gly Phe Pro Val Trp Leu Lys Tyr Val Pro Gly Met Glu Phe  138

478  AGA ACA AAC AAT CAG CCT TTT AAG GTG GCT ATG CAA GGA TTT GTT CAG AAA ATA GTC AAC ATG ATG AAG   546
139  Arg Thr Asn Asn Gln Pro Phe Lys Val Ala Met Gln Gly Phe Val Gln Lys Ile Val Asn Met Met Lys  161

547  TCA GAA AAT TTG TTT GAA TCT CAA GGA GGA CCA ATA ATT ATG GCC CAG ATA GAA AAT GAG TAT GGA CCA   615
162  Ser Glu Asn Leu Phe Glu Ser Gln Gly Gly Pro Ile Ile Met Ala Gln Ile Glu Asn Glu Tyr Gly Pro  184

616  GTA GAA TGG GAA ATT GGT GCT CCT GGT TAT ACA TAT ACA AAA CAA ATG GCA ATG CAA GTA GGT TTG       684
185  Val Glu Trp Glu Ile Gly Ala Pro Gly Tyr Thr Tyr Thr Lys Gln Met Ala Gln Met Ala Val Gly Leu  207

685  AAA ACT GGT GTC CCA TGG ATC ATG TGT TAT ACA GAG CAA GAT GCT CCT GAT CCT GTG ATT GAT ACT TGT AAT  753
208  Lys Thr Gly Val Pro Trp Ile Met Cys Tyr Thr Glu Gln Asp Ala Pro Asp Pro Val Ile Asp Thr Cys Asn  230

754  GGC TTC TAC TGC GAA GGG CTT CGT TTC AAG CAA GAT CCT AAA CCT TAC AGA CCA CAA AGA ATG TGG ACT   822
231  Gly Phe Tyr Cys Glu Gly Leu Arg Phe Lys Gln Asp Pro Lys Pro Tyr Arg Pro Gln Arg Met Trp Thr  253

823  GGC TGG TAT ACG AAA TTC GGT GGT CCA ATT CCT CAA AGA CCA GCC GAA GAC ATT GCA TTT TCA GTT GCC   891
254  Gly Trp Tyr Thr Lys Phe Gly Gly Pro Ile Pro Gln Arg Pro Ala Glu Asp Ile Ala Phe Ser Val Ala  276

892  AGG TTT GTT CAG AAC AAT GGT TCA TTC TTC AAT TAC TAC ATG TAT CAT GGA GGA ACA AAT TTT GGC CGG   960
277  Arg Phe Val Gln Asn Asn Gly Ser Phe Phe Asn Tyr Tyr Met Tyr His Gly Gly Thr Asn Phe Gly Arg  299

961  ACA TCA GGG CTT TTC ATT GCA ACT AGC GAT TAT GAT GCT CCT CTC GAT GAA TAT GGG TTG CTG       1029
300  Thr Ser Gly Leu Phe Ile Ala Thr Ser Asp Tyr Asp Ala Pro Leu Asp Glu Tyr Gly Leu Leu       322
```

FIG. 2D-2

| | | | | | | | | | | |
|---|---|---|---|---|---|---|---|---|---|---|
| 1030 | AAT | GAA | CCA | AAG | TAT | GGG | CAC | TTG | AGA | GAC | TTA | CAT | AAA | GCT | ATC | AAG | CTA | TCT | GAA | CCG | GCT | TTA | GTT | 1098 |
| 323 | Asn | Glu | Pro | Lys | Tyr | Gly | His | Leu | Arg | Asp | Leu | His | Lys | Ala | Ile | Lys | Leu | Ser | Glu | Pro | Ala | Leu | Val | 345 |
| 1099 | TCA | TCA | TAT | GCT | GCG | GTG | ACT | AGT | CTT | GGA | AGT | AAT | CAA | GAG | GCT | CAT | GTT | TAT | AGA | TCA | AAA | TCT | GGA | 1167 |
| 346 | Ser | Ser | Tyr | Ala | Ala | Val | Thr | Ser | Leu | Gly | Ser | Asn | Gln | Glu | Ala | His | Val | Tyr | Arg | Ser | Lys | Ser | Gly | 368 |
| 1168 | GCT | TGT | GCT | TTT | TTA | TCC | AAC | TAT | GAC | TCT | AGA | TAT | TCA | GTA | AAA | GTC | ACC | TTT | CAG | AAT | AGG | CCA | 1236 |
| 369 | Ala | Cys | Ala | Ala | Phe | Leu | Ser | Asn | Tyr | Asp | Ser | Arg | Tyr | Ser | Val | Lys | Val | Thr | Phe | Gln | Asn | Arg | Pro | 391 |
| 1237 | TAC | AAT | CTG | CCT | CCA | TGG | TCC | ATC | AGC | ATT | CTT | CCC | GAC | GTT | TAC | AAC | ACT | GCC | GTT | TAC | AAC | ACT | GCA | CAG | 1305 |
| 392 | Tyr | Asn | Leu | Pro | Pro | Trp | Ser | Ile | Ser | Ile | Leu | Pro | Asp | Cys | Lys | Thr | Ala | Val | Tyr | Asn | Thr | Ala | Gln | 414 |
| 1306 | GTT | AAC | TCT | CAA | AGC | TCG | ATA | AAG | ATG | ACG | CCT | GCA | GGT | GGA | TTG | TCT | TGG | CAG | TCA | TAC | AAT | 1374 |
| 415 | Val | Asn | Ser | Gln | Ser | Ser | Ile | Lys | Met | Thr | Pro | Ala | Gly | Gly | Leu | Ser | Trp | Gln | Ser | Tyr | Asn | 437 |
| 1375 | GAA | ACG | CCT | ACT | GCT | GAT | GAC | AGC | GAT | ACA | CTT | ACA | GCT | AAC | GGA | CTA | TGG | GAA | CAG | AAA | AAC | GTC | 1443 |
| 438 | Glu | Thr | Pro | Thr | Ala | Asp | Asp | Ser | Asp | Thr | Leu | Thr | Ala | Asn | Gly | Leu | Trp | Glu | Gln | Lys | Asn | Val | 460 |
| 1444 | ACA | AGA | GAT | TCA | TCA | GAC | TAT | CTG | TGG | TAC | ATG | ACA | AAT | GTA | AAT | ATA | GCA | TCT | AAT | GAA | GGA | TTT | CTA | 1512 |
| 461 | Thr | Arg | Asp | Ser | Ser | Asp | Tyr | Leu | Trp | Tyr | Met | Thr | Asn | Val | Asn | Ile | Ala | Ser | Asn | Glu | Gly | Phe | Leu | 483 |
| 1513 | AAG | AAC | GGA | AAG | GAT | CCT | ATG | ATG | TCC | GCT | GGT | CAT | GTC | TTG | CAT | GTC | TTC | GTC | AAT | GGA | 1581 |
| 484 | Lys | Asn | Gly | Lys | Asp | Pro | Tyr | Leu | Thr | Val | Met | Ser | Ala | Gly | His | Val | Leu | His | Val | Phe | Val | Asn | Gly | 506 |
| 1582 | AAA | CTA | TCA | GGA | ACT | GTT | TAT | GGT | ACA | TTG | GAT | AAT | CCA | AAA | CTT | ACA | TAC | AGT | GGC | AAC | GTG | AAG | TTA | 1650 |
| 507 | Lys | Leu | Ser | Gly | Thr | Val | Tyr | Gly | Thr | Leu | Asp | Asn | Pro | Lys | Leu | Thr | Tyr | Ser | Gly | Asn | Val | Lys | Leu | 529 |

FIG. 2D-3

```
1651 AGA GCT GGT ATT AAC AAG ATT TCT CTG CTC AGT GTT TCC GTT GGT CTC CCG AAC GTT GGC GTG CAT TAT   1719
 530 Arg Ala Gly Ile Asn Lys Ile Ser Leu Leu Ser Val Ser Val Gly Leu Pro Asn Val Gly Val His Tyr    552

1720 GAT ACA GGA AAT GCA GTT CTA GGT GTC CCA GTT ACG TTG AGC GGT CTC AAT GAA GGG TCA AGA AAC TTG   1788
 553 Asp Thr Gly Asn Ala Val Leu Gly Val Pro Val Thr Leu Ser Gly Leu Asn Glu Gly Ser Arg Asn Leu    575

1789 GCG AAA CAG AAA TGG CAG TCT TAC AAG GTT GGT CTG AAA GGC GAA TCG TTA AGT CTT CAC TCC TTA AGT GGG   1857
 576 Ala Lys Gln Lys Trp Gln Ser Tyr Lys Val Gly Leu Lys Gly Glu Ser Leu Ser Leu His Ser Leu Ser Gly    598

1858 AGT TCT TCT GTT GAA TGG CGA GGT TCA CTA ATG GCT CAA CAG CCC CTG ACT TGG TAC TAC AAG GCT   1926
 599 Ser Ser Ser Val Glu Trp Arg Gly Ser Leu Met Ala Gln Gln Pro Leu Thr Trp Tyr Tyr Lys Ala    621

1927 ACA TTT AAC GCG CCT GGA GGA AAT GAT CCA CTA GCT TTA GAC ATG GCA AGT ATG GGA AAA GGT CAG ATA   1995
 622 Thr Phe Asn Ala Pro Gly Gly Asn Asp Pro Leu Ala Leu Asp Met Ala Ser Met Gly Lys Gly Gln Ile    644

1996 TGG ATA AAT GGT GAA GGC GTA GGT GGC CAT CGC TAT ATA GCA CAA GGC GAC TGC AGC AAA TGC   2064
 645 Trp Ile Asn Gly Glu Gly Val Gly Gly His Arg Tyr Ile Ala Gln Gly Asp Cys Ser Lys Cys    667

2065 AGT TAT GCT GGA ACG TTC AAC GAG AAG TGC CAG ACT AAC TGC AAT CCT TCT CAG AGA TGG TAC   2133
 668 Ser Tyr Ala Gly Thr Phe Asn Glu Lys Cys Gln Thr Asn Cys Asn Pro Ser Gln Arg Trp Tyr    690

2134 CAT GTT CCA CGA TCG TGG CTG AAA CCA AGT GGA AAC TTG GTA GTA TTC GAA GAA TGG GGA GGT AAT   2202
 691 His Val Pro Arg Ser Trp Leu Lys Pro Ser Gly Asn Leu Val Val Phe Glu Glu Trp Gly Gly Asn    713

2203 CCA ACA GGA ATT TCT CTA GTC AGG AGA TCA AGA TAA AGAACTCGAAAAGTAAAACTTGTTCAGTAACTATGGTGCTTGAA   2282
 714 Pro Thr Gly Ile Ser Leu Val Arg Arg Ser Arg ***                                                   725
```

FIG. 2D-4

```
2283  TTCGCGCCGAAAAATACATACACGAAGCTAACAATGGAGGCTACAGTTTGCAAATTGCAGCTGAATAAAACATTAGAAGATAAAGAAATATT  2374
2375  TGATTAAAAGGAGTATATAAATTTACAGAGAATTTTCTTTATTCTTTATTCTTTGTAAAACTTGTTTATAAAGTTTATACAGAATTTCTGTTATTT  2466
2467  GGATTATGAGAGATTGAAGAAGATTGTACAGCTTCCAAATACTATTAGAATACAAATAAATTTCATGTAAAAAAAAAAAAAAAAAA  2554
```

FIG. 2D-5

```
  1 ATC CAG ACT TAC GTT TTC TGG AAC CTT CAT GAA CCT GTT CGA AAT CAG TAT GAT TTT GAA GGA AGG AAA   69
  1 Ile Gln Thr Tyr Val Phe Trp Asn Leu His Glu Pro Val Arg Asn Gln Tyr Asp Phe Glu Gly Arg Lys   23

70 GAT TTG ATT AAT TTT GTG AAG TTG GTG GAG AGA GCT GGC TTA TTT GTT CAT ATA AGG ATT GGG CCT TAT  138
 24 Asp Leu Ile Asn Phe Val Lys Leu Val Glu Arg Ala Gly Leu Phe Val His Ile Arg Ile Gly Pro Tyr   46

139 GTT TGT GCA GAA TGG TAT AAC TAT GGT GGG TTT CCT CTT TGG CAT TTG ATT CCT GGA ATT GAA TTT CGA  207
 47 Val Cys Ala Glu Trp Tyr Asn Tyr Gly Gly Phe Pro Leu Trp His Leu Ile Pro Gly Ile Glu Phe Arg   69

208 ACC GAC AAT GAA CCG TTC AAG GCA GAA ATG AAG CGA TTC ACA GCT AAA ATT GAC ATG GTT GAC ATC AAG CAA  276
 70 Thr Asp Asn Glu Pro Phe Lys Ala Glu Met Lys Arg Phe Thr Ala Lys Ile Asp Met Val Asp Ile Lys Gln   92

277 GAA AAT CTA TAT GCA TCC CAG GGT GGG CCG GTT ATC TCT CAG ATA GAA AAT GAG TAT GGC AAT GGT  345
 93 Glu Asn Leu Tyr Ala Ser Gln Gly Gly Pro Val Ile Ser Gln Ile Glu Asn Glu Tyr Gly Asn Gly  115

346 GAT ATT GAG TCT CGT TAT GGT CCT CGT GCC AAA CCT TAC GTG AAC TGG GCA GCA TCA ATG GCT ACG TCT  414
116 Asp Ile Glu Ser Arg Tyr Gly Pro Arg Ala Lys Pro Tyr Val Asn Trp Ala Ala Ser Met Ala Thr Ser  138

415 TTA AAT ACG GGA GTG CCA TGG GTT ATG TGT CAG CAA CCA GAT GCC CCT TCC GTT ATT AAC ACT TGC  483
139 Leu Asn Thr Gly Val Pro Trp Val Met Cys Gln Gln Pro Asp Ala Pro Ser Val Ile Asn Thr Cys  161

484 AAT GGA TTT TAT TGT TGT GAC TTC AAG CAA TTC AAG CCC GAT AAA ACA TCC AAG ATG ACT GAG AAT TGG  552
162 Asn Gly Phe Tyr Cys Cys Asp Phe Lys Gln Phe Lys Pro Asp Lys Thr Ser Lys Met Thr Glu Asn Trp  184
```

FIG. 2E-1

```
553  ACC GGA TGG TTT CTG TCG TTT GGT CCT GTC CCT TAC AGA CCA GTG GAA GAC ATC GCT TTC GCT GTG  621
185  Thr Gly Trp Phe Leu Ser Phe Gly Pro Val Pro Tyr Arg Pro Val Glu Asp Ile Ala Phe Ala Val  207

622  GCT CGA TTT TTC CAG CGA GGC GGA ACT GGA ACT TTC CAG TAT TAC ATG TAC CAC GGG GGA ACT AAC TTT GGG  690
208  Ala Arg Phe Phe Gln Arg Gly Gly Thr Gly Thr Phe Gln Tyr Tyr Met Tyr His Gly Gly Thr Asn Phe Gly  230

691  AGA ACC AGT GGA CCG TTT ATT GCA ACT AGC TAT GAC GAT GCC CCT CTC GAC GAA TAC GG  755
231  Arg Thr Ser Gly Pro Phe Ile Ala Thr Ser Tyr Asp Asp Ala Pro Leu Asp Glu Tyr  252
```

FIG. 2E-2

```
  1 ATC CAG ACA TAT GTT TTT TGG AAT GTT CAT GAG CCT TCT CCT GGC AAT TAC AAT TTT GAA GGA AGA TAT   69
  1 Ile Gln Thr Tyr Val Phe Trp Asn Val His Glu Pro Ser Pro Gly Asn Tyr Asn Phe Glu Gly Arg Tyr   23

70 GAC CTG GTG AGG TTT GTA AAA ACG ATT CAG AAA GCA GGG CTG TAT GCT CTT CGA ATT GGC CCT TAC       138
 24 Asp Leu Val Arg Phe Val Lys Thr Ile Gln Lys Ala Gly Leu Tyr Ala Leu Arg Ile Gly Pro Tyr       46

139 GTT TGT GCA GAG TGG AAT TTT GGA GGG TTT CCA GTA TGG CTG AAG TAT GTA CCT GGC ATT AGC TTC AGA  207
 47 Val Cys Ala Glu Trp Asn Phe Gly Gly Phe Pro Val Trp Leu Lys Tyr Val Pro Gly Ile Ser Phe Arg   69

208 GCT GAT AAT GAA CCT TTC AAG AAC GCA ATG GGG TAT GCT GAG AAA ATT GTT AAC TTG ATG AAG ATC       276
 70 Ala Asp Asn Glu Pro Phe Lys Asn Ala Met Gly Tyr Ala Glu Lys Ile Val Asn Leu Met Lys Ile       92

277 ATA ATC TTT TCG AGT CTC AGG GTG GTC CAA TCA TAC TCT CAC AGA AGA ATG AGT ATG GGC CTC AAG       345
 93 Ile Ile Phe Ser Ser Leu Arg Val Val Gln Ser Tyr Ser His Arg Arg Met Ser Met Gly Leu Lys      115

346 CCA AGG TAC TTG GAG CAC CGG GAC ATC AGT ATT CAA CAT GGG CTG CAA ATA TGG CAG TTG GAT TTG AAC  414
116 Pro Arg Tyr Leu Glu His Arg Asp Ile Ser Ile Gln His Gly Leu Gln Ile Trp Gln Leu Asp Leu Asn  138
```

FIG. 2F-1

```
415  ACA GCC GTC CCA TGG GTG ATG TGC AAG GAA GAT GCA CCA GAT CCT GTG ATC AAC ACA TGC AAT GGT  483
139  Thr Gly Val Pro Trp Val Met Cys Lys Glu Asp Ala Pro Asp Pro Val Ile Asn Thr Cys Asn Gly  161

484  TTC TAC TGT GAT AAT TTC TTC CCA AAC TAC AAA CCT TAT TGG ACT GAA GCT TGG AGT GGA  552
162  Phe Tyr Cys Asp Asn Phe Phe Pro Asn Lys Pro Tyr Trp Thr Glu Ala Trp Ser Gly  184

553  TGG TTC TCG GAA TTT GGC GGT CCC CTT CAT CAG AGA GTT CCA GAT TTG GCA TTT GCT GTT GCC CAA  621
185  Trp Phe Ser Glu Phe Gly Gly Pro Leu His Gln Arg Val Pro Asp Leu Ala Phe Ala Val Ala Gln  207

622  TTT ATA CAA AGA GGA TCT TTT GTT AAC TAT TAC ATG TAC CAT GGG GGC ACG AAC TTT GGA CGC ACT  690
208  Phe Ile Gln Arg Gly Ser Phe Val Asn Tyr Tyr Met Tyr His Gly Gly Thr Asn Phe Gly Arg Thr  230

691  GCG GGT GGG CCA TTC ATC ACT AGC TAT GAT TAT GAT GCC CCC CTC GAC GAG TAT GG  749
231  Ala Gly Gly Pro Phe Ile Thr Ser Tyr Asp Tyr Asp Ala Pro Leu Asp Glu Tyr  250
```

FIG. 2F-2

```
  1                                                          GCAACTTCTCCG   12
 13 GTGAATAACACCGGTAAACGGCCAATGCCAACTCTCGTCGGAATCTGAATACTGATTTAAGCAGCTTAGCTAACTTTGCCTCTGCA  103

104 ATG AAC ACA ATG AGT TGT TTG TCC TCT AAT TTC AAG TTC GTT TTC CTT GCC TCG ACT GTG ATA TGG ATG  172
  1 Met Asn Thr Met Ser Cys Leu Ser Ser Asn Phe Lys Phe Val Phe Leu Ala Ser Thr Val Ile Trp Met   23

173 ACG GTA ATG TCG TCG TCG TTA GCA GCA GTA GAT GCT TCC AAT GTT ACT ACT ATT GGT ACT GAT AGT GTG  241
 24 Thr Val Met Ser Ser Ser Leu Ala Ala Val Asp Ala Ser Asn Val Thr Thr Ile Gly Thr Asp Ser Val   46

242 ACT TAC GAT CGA CGC TCG TTG ATT ATT AAC GGC CAG AGG AAG CTG CTC ATC TCC GCT TCC ATT CAC TAT  310
 47 Thr Tyr Asp Arg Arg Ser Leu Ile Ile Asn Gly Gln Arg Lys Leu Leu Ile Ser Ala Ser Ile His Tyr   69
```

FIG. 2G-1

| | | | | | | | | | | |
|---|---|---|---|---|---|---|---|---|---|---|
| 311 | CCT | CGC | AGT | GTC | CCT | GCC | ATG | TGG | CCT | GGT | GTT | CGA | TTG | GCG | AAG | GAA | GGA | GTG | GAT | GTT | ATT | 379 |
| 70 | Pro | Arg | Ser | Val | Pro | Ala | Met | Trp | Pro | Gly | Val | Arg | Leu | Ala | Lys | Glu | Gly | Val | Asp | Val | Ile | 92 |
| 380 | GAA | ACG | TAT | GTT | TTC | TGG | AAC | GGT | CAC | GAA | CCT | TCT | CCG | GGC | AAT | TAT | TAC | TTT | GGA | GGA | AGG | TTT | GAT | 448 |
| 93 | Glu | Thr | Tyr | Val | Phe | Trp | Asn | Gly | His | Glu | Pro | Ser | Pro | Gly | Asn | Tyr | Tyr | Phe | Gly | Gly | Arg | Phe | Asp | 115 |
| 449 | CTA | GTC | AAA | TTT | TGT | AAG | ATC | ATT | CAG | CAG | GCT | GGA | ATG | ATT | CTT | CGG | ATT | GGA | CCA | TTT | GTA | 517 |
| 116 | Leu | Val | Lys | Phe | Cys | Lys | Ile | Ile | Gln | Gln | Ala | Gly | Met | Ile | Leu | Arg | Ile | Gly | Pro | Phe | Val | 138 |
| 518 | GCT | GCA | GAA | TGG | TTT | GGT | GGA | CTT | CCT | GTG | TGG | TTG | CAT | TAT | GTG | CCA | GGT | ACC | ACC | TTT | CGG | ACT | 586 |
| 139 | Ala | Ala | Glu | Trp | Phe | Gly | Gly | Leu | Pro | Val | Trp | Leu | His | Tyr | Val | Pro | Gly | Thr | Thr | Phe | Arg | Thr | 161 |
| 587 | GAT | AGT | GAA | CCA | TTT | AAG | TAT | CAC | ATG | CAG | AAG | TTC | ATG | ACA | TAT | ACA | GTG | AAC | TTA | ATG | AAG | AGA | GAG | 655 |
| 162 | Asp | Ser | Glu | Pro | Phe | Lys | Tyr | His | Met | Gln | Lys | Phe | Met | Thr | Tyr | Thr | Val | Asn | Leu | Met | Lys | Arg | Glu | 184 |
| 656 | AGG | CTT | TTT | GCA | TCT | CAA | GGA | GGT | CCA | ATC | ATC | TTG | TCA | CAG | GTA | GAA | AAT | GAG | TAC | GGC | TAC | TAT | GAA | 724 |
| 185 | Arg | Leu | Phe | Ala | Ser | Gln | Gly | Gly | Pro | Ile | Ile | Leu | Ser | Gln | Val | Glu | Asn | Glu | Tyr | Gly | Tyr | Tyr | Glu | 207 |
| 725 | AAT | GCA | TAT | GGA | GAA | GGG | AAA | AGG | TAT | GCC | TTA | TGG | GCT | GCT | AAA | ATG | GCC | CTT | TCT | CAA | AAT | ACT | 793 |
| 208 | Asn | Ala | Tyr | Gly | Glu | Gly | Lys | Arg | Tyr | Ala | Leu | Trp | Ala | Ala | Lys | Met | Ala | Leu | Ser | Gln | Asn | Thr | 230 |
| 794 | GGT | GTA | CCT | TGG | ATA | ATG | TGC | CAG | CAG | TAT | GAT | GCT | CCT | GAT | CCT | GTG | ATT | GAC | ACA | TGC | AAT | TCA | TTT | 862 |
| 231 | Gly | Val | Pro | Trp | Ile | Met | Cys | Gln | Gln | Tyr | Asp | Ala | Pro | Asp | Pro | Val | Ile | Asp | Thr | Cys | Asn | Ser | Phe | 253 |
| 863 | TAC | TGC | GAC | CAA | TTT | AAA | CCA | ATC | TCT | CCA | AAC | AAG | CCC | AAA | ATT | TGG | ACA | GAG | ACC | AAG | TGG | CCG | GGA | TGG | 931 |
| 254 | Tyr | Cys | Asp | Gln | Phe | Lys | Pro | Ile | Ser | Pro | Asn | Lys | Pro | Lys | Ile | Trp | Thr | Glu | Thr | Lys | Trp | Pro | Gly | Trp | 276 |

FIG. 2G-2

```
 932 TTC AAG ACA TTT GGG GCC AGA GAT CCT CAC AGG CCT GCA GAA GAT GTT GCT TAT TCC GTG GCT CGT TTT 1000
 277 Phe Lys Thr Phe Gly Ala Arg Asp Pro His Arg Pro Ala Glu Asp Val Ala Tyr Ser Val Ala Arg Phe  299

1001 TTC CAA AAA GGA AGC CAG AAT TAT TAC ATG CAT GGT GGG ACG AAC TTT GGC AGG ACA GCA 1069
 300 Phe Gln Lys Gly Ser Gln Asn Tyr Tyr Met His Gly Gly Thr Asn Phe Gly Arg Thr Ala  322

1070 GGT GGC CCT TTC ATT ACC AGT TAT GAC TAT GAC GCC CCA ATT GAC GAA TAT GGT TTA CCA GGT TTA AGG TTT 1138
 323 Gly Gly Pro Phe Ile Thr Ser Tyr Asp Tyr Asp Ala Pro Ile Asp Glu Tyr Gly Leu Pro Gly Leu Arg Phe  345

1139 CCA AAA GGT CAC CTT AAA GAA CTT CAT TAT AAA TCG ATA GTC AAG CAT GCT CTG AAC AAT 1207
 346 Pro Lys Gly His Leu Lys Glu Leu His Tyr Lys Ser Ile Val Lys His Ala Leu Asn Asn  368

1208 GAT CCA ACT CTT TCA TTA GGT CCT CTA CAA GAG GCT GAT GTT TAT GAA GAT GCT TCA GGC GCT TGT 1276
 369 Asp Pro Thr Leu Ser Leu Gly Pro Leu Gln Glu Ala Asp Val Tyr Glu Asp Ala Ser Gly Ala Cys  391

1277 GCT TTT CTC GCG AAT ATG GAT GAC AAA AAT GAC AAG GTG GTA CAG TTC CGA CAT GTA TCA TAC CAC 1345
 392 Ala Phe Leu Ala Asn Met Asp Asp Lys Asn Asp Lys Val Val Gln Phe Arg His Val Ser Tyr His  414

1346 TTG CCA GCA TGG TCT GTT AGC ATT TTG CCA GAC TGC AAA TGC AAC ACA GCA GCA AAG GTT GGA 1414
 415 Leu Pro Ala Trp Ser Val Ser Ile Leu Pro Asp Cys Lys Cys Asn Thr Ala Phe Ala Lys Val Gly  437

1415 TGT CAA ACT TCT ATT GTC AAT ATG GCA CCC ACC GCA AGT TCA CCA AAG AGA GAC 1483
 438 Cys Gln Thr Ser Ile Val Asn Met Ala Pro Thr Ala Ser Ser Pro Lys Arg Asp  460

1484 ATC AAG TCT CTT CAG TGG GAA GTC TTC AAG GAA ACA GCT GGA GTA TGG GGA GTT GCT GAT TTC ACT AAA 1552
 461 Ile Lys Ser Leu Gln Trp Glu Val Phe Lys Glu Thr Ala Gly Val Trp Gly Val Ala Asp Phe Thr Lys  483
```

FIG. 2G-3

```
1553 AAC GGA TTT GTA GAT CAC ATT AAC ACC ACA AAA GAT GCT ACA GAC TAC CTC TGG TAC ACA ACA AGT ATT 1621
484 Asn Gly Phe Val Asp His Ile Asn Thr Thr Lys Asp Ala Thr Asp Tyr Leu Trp Tyr Thr Thr Ser Ile 506

1622 TTT GTT CAT GCA GAG GAG GAT TTC CTA AGA AAC AGA GGC ACT GCA ATG CTT TTC GTT GAA TCA AAG GGT 1690
507 Phe Val His Ala Glu Glu Asp Phe Leu Arg Asn Arg Gly Thr Ala Met Leu Phe Val Glu Ser Lys Gly 529

1691 CAT GCT ATG CAT GTC TTC ATC AAT AAA AAG CTT CAA GCC AGT GCA TCT GGA AAT GGC ACA GTG CCA CAG 1759
530 His Ala Met His Val Phe Ile Asn Lys Lys Leu Gln Ala Ser Ala Ser Gly Asn Gly Thr Val Pro Gln 552

1760 TTC AAG TTT GGA ACT CCT ATT GCT CTA AAG GCA GGG AAG AAT GAA ATT TCC TTG TTA AGC ATG ACT GTG 1828
553 Phe Lys Phe Gly Thr Pro Ile Ala Leu Lys Ala Gly Lys Asn Glu Ile Ser Leu Leu Ser Met Thr Val 575

1829 GGC CTA CAA ACA GCT GGA GCG TTT TAT GAA TGG ATT GGA GCT GGT CCA ACA AGT GTC AAA GTT GCA GGG 1897
576 Gly Leu Gln Thr Ala Gly Ala Phe Tyr Glu Trp Ile Gly Ala Gly Pro Thr Ser Val Lys Val Ala Gly 598

1898 TTC AAG ACT GGG ACT ATG GAC TTG ACT GCG TCT GCT TGG ACC TAT AAG ATT GGA TTG CAA GGA GAA CAT 1966
599 Phe Lys Thr Gly Thr Met Asp Leu Thr Ala Ser Ala Trp Thr Tyr Lys Ile Gly Leu Gln Gly Glu His 621

1967 TTG AGG ATA CAG AAG TCA TAT AAC TTG AAG AGT AAA ATT TGG GCA CCA ACT TCG CAG CCA CCA AAG CAA 2035
622 Leu Arg Ile Gln Lys Ser Tyr Asn Leu Lys Ser Lys Ile Trp Ala Pro Thr Ser Gln Pro Pro Lys Gln 644

2036 CAG CCC CTC ACA TGG TAT AAG GCA GTA GTA GAT GCG CCT CCT GGT AAT GAA CCT GTT GCA CTT GAT ATG 2104
645 Gln Pro Leu Thr Trp Tyr Lys Ala Val Val Asp Ala Pro Pro Gly Asn Glu Pro Val Ala Leu Asp Met 667

2105 ATT CAT ATG GGA AAA GGA ATG GCT TGG TTG AAT GGA CAA GAA ATT GGC AGA TAT TGG CCG AGG AGA ACT 2173
668 Ile His Met Gly Lys Gly Met Ala Trp Leu Asn Gly Gln Glu Ile Gly Art Tyr Trp Pro Arg Arg Thr 690
```

FIG. 2G-4

```
2174 TCT AAA TAT GAG AAT TGT GTT ACT CAA TGT GAC TAC AGA GGC AAA TTT AAC CCT GAT AAC TGT GTC ACT 2242
 691 Ser Lys Tyr Glu Asn Cys Val Thr Gln Cys Asp Tyr Arg Gly Lys Phe Asn Pro Asp Lys Cys Val Thr  713

2243 GGC TGT GGA CAA CCT ACA CAG AGA TGG TAT CAT GTG CCA TCT GTG TTC AAG CCA TCA GGA AAT GTC 2311
 714 Gly Cys Gly Gln Pro Thr Gln Arg Trp Tyr His Val Pro Ser Val Phe Lys Pro Ser Gly Asn Val  736

2312 TTA ATT ATC TTT GAG GAA ATA GGT GGA GAT CCC TCT CAA ATT AGA TTC TCA ATG CGA AAG GTT TCT GGA 2380
 737 Leu Ile Ile Phe Glu Glu Ile Gly Gly Asp Pro Ser Gln Ile Arg Phe Ser Met Arg Lys Val Ser Gly  759

2381 GCT TGT GGT CAT CTT TCA GTG GAC CAT CCA TCC TTT GAT GTT GAA AAT CTG CAA GGA AGT GAA ATT GAG 2449
 760 Ala Cys Gly His Leu Ser Val Asp His Pro Ser Phe Asp Val Glu Asn Leu Gln Gly Ser Glu Ile Glu  782

2450 AAC GAC AAA AAC AGG CCA ACT CTA AGT TTG AAA TGC CCC ACA AAT ACT AAT ATT TCC TCT GTC AAA TTT 2518
 783 Asn Asp Lys Asn Arg Pro Thr Leu Ser Leu Lys Cys Pro Thr Asn Thr Asn Ile Ser Ser Val Lys Phe  805

2519 GCC AGC TTT GGA AAT CCT AAT GGT ACA TGT GGC TCC TAC ATG CTA GGA GAC TGC CAC GAT CAG AAT TCT 2587
 806 Ala Ser Phe Gly Asn Pro Asn Gly Thr Cys Gly Ser Tyr Met Leu Gly Asp Cys His Asp Gln Asn Ser  828

2588 GCA GCA CTG GTC GAA AAG GTT TGC CTG AAC CAA CAA AAT GAG TGT GCA TTA GAA ATG TCC AGC GCA AAC TTT 2656
 829 Ala Ala Leu Val Glu Lys Val Cys Leu Asn Gln Gln Asn Glu Cys Ala Leu Glu Met Ser Ser Ala Asn Phe  851

2657 AAC ATG CAA TTG TGT CCA AGT ACA GTA AAG AAA CTT GCA GTG AAT GTG GAA GTT CTG GCA GTG TCA TTG CCC 2728
 852 Asn Met Gln Leu Cys Pro Ser Thr Val Lys Lys Leu Ala Val Asn Val Glu Val Leu Ala Val Cys Ser ***  871

2729 AAAATGAATGACATATTCTAATTTATATAGTTGCTACGGAGATGCTCATTCTTAAACCTTTCTTATATAGCAGAAAAATCTGCTATTCCTT 2820
2821 CTTTCGTCTATGATTTGAAGTTTAAGATATGAGTACTGATGTCTTATTAAGCATCACCAGATAACCTTGGATATTCATGTTTGAAAGACTAA 2912
2913 GTATTCATATTTATTCAGTCGAGATGCAAGATTTATTTGTGAAAAAAAAAAAAAAAAAAAAAAA 2972
```

FIG. 2G-5

```
                         10         20         30         40         50
TBG1-ORF   -24   .......... ..........  ....MGFWMA MLLMLLLCLW VSCGISVSYD    26
TBG2-ORF   -14   .......... .....MSRRKT LNFPLILTVL TIHFVIVAGE YFKPFNVTYD    36
TBG3-ORF   -20   .......... .......... MGCTLILMLN VLLVLLGSWV FSGTASVSYD    30
TBG4-ORF   -22   .......... .......... ..MLRTNVLL LLVICLLDFF SSVKASVSYD    28
TBG5-ORF     1   ---------- ---------- ---------- ---------- ----------    50
TBG6-ORF     1   ---------- ---------- ---------- ---------- ----------    50
TBG7-ORF    -1   .MNTMSCLSS NFKFVFLAST VIWMTVMSSS LAAVDASNVT TIGTDSVTYD    49
apple      -21   .......... .......... .MGVGIQTMW SILLLFSCIF SAASASVSYD    29
carnation  -16   .......... ......MLCG KENNVMKMML VYVFVLITLI SCVYGNVWYD    34
asparagus  -20   .......... .......... MALKLVLMLM VALLAAVWSP PAVTASVTYD    30
broccoli   -20   .......... .......... MKMKQFNLLS LFLILITSFG SANSTIVSHD    30
Lupin      -12   .......... ..MFGSRIVM ESLMSRRNFH MVLLLLFFWV CYVTASVTYD    38

60         70         80         90        100
TBG1-ORF    27   HKAIIVNGQR KILISGSIHY PRSTPEMWPD LIQKAKEGGV DVIQTYVFWN    76
TBG2-ORF    37   NRALIIGGKR RMLISAGIHY PRATPEMWPT LIARSKEGGA DVIETYTFWN    86
TBG3-ORF    31   HRAIIVNGQR RILISGSVHY PRSTPEMWPG IIQKAKEGGV DVIQTYVFWN    80
TBG4-ORF    29   DRAIIINGKR KILISGSIHY PRSTPQMWPD LIQKAKDGGL DVIETYVFWN    78
TBG5-ORF    51   ---------- ---------- ---------- ---------- --IQTYVFWN   100
TBG6-ORF    51   ---------- ---------- ---------- ---------- --IQTYVFWN   100
TBG7-ORF    50   RRSLIINGQR KLLISASIHY PRSVPAMWPG LVRLAKEGGV DVIETYVFWN    99
apple       30   HKAIIINGQK RILISGSIHY PRSTPEMWPD LIQKAKDGGL DVIQTYVFWN    79
carnation   35   YRAIKINDQR RILLSGSIHY PRSTPEMWPD IIEKAKDSQL DVIQTYVFWN    84
asparagus   31   HKSVIINGQR RILISGSIHY PRSTPEMWPD LIQKAKDGGL DVIQTYVFWN    80
broccoli    31   ERAITIDGQR RILLSGSIHY PRSTSDMWPD LISKAKDGGL DTIETYVFWN    80
Lupin       39   HKAIMINGQR RILISGSIHY PRSTPQMWPD LIQKAKDGGL DVIETYVFWN    88

110        120        130        140        150
TBG1-ORF    77   GHEPEEGKYY FEERYDLVKF IKVVQEAGLY VHLRIGPYAC AEWNFGGFPV   126
TBG2-ORF    87   GHEPTRGQYN FEGRYDIVKF AKLVGSHGLF LFIRIGPYAC AEWNFGGFPI   136
TBG3-ORF    81   GHEPQQGKYY FEGRYDLVKF IKLVHQAGLY VHLRVGPYAC AEWNFGGFPV   130
TBG4-ORF    79   GHEPSPGKYN FEGRYDLVRF IKMVQRAGLY VNLRIGPYVC AEWNFGGFPV   128
TBG5-ORF   101   LHEPVRNQYD FEGRKDLINF VKLVERAGLF VHIRIGPYVC AEWNYGGFPL   150
TBG6-ORF   101   VHEPSPGNYN FEGRYDLVRF VKTIQKAGLY AHLRIGPYVC AEWNFGGFPV   150
TBG7-ORF   100   GHEPSPGNYY FGGRFDLVKF CKIIQQAGMY MILRIGPFVA AEWNFGGLPV   149
apple       80   GHEPSPGNYY FEERYDLVKF IKLVQQEGLF VNLRIGPYVC AEWNFGGFPV   129
carnation   85   GHEPSEGKYY FEGRYDLVKF IKLIHQAGLF VHLRIGPFAC AEWNFGGFPV   134
asparagus   81   GHEPSPGQYY FGGRYDLVRF LKLVKQAGLY AHLRIGPYVC AEWNFGGFPV   130
broccoli    81   AHEPSRRQYD FSGNLDLVRF IKTIQSAGLY SVLRIGPYVC AEWNYGGFPV   130
Lupin       89   GHEPSPGKYY FEDRFDLVGF IKLVQQAGLF VHLRIGPFIC AEWNFGGFPV   138
```

FIG. 3A

```
                    160        170        180        190        200
TBG1-ORF   127  WLKYVPGISF RTNNEPFKAA MQKFTTKIVD MMK-----AE KLYETQGGPI  176
TBG2-ORF   137  WLRDIPGIEF RTDNAPFKEE MERYVKKIVD LMI-----SE SLFSWQGGPI  186
TBG3-ORF   131  WLKYVPGISF RTDNGPFKAA MQKFTAKIVN MMK-----AE RLYETQGGPI  180
TBG4-ORF   129  WLKYVPGMEF RTNNQPFKVA MQGFVQKIVN MMK-----SE NLFESQGGPI  178
TBG5-ORF   151  WLHFIPGIEF RTDNEPFKAE MKRFTAKIVD MIK-----QE NLYASQGGPV  200
TBG6-ORF   151  WLKYVPGISF RADNEPFKNA MKGYAEKIVN LMKIIIFSSL RVVQSYSHRL  200
TBG7-ORF   150  WLHYVPGTTF RTDSEPFKYH MQKFMTYTVN LMK-----RE RLFASQGGPI  199
apple      130  WLKYVPGIAF RTDNEPFKAA MQKFTEKIVS MMK-----AE KLFQTQGGPI  179
carnation  135  WLKYVPGIEF RTDNGPFKEK MQVFTTKIVD MMK-----AE KLFHWQGGPI  184
asparagus  131  WLKYVPGIHF RTDNGPFKAA MGKFTEKIVS MMK-----AE GLYETQGGPI  180
broccoli   131  WLHNMPDMKF RTINPGFMNE MQNFTTKIVN MMK-----EE SLFASQGGPI  180
Lupin      139  WLKYVPGIAF RTDNEPFKEA MQKFTEKIVN IMK-----AE KLFQSQGGPI  188

210        220        230        240        250
TBG1-ORF   177  ILSQ-IENEY GP--MEWELG EPGKVYSEWA AKMAVDLGTG VPWIMCKQD-  226
TBG2-ORF   187  ILLQ-IENEY GN--VESSFG PKGKLYMKWA AEMAVGLGAG VPWVMCRQ-T  236
TBG3-ORF   181  ILSQ-IENEY GP--MEWELG APGKSYAQWA AKMAVGLDTG VPWVMCKQD-  230
TBG4-ORF   179  IMAQ-IENEY GP--VEWEIG APGKAYTKWA AQMAVGLKTG VPWIMCKQE-  228
TBG5-ORF   201  ILSQ-IENEY GNGDIESRYG PRAKPYVNWA ASMATSLNTG VPWVMCQQ-P  250
TBG6-ORF   201  RMSMGLKPRY ----LEHRDI SIQHGLQIWQ ----LDLNTG VPWVMCKEE-  250
TBG7-ORF   200  ILSQ-VENEY G--YYENAYG EGGKRYALWA AKMALSQNTG VPWIMC-QQY  249
apple      180  ILSQ-IENEF GP--VEWEIG APGKAYTKWA AQMAVGLDTG VPWIMCKQE-  229
carnation  185  ILNQ-IENEY GP--VEWEIG APGKAYTHWA AQMAQSLNAG VPWIMCKQDS  234
asparagus  181  ILSQ-IENEY GP--VEYYDG AAGKSYTNWA AKMAVGLNTG VPWVMCKQD-  230
broccoli   181  ILAQ-IENEY GN--VISSYG AEGKAYIDWC ANMANSLDIG VPWIMC-QQP  230
Lupin      189  ILSQ-IENEY GP--VEWEIG APGKAYTKWA AQMAVGLDTG VPWVMCKQE-  238

260        270        280        290        300
TBG1-ORF   227  DVPDPIINTC NGFYCDYFTP NKANKPKMWT EAWTAWFTEF GGPVPYRPAE  276
TBG2-ORF   237  DAPEYIIDTC NAYYCDGFTP NSEKKPKIWT ENWNGWFADW GERLPYRPSE  286
TBG3-ORF   231  DAPDPIINAC NGFYCDYFSP NKAYKPKIWT EAWTAWFTGF GNPVPYRPAE  280
TBG4-ORF   229  DAPDPVIDTC NGFYCEGFRP NKPYKPKMWT EVWTGWYTKF GGPIPQRPAE  278
TBG5-ORF   251  DAPPSVINTC NGFYCDQFKQ NSDKTPKMWT ENWTGWFLSF GGPVPYRPVE  300
TBG6-ORF   251  DAPDPVINTC NGFYCDNFFP NKPYKPAIWT EAWSGWFSEF GGPLHQRPVQ  300
TBG7-ORF   250  DAPDPVIDTC NSFYCDQFKP ISPNKPKIWT ENWPGWFKTF GARDPHRPAE  299
apple      230  DAPDPVIDTC NGFYCENFKP NKDYKPKMWT EVWTGWYTEF GGAVPTRPAE  279
carnation  235  DVPDNVIDTC NGFYCEGFVP KDKSKPKMWT ENWTGWYTEY GKPVPYRPAE  284
asparagus  231  DAPDPVINTC NGFYCDYFSP NKDNKPKMWT EAWTGWFTGF GGAVPQRPAE  280
broccoli   231  HAPQPMIETC NGFYCDQYKP SNPSSPKMWT ENWTGWFKNW GGKHPYRTAE  280
Lupin      239  DAPDPIIDTC NGFYCENFTP NKNYKPKLWT ENWTGWYTAF GGATPYRPAE  288
```

FIG. 3B

```
                         310        320        330        340        350
TBG1-ORF       277  DMAFAVARFI QTGGSFINYY MYHGGTNFGR TSGGPFIATS YDYDAPLDEF   326
TBG2-ORF       287  DIAFAIARFF QRGGSLQNYY MYFGGTNFGR TAGGPTQITS YDYDAPLDEY   336
TBG3-ORF       281  DLAFSVAKFI QKGGSFINYY MYHGGTNFGR TAGGPFIATS YDYDAPLDEY   330
TBG4-ORF       279  DIAFSVARFV QNNGSFFNYY MYHGGTNFGR TSSGLFIATS YDYDAPLDEY   328
TBG5-ORF       301  DIAFAVARFF QRGGTFQNYY MYHGGTNFGR TSGGPFIATS YDYDAPLDEY   350
TBG6-ORF       301  DLAFAVAQFI QRGGSFVNYY MYHGGTNFGR TAGGPFITTS YDYDAPLDEY   350
TBG7-ORF       300  DVAYSVARFF QKGGSVQNYY MYHGGTNFGR TAGGPFITTS YDYDAPIDEY   349
apple          280  DVAFSVARFI QSGGSFLNYY MYHGGTNFGR TAGGPFMATS YDYDAPLDEY   329
carnation      285  DVAFSVARFI QNGGSFMNYY MFHGGTNFE- TTAGRFVSTS YDYDAPLDEY   334
asparagus      281  DMAFAVARFI QKGGSFINYY MYHGGTNFGR TAGGPFISTS YDYDAPIDEY   330
broccoli       281  DLAFSVARFF QTGGTFQNYY MYHGGTNFGR VAGGPYITTS YDYDAPLDEY   330
Lupin          289  DIAFSVARFI QNRGSLFNYY MYHGGTNFGR TSNGLFVATS YDYDAPIDEY   338

360        370        380        390        400
TBG1-ORF       327  GSLRQPKWGH LKDLHRAIKL CEPALVSVD- PTVTSLGNYQ EARVFKSES-   376
TBG2-ORF       337  GLLRQPKWGH LKDLHAAIKL CEPALVAADS PQYIKLGPKQ EAHVYRGTSN   386
TBG3-ORF       331  GLLRQPKWGH LKDLHRAIKL CEPALVSGD- PAVTALGHQQ EAHVFRSKA-   380
TBG4-ORF       329  GLLNEPKYGH LRDLHKAIKL SEPALVSSY- AAVTSLGSNQ EAHVYRSKS-   378
TBG5-ORF       351  ---------- ---------- ---------- ---------- ----------   400
TBG6-ORF       351  ---------- ---------- ---------- ---------- ----------   400
TBG7-ORF       350  GLPRFPKWGH LKELHKVIKS CEHALLNND- PTLLSLGPLQ EADVYEDAS-   399
apple          330  GLPREPKWGH LRDLHKAIKS CESALVSVD- PSVTKLGSNQ EAHVFKSES-   379
carnation      335  GLPREPKYTH LKNLHKAIKM CEPALVSSD- AKVTNLGSNQ EAHVYSSNS-   384
asparagus      331  GLLRQPKWGH LRDLHKAIKL CEPALVSGE- PTITSLGQNQ ESYVYRSKS-   380
broccoli       331  GNLNQPKWGH LKQLHTLLKS MEKPLTYGNI STID-LGNSV TATVYSTNEK   380
Lupin          339  GLLNEPKWGH LRELHRAIKQ CESALVSVD- PTVSWPGKNL EVHLYKTES-   388

410        420        430        440        450
TBG1-ORF       377  ---------- GACAAFLANY NQHSFAKVAF GNMHYNLPPW SISILPDCKN   426
TBG2-ORF       387  NIGQYMSLNE GICAAFIANI DEHESATVKF YGQEFTLPPW SVVF---CQI   436
TBG3-ORF       381  ---------- GSCAAFLANY DQHSFATVSF ANRHYNLPPW SISILPDCKN   430
TBG4-ORF       379  ---------- GACAAFLSNY DSRYSVKVTF QNRPYNLPPW SISILPDCKT   428
TBG5-ORF       401  ---------- ---------- ---------- ---------- ----------   450
TBG6-ORF       401  ---------- ---------- ---------- ---------- ----------   450
TBG7-ORF       400  ---------- GACAAFLANM DDKNDKVVQF RHVSYHLPAW SVSILPDCKN   449
apple          380  ---------- D-CAAFLANY DAKYSVKVSF GGGQYDLPPW SISILPDCKT   429
carnation      385  ---------- GSCAAFLANY DPKWSVKVTF SGMEFELPAW SISILPDCKK   434
asparagus      381  ---------- -SCAAFLANF NSRYYATVTF NGMHYNLPPW SVSILPDCKT   430
broccoli       381  S--------- -SC--FIGNV NATADALVNF KGKDYNVPAW SVSVLPDCDK   430
Lupin          389  ---------- A-CAAFLANY NTDYSTQVKF GNGQYDLPPW SISILPDCKT   438
```

FIG. 3C

```
                    460        470        480        490        500
TBG1-ORF    427  TVYNTARVGA QSAQM--K-- ---------- -------MTP VSRGFS--WE  476
TBG2-ORF    437  AEIQLSTQLR WGHKLQSKQW AQILFQLGII LCFYKLSLKA SSESFSQSWM  486
TBG3-ORF    431  TVFNTARIGA QSAQM--K-- ---------- -------MTP VSRGLP--WQ  480
TBG4-ORF    429  AVYNTAQVNS QSSSI--K-- ---------- -------MTP AGGGLS--WQ  478
TBG5-ORF    451  ---------- ---------- ---------- ---------- ----------  500
TBG6-ORF    451  ---------- ---------- ---------- ---------- ----------  500
TBG7-ORF    450  VAFNTAKVGC QTSIVNMAP- --------ID L--HPTASSP KRDIKSLQWE  499
apple       430  EVYNTAKVGS QSSQV--Q-- ---------- -------MTP VHSGFP--WQ  479
carnation   435  EVYNTARVNE PSPKLHSK-- ---------- -------MTP VISNLN--WQ  484
asparagus   431  TVFNTARVGA QTTTM--K-- ---------- -------MQY LG-GFS--WK  480
broccoli    431  EAYNTARVNT QTSIITEDS- ---------- -C-------D EPEKLKWTWR  480
Lupin       439  EVFNTAKVNS PRLHR--K-- ---------- -------MTP VNSAFA--WQ  488

510        520        530        540        550
TBG1-ORF    477  S-FNEDAASH EDD-TFTVVG LLEQINITRD VSDYLWYMTD IEIDPTE-GF  526
TBG2-ORF    487  T-LKEPLGVW GDKN-FTSKG ILEHLNVTKD QSDYLWYLTR IYISDDDISF  536
TBG3-ORF    481  S-FNEETSSY EDS-SFTVVG LLEQINTTRD VSDYLWYSTD VKIDSRE-KF  530
TBG4-ORF    479  S-YNEETPTA DDSDTLTANG LWEQKNVTRD SSDYLWYMTN VNIASNE-GF  528
TBG5-ORF    501  ---------- ---------- ---------- ---------- ----------  550
TBG6-ORF    501  ---------- ---------- ---------- ---------- ----------  550
TBG7-ORF    500  V-FKETAGVW GVAD-FTKNG FVDHINTTKD ATDYLWYTTS IFVHAEE-DF  549
apple       480  S-FIEETTSS DETDTTTLDG LYEQINITRD TTDYLWYMTD ITIGSDE-AF  529
carnation   485  S-YSDEVPTA DSPGTFREKK LYEQINMTWD KSDYLWYMTD VVLDGNE-GF  534
asparagus   481  A-YTEDTDAL NDN-TFTKDG LVEQLSTTWD RSDYLWYTTY VDIAKNE-EF  530
broccoli    481  PEFTTQKTIL KGSGDLIAKG LVDQKDVTND ASDYLWYMTR VHLDKKDPIW  530
Lupin       489  S-YNEEPASS SENDPVTGYA LWEQVGVTRD SSDYLWYLTD VNIGPND---  538

560        570        580        590        600
TBG1-ORF    527  LNSGN-WPWL TVFSAGHALH VFVNGQLAGT VYGSLENPKL TFSNGINLRA  576
TBG2-ORF    537  WEENDVSPTI DIDSMRDFVR IFVNGQLAGS VKGKW----I KVVQPVKLVQ  586
TBG3-ORF    531  LRGGK-WPWL TIMSAGHALH VFVNGQLAGT AYGSLEKPKL TFSKAVNLRA  580
TBG4-ORF    529  LKNGK-DPYL TVMSAGHVLH VFVNGKLSGT VYGTLDNPKL TYSGNVKLRA  578
TBG5-ORF    551  ---------- ---------- ---------- ---------- ----------  600
TBG6-ORF    551  ---------- ---------- ---------- ---------- ----------  600
TBG7-ORF    550  LRN-RGTAML FVESKGHAMH VFINKKLQAS ASGNGTVPQF KFGTPIALKA  599
apple       530  LKNGK-SPLL TIFSAGHALN VFINGQLSGT VYGSLENPKL SFSQNVNLRS  579
carnation   535  LKKGD-EPWL TVNSAGHVLH VFVNGQLQGH AYGSLAKPQL TFSQKVKMTA  584
asparagus   531  LKTGK-YPYL TVMSAGHAVH VFINGQLSGT AYGSLDNPKL TYSGSAKLWA  580
broccoli    531  SRNMS----L RVHSNAHVLH AYVNGKYVGN QIVRDNKFDY RFEKKVNLVH  580
Lupin       539  IKDGK-WPVL TAMSAGHVLN VFINGQYAGT AYGSLDDPRL TFSQSVNLRV  588
```

FIG. 3D

```
                   610        620        630        640        650
TBG1-ORF    577  GVNKISLLSI AVGLPNVGPH FETWNAGVLG PVSLNGLNEG T---RDLTWQ  626
TBG2-ORF    587  GYNDILLLSE TVGLQNYGAF LEKDGAGFKG QIKLTGCKSG D---INLTTS  636
TBG3-ORF    581  GVNKISLLSI AVGLPNIGPH FETWNAGVLG PVSLTGLDEG K---RDLTWQ  630
TBG4-ORF    579  GINKISLLSV SVGLPNVGVH YDTWNAGVLG PVTLSGLNEG S---RNLAKQ  628
TBG5-ORF    601  ---------- ---------- ---------- ---------- ----------  650
TBG6-ORF    601  ---------- ---------- ---------- ---------- ----------  650
TBG7-ORF    600  GKNEISLLSM TVGLQTAGAF YE-WIGAGPT SVKVAGFKTG T---MDLTAS  649
apple       580  GINKLALLSI SVGLPNVGTH FETWNAGVLG PITLKGLNSG T---WDMSGW  629
carnation   585  GVNRISLLSA VVGLANVGWH FERYNQGVLG PVTLSGLNEG T---RDLTWQ  634
asparagus   581  GSNKISILSV SVGLPNVGNH FETWNTGVLG PVTLTGLNEG K---RDLSLQ  630
broccoli    581  GTNHLALLSV SVGLQNYGPF FESGPTGING PVKLVGYKGD ETIEKDLSKH  630
Lupin       589  GNNKISLLSV SVGLANVGTH FETWNTGVLG PVTLTGLSSG T---WDLSKQ  638

660        670        680        690        700
TBG1-ORF    627  KWFYKVGLKG EALSLHSLSG SPSVE--WVE GSLVAQKQPL SWYKTTFNAP  676
TBG2-ORF    637  LWTYQVGLRG EFLEVYDVNS TESAG--WTE FPTGTTPSVF SWYKTKFDAP  686
TBG3-ORF    631  KWSYKVGLKG EALSLHSLSG SSSVE--WVE GSLVAQRQPL TWYKSTFNAP  680
TBG4-ORF    629  KWSYKVGLKG ESLSLHSLSG SSSVE--WVR GSLMAQKQPL TWYKATFNAP  678
TBG5-ORF    651  ---------- ---------- ---------- ---------- ----------  700
TBG6-ORF    651  ---------- ---------- ---------- ---------- ----------  700
TBG7-ORF    650  AWTYKIGLQG EHLRIQKSYN LKSKI--WAP TSQPPKQQPL TWYKAVVDAP  699
apple       630  KWTYKTGLKG EALGLHTVTG SSSVE--WVE GPSMAEKQPL TWYKATFNAP  679
carnation   635  YWSYKIGTKG EEQQVYNSGG SSHVQ--WGP PAW---KQPL VWYKTTFDAP  684
asparagus   631  KWTYQIGLHG ETLSLHSLTG SSNVE--WGE AS---QKQPL TWYKTFFNAP  680
broccoli    631  QWDYKIGLNG FNHKLFSMKS AGHHHRKWST EKLPADRM-L SWYKANFKAP  680
Lupin       639  KWSYKIGLKG ESLSLHTEAG SNSVE--WVQ GSLVAKKQPL AWYKTTFSAP  688

710        720        730        740        750
TBG1-ORF    677  DGNEPLALDM NTMGKGQVWI NGQSLGRHWP AYKSS-GSCS V-CNYTGWFD  726
TBG2-ORF    687  GGTDPVALDF SSMGKGQAWV NGHHVGRYWT LVAPN-NGCG RTCDYRGAYH  736
TBG3-ORF    681  AGNDPLALDL NTMGKGQVWI NGQSLGRYWP GYKAS-GNCG A-CNYAGWFN  730
TBG4-ORF    679  GGNDPLALDM ASMGKGQIWI NGEGVGRHWP GYIAQ-GDCS K-CSYAGTFN  728
TBG5-ORF    701  ---------- ---------- ---------- ---------- ----------  750
TBG6-ORF    701  ---------- ---------- ---------- ---------- ----------  750
TBG7-ORF    700  PGNEPVALDM IHMGKGMAWL NGQEIGRYWP RRTSKYENCV TQCDYRGKFN  749
apple       680  PGDAPLALDM GSMGKGQIWI NGQSVGRHWP GYIAR-GSCG D-CSYAGTYD  729
carnation   685  GGNDPLALDL GSMGKGQAWI NGQSIGRHWS NNIAK-GSCN DNCYAGTYT  734
asparagus   681  PGNEPLALDM NTMGKGQIWI NGQSIGRYWP AYKAS-GSCG S-CDYRGTYN  730
broccoli    681  LGKDPVIVDL NGLKGEVWI NGQSIGRYWP SFNSSDEGCT EECDYRGEYG  730
Lupin       689  AGNDPLALDL GSMGKGEVWV NGQSIGRHWP GNKAR-GNCG N-CNYAGTYT  738
```

FIG. 3E

```
                        760        770        780        790        800
TBG1-ORF   727  EKKCLTNCGE GSQRWYHVPR SWLYPTGNLL V-VFEEWGGD PYGITLVKRE  776
TBG2-ORF   737  SDKCRTNCGE ITQAWYHIPR SWLKTLNNVL V-IFEETDKT PFDISISTRS  786
TBG3-ORF   731  EKKCLSNCGE ASQRWYHVPR SWLYPTGNLL V-LFEEWGGE PHGISLVKRE  780
TBG4-ORF   729  EKKCQTNCGQ PSQRWYHVPR SWLKPSGNLL V-VFEEWGGN PTGISLVRRS  778
TBG5-ORF   751  ---------- ---------- ---------- ---------- ----------  800
TBG6-ORF   751  ---------- ---------- ---------- ---------- ----------  800
TBG7-ORF   750  PDKCVTGCGQ PTQRWYHVPR SWFKPSGNVL I-IFEEIGGD PSQIRFSMRK  799
apple      730  DKKCRTHCGE PSQRWYHIPR SWLTPTGNLL V-VFEEWGGD PSRISLVERG  779
carnation  735  ETKCLSDCGK SSQKWYHVPR SWLQPRGNLL V-VFEEWGGD TKWVSLVKRT  784
asparagus  731  EKKCLSNCGE ASQRWYHVPR SWLIPTGNFL V-VLEEWGGD PTGISMVKRS  780
broccoli   731  SDKCAFMCGK PTQRWYHVPR SFLNDKGHNT ITLFEEMGGD PSMVKFKTVV  780
Lupin      739  DTKCLANCGQ PSQRWYHVPR SWLRSGGNYL V-VLEEWGGD PNGIALVERT  788

810        820        830        840        850
TBG1-ORF   777  IGSVCADIYE WQ-PQLLNWQ RLVSGKFDRP LR--PKAHLK CAPGQKISSI  826
TBG2-ORF   787  TETICAQVSE KHYPPLHKWS HSEFDRKLSL MDKTPEMHLQ CDEGHTISSI  836
TBG3-ORF   781  VASVCADINE WQ-PQLVNWQ MQASGKVDKP LR--PKAHLS CASGQKITSI  830
TBG4-ORF   779  ---------- ---------- --------R- ---------- ----------  828
TBG5-ORF   801  ---------- ---------- ---------- ---------- ----------  850
TBG6-ORF   801  ---------- ---------- ---------- ---------- ----------  850
TBG7-ORF   800  VSGACGHLSV -DHPSFD--V ENLQGSEIEN DKNRPTLSLK CPTNTNISSV  849
apple      780  ---------- ---------- --------TA LD--AK---- ----------  829
carnation  785  IA-------- ---------- ---------- ---------- ----------  834
asparagus  781  VASVCAEVEE LQ-PTMDNWR TKAYG----- -R--PKVHLS CDPGQKMSKI  830
broccoli   781  TGRVCAKAHE ---------- ---------- ---HNKVELS CN-NRPISAV  830
Lupin      789  ---------- ---------- ---------- ---------- ----------  838

860        870        880        890        900
TBG1-ORF   827  KFASFGTPEG VCGNFQQGSC HAPRSYDAFK K-----NCVG KESCSVQVTP  876
TBG2-ORF   837  EFASYGSPNG SCQKFSQGKC HAANSLSV-- ---VSQACIG RTSCSIGISN  886
TBG3-ORF   831  KFASFGTPQG VCGSFREGSC HAFHSYDAFE R-----YCIG QNSCSVPVTP  880
TBG4-ORF   829  ---------- ---------- ---------- ---------- ----------  878
TBG5-ORF   851  ---------- ---------- ---------- ---------- ----------  900
TBG6-ORF   851  ---------- ---------- ---------- ---------- ----------  900
TBG7-ORF   850  KFASFGNPNG TCGSYMLGDC HDQNSAALVE K-----VCLN QNECALEMSS  899
apple      830  ---------- ---------- ---------- ---------- ----------  879
carnation  835  ---------- ---------- ---------- ---------- ----------  884
asparagus  831  KFASFGTPQG TCGSFSEGSC HAHKSYDAFE QEGLMQNCVG QEFCSVNVAP  880
broccoli   831  KFASFGNPSG QCGSFAAGSC EGAKDAVKV- ---VAKECVG KLNCTMNVSS  880
Lupin      839  ---------- ---------- ---------- ---------- ----------  888
```

FIG. 3F

```
              910        920        930        940        950
TBG1-ORF  877 ENFGGDP-CR NVLKKLSVEA ICS------- ----...... ..........  926
TBG2-ORF  887 GVFG-DP-CR HVVKSLAVQA KCSPPPDLST SASS...... ..........  936
TBG3-ORF  881 EIFGGDP-CP HVMKKLSVEV ICS------- ----...... ..........  930
TBG4-ORF  879 ---------- ---------- ---------- ----...... ..........  928
TBG5-ORF  901 ---------- ---------- ---------- ----...... ..........  950
TBG6-ORF  901 ---------- ---------- ---------- ----...... ..........  950
TBG7-ORF  900 ANFNMQL-CP STVKKLAVEV NCS------- ----...... ..........  949
apple     880 ---------- ----KL---- ---------- ----...... ..........  929
carnation 885 ---------- ---------- ---------- ----...... ..........  934
asparagus 881 EVFGGDP-CP GTMKKLAVEA ICE------- ----...... ..........  930
broccoli  881 HKFGSNLDCG DSPKRLFVEV EC-------- ----...... ..........  930
```

FIG. 3G

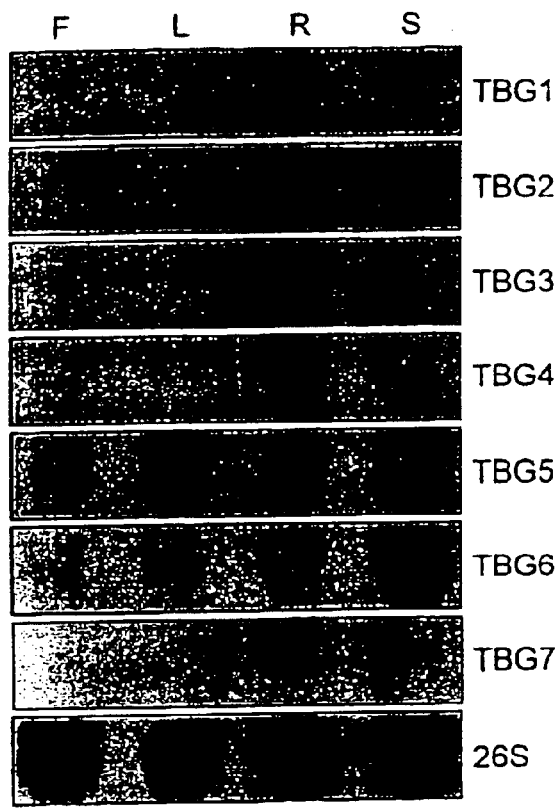

Figure 4. Autoradiograph of northern blot analysis of TBG expression in various plant tissues. Twenty μg of total RNA extracted from flowers (F), leaves (L), roots (R) and stems (S) was loaded in each lane. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control for each blot and one example is shown.

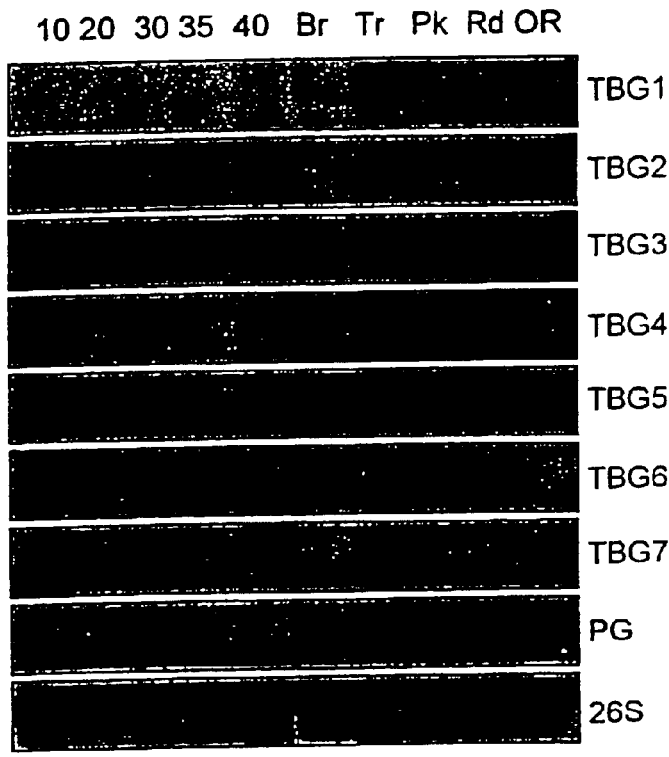

Figure 5. Autoradiograph of northern blot analysis of TBG expression in fruit tissues. Twenty μg of total RNA extracted from peel and outer pericarp tissue was loaded in each lane. Fruit were harvested at 10, 20, 30, 35, and 40 days post-pollenation and at the breaker (Br), turning (Tr), pink (Pk), red (Rd) and over ripe (OR) stages. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control for each blot and one example is shown. A cDNA clone for tomato polygalacturonase (PG) was also used as a probe to show a well characterized, fruit-ripening-specific control.

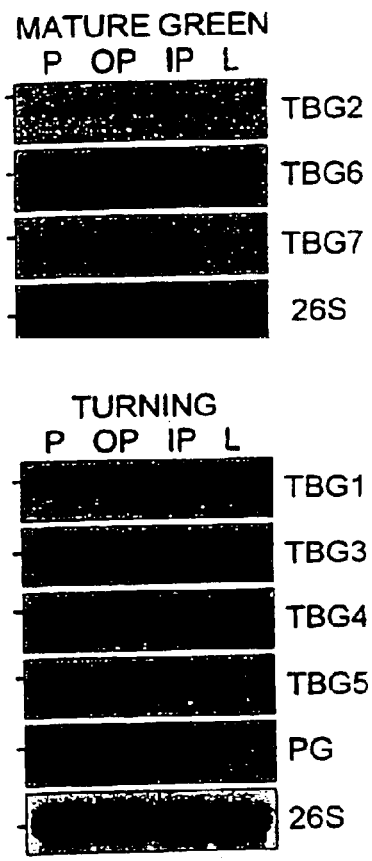

Figure 6. Autoradiograph of northern blot analysis of TBG expression in fruit tissues. Twenty μg of total RNA extracted from mature green or turning stage fruit peel (P), outer pericarp (OP), inner pericarp (IP) and locular (L) tissue was loaded in each lane. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control for each blot and one example is shown. A cDNA clone for tomato polygalacturonase (PG) was also used as a probe to show a well characterized, fruit-ripening-specific control.

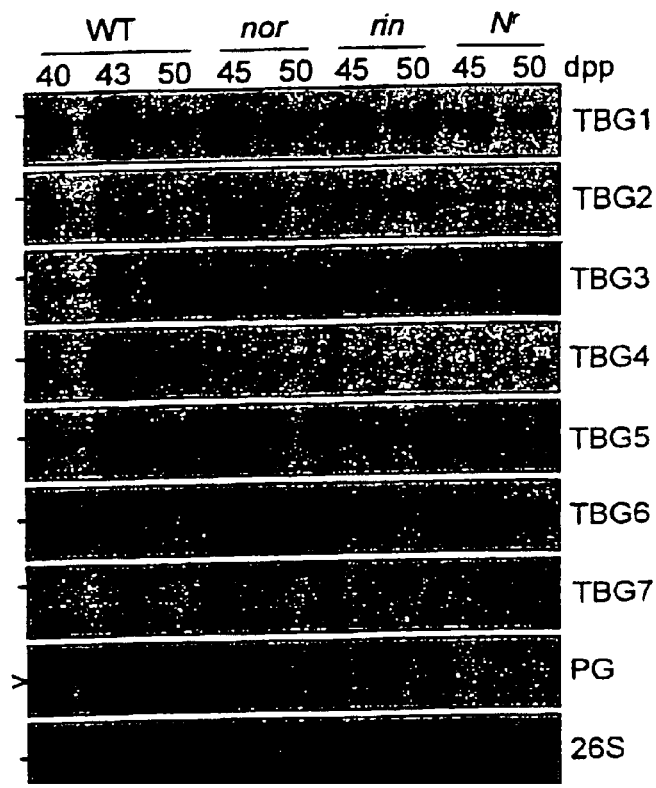

Figure 7. Autoradiograph of northern blot analysis of TBG expression in normal and mutant fruit tissues. Twenty μg of total RNA extracted from peel and outer pericarp tissue at various days post-pollination (dpp) was loaded in each lane. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control for each blot and one example is shown. A cDNA clone for tomato polygalacturonase (PG) was also used as a probe to show a well characterized, fruit-ripening-specific control. The - and > marks on the left indicate the position of the tomato 27S and 18S rRNAs respectively.

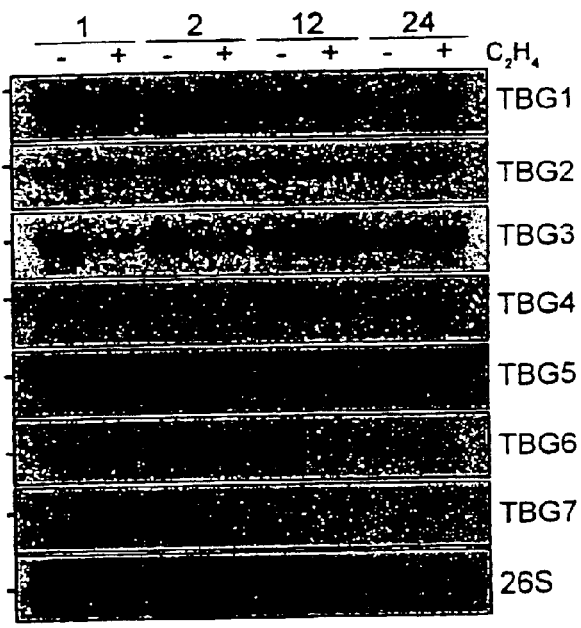

Figure 8. Autoradiograph of northern blot analysis of TBG expression in response to ethylene treatment of mature green fruit tissues. Twenty µg of total RNA extracted from peel and outer pericarp tissue at various times (1, 2, 12 and 24 hours) after treatment with (+) or without (-) 10 ppm ethylene was loaded in each lane. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control for each blot and one example is shown. The - marks on the left indicate the position of the tomato 27S rRNA.

Figure 9. Western blot analysis of TBG4 expression by yeast. A yeast clone was isolated that secreted high levels of FLAG-TBG4 fusion protein into the culture medium. Protein samples were separated in an 8% acrylamide gel, transferred to nitrocellulose and were blotted with M1 anti-FLAG primary antibody. Blots were washed and blotted with an alkaline-phosphatase conjugated secondary antibody and alkaline phosphatase activity was detected using Sigma Fast substrate. Lane 1, culture medium of an untransformed yeast clone was used as a negative control. Lane 2, culture medium of yeast clone expressing FLAG-TBG4 fusion protein. Lane 3, Affinity purified FLAG-TBG4 fusion protein.

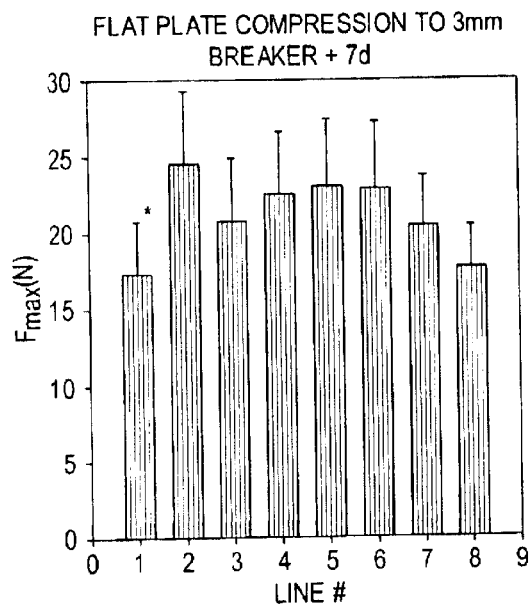
FIG. 11E(1)
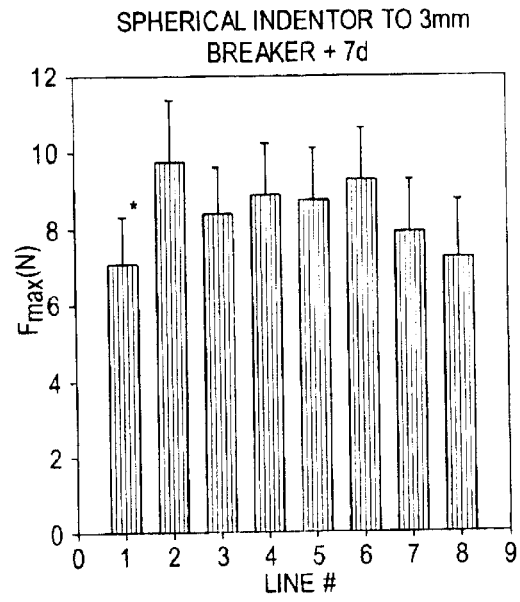
FIG. 11E(2)
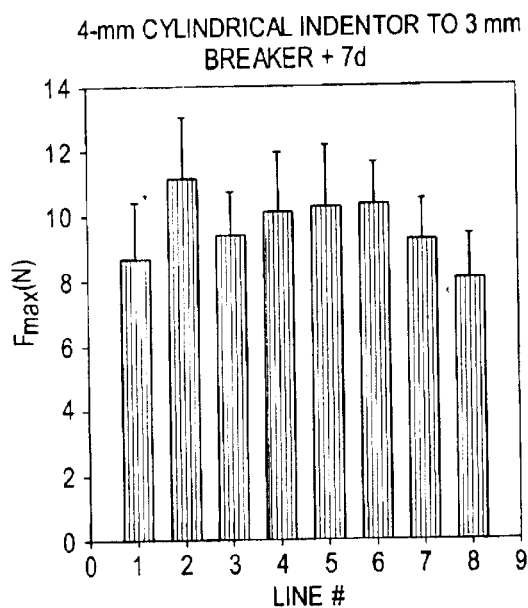
FIG. 11E(3)
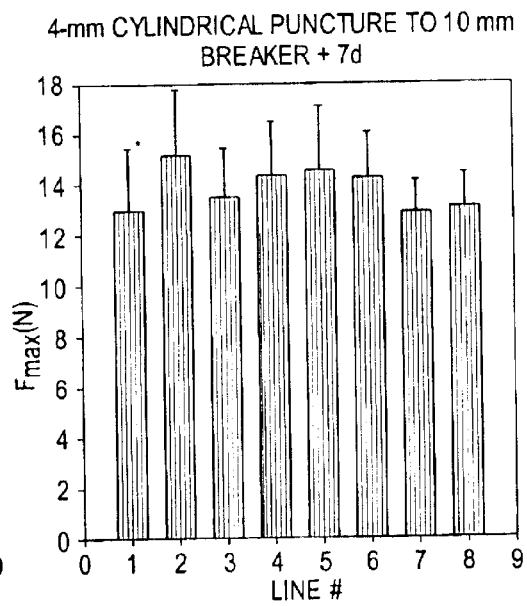
FIG. 11E(4)

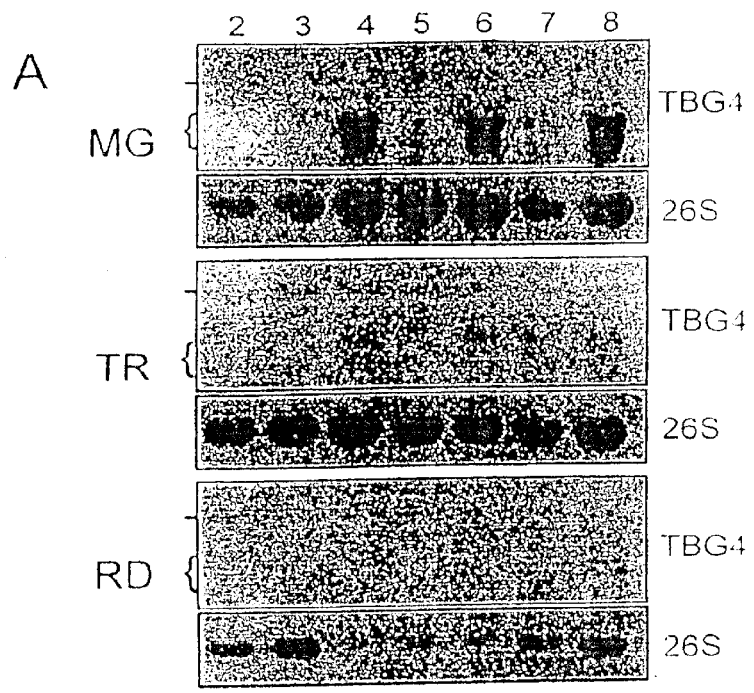

FIG. 12A

Figure 12. Northern blot analysis of TBG4 expression in transgenic fruit containing TBG4 antisense construct. A. Total RNA was extracted from mature green/42 days post-pollenation (MG), turning/breaker + 3 (TR) and red/breaker + 7 (RD) fruit and twenty μg was loaded in each lane. RNAs were separated in an agarose gel and transferred to nylon membrane. Blots were hybridized using the probes indicated to the right, washed to a final stringency of 0.1X SSC at 65°C and were used to expose x-ray film. A 26S ribosomal gene clone from soybean was used as a loading control. The marks - and { denote the positions of the endogenous TBG4 and antisense mRNAs respectively. Lanes 2-8 correspond to transgenic lines 2-8 in Figures 11A-E.

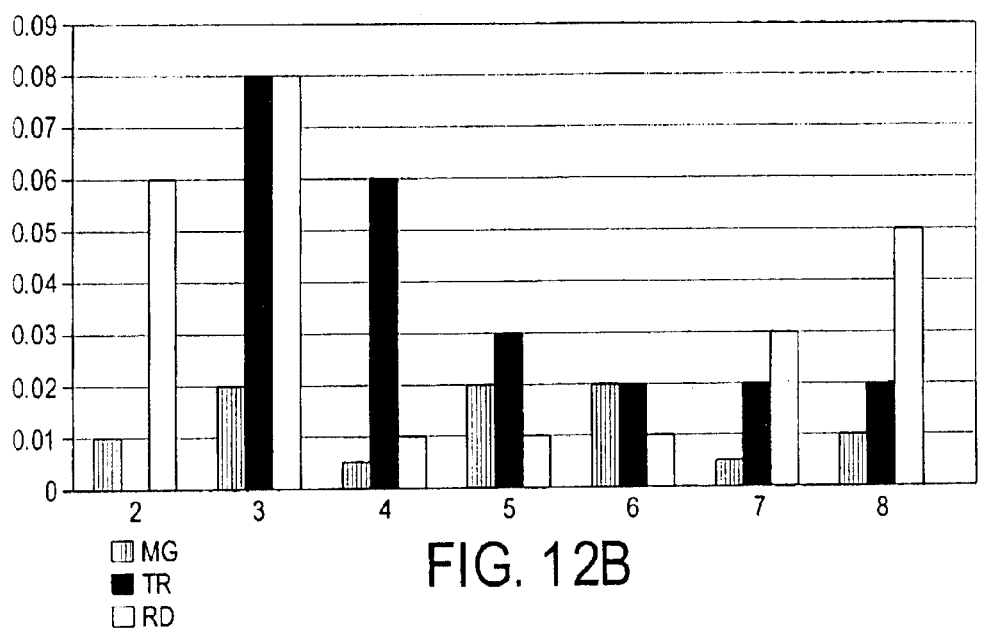
Figure 12. Northern blot analysis of TBG4 expression in transgenic fruit containing TBG4 antisense construct.
B. Chart of TBG4
mRNA levels in lines 2-8. Autoradiographs were scanned using a densitometer and TBG4 mRNA levels were corrected against the loading controls. TBG4 mRNA levels are shown in arbitrary units.

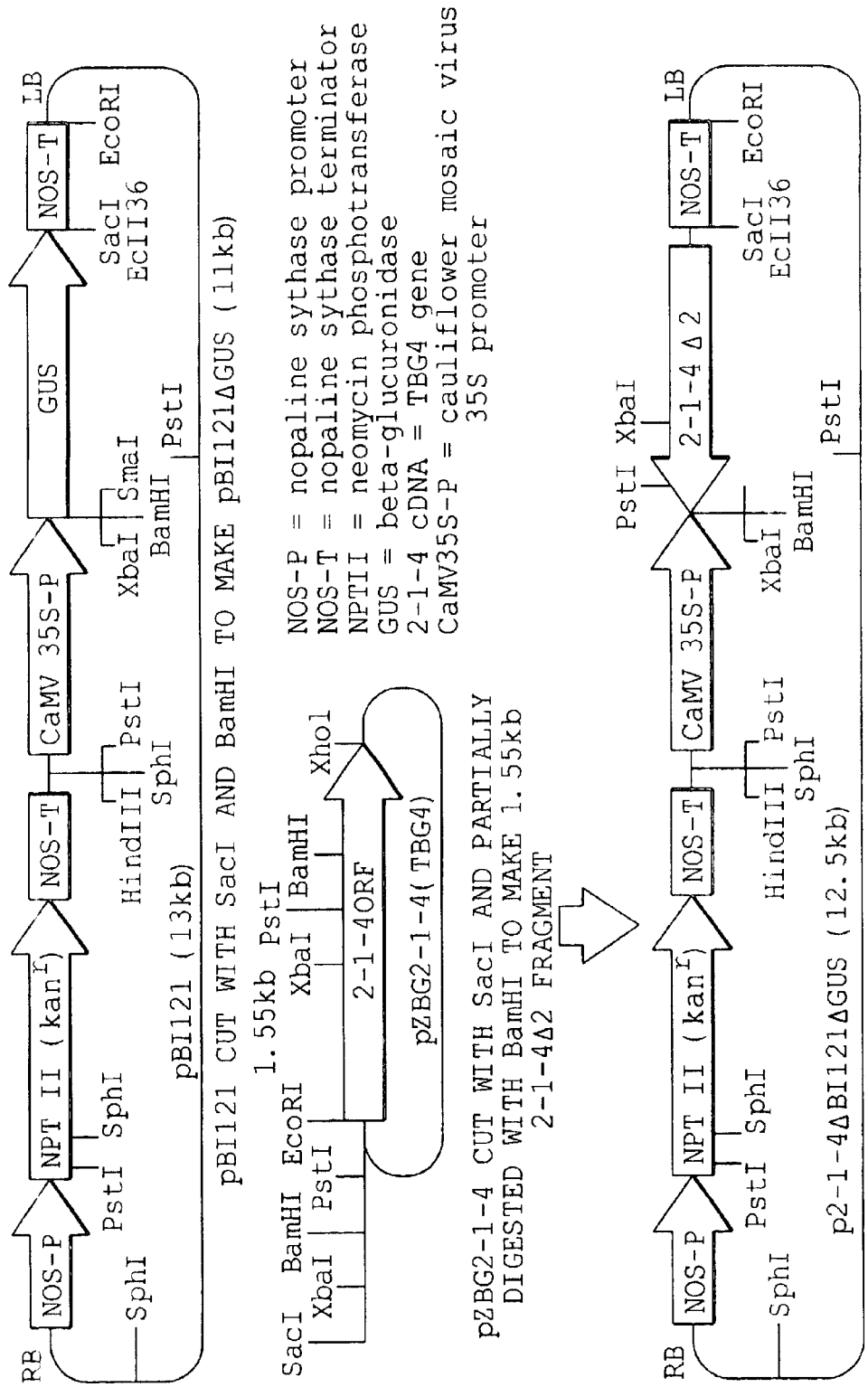
FIG. 13 BINARY CONSTRUCT USED TO TRANSFORM PLANTS AND EXPRESS TBG4 (pZBG2-1-4 IN THE ANTISENSE ORIENTATION

GENES CODING FOR TOMATO β-GALACTOSIDASE POLYPEPTIDES

This application claims the benefit of provisional application Ser. No. 60/088,805 filed Jun. 9, 1998.

FIELD OF THE INVENTION

The present invention relates to a family of novel plant genes encoding polypeptides characterized by their ability to hydrolyze terminal non-reducing β-D-galactosyl residues from β-D-galactosides. More specifically, a polynucleotide sequence derived from a cDNA clone designated pZBG2-1-4 (referred to in U.S. Provisional Appln. No. 60/088,805 as pTomβgal 4), which encodes a specific plant polypeptide named β-galactosidase II, is provided. Also provided are cDNA clones encoding six other homologous polypeptides, methods of using these cDNA clones for producing β-D-galactoside polypeptides of the invention, and methods of modifying fruit quality by employment of a polynucleotide or polypeptide of the present invention.

BACKGROUND OF THE INVENTION

The most conspicuous and important processes related to post-harvest quality of climacteric fruit are the changes in texture, color, taste, and aroma which occur during ripening. Because of the critical relationship that deleterious changes in texture have to quality and post-harvest shelf-life, emphasis has been placed on studying the mechanisms involved in the loss of firmness that occurs-during tomato fruit ripening. Although fruit softening may involve changes in turgor pressure, anatomical characteristics and cell wall integrity, it is generally assumed that cell wall disassembly leading to a loss of wall integrity is a critical feature. The most apparent changes, in terms of composition and size, occur in the pectic fraction of the cell wall (see references in Seymour and Gross, 1996).

Changes known to occur in the pectic fraction of the cell wall during fruit ripening include increased solubility, depolymerization, de-esterification and a significant net loss of neutral sugar containing side chains (Huber, 1983; Fischer and Bennett, 1991; Seymour and Gross, 1996). The best characterized pectin-modifying enzymes are polygalacturonase (endo-α1→4-D-galacturonan hydrolase; E.C. 3.2.1.15; PG) and pectin methylesterase (E.C. 3.1.1.11; PME). Although PG and PME are relatively abundant and have substantial activity during tomato fruit ripening, softening still occurs, albeit with a slight delay, in fruit where PG (Smith et al. 1988, 1990) or PME (Tieman et al. 1992; Hall et al. 1993) gene expression and enzyme activity was significantly down-regulated in transgenic plants. Moreover, over-expression of PG in non-ripening mutant rin tomato fruit did not result in softening even though depolymerization and solubilization of pectin was evident (Giovannoni et al., 1989).

Among the other known pectin modifications that occur during fruit development, one of the best characterized is the significant net loss of galactosyl residues which occurs in the cell walls of many ripening fruit (Gross and Sams, 1984; Seymour and Gross, 1996). Although some loss of galactosyl residues could result indirectly from the action of PG, β-galactosidase (exo-β(1→4)-D-galactopyranoside; E.C. 3.2.1.23) is the only enzyme identified in higher plants capable of directly cleaving β(1→4)galactan bonds, and probably plays a role in galactan sidechain loss (DeVeau et al., 1993; Carey et al., 1995; Carrington and Pressey, 1996). No endo-acting galactanase has yet been identified in higher plants. The view that β-galactosidase is active in releasing galactosyl residues from the cell wall during ripening is supported by the dramatic increase in free galactose, a product of β-galactosidase activity (Gross, 1984) and a concomitant increase in activity of a particular enzyme, designated β-galactosidase II, in tomatoes during ripening (Carey et al., 1995). β-galactosidase activity is thought to be important in cell wall metabolism (Carey et al., 1995). β-Galactosidases are generally assayed using artificial substrates such as p-nitrophenyl-β-D-galactopyranoside (PNP), 4-methylumbelliferyl-β-D-galactopyranoside and 5-bromo-4-chloro-3-indoxyl-β-D-galactopyranoside (X-GAL). However, it is clear that β-galactosidase II is also active against natural substrates, i.e., β(1→4)galactan (Carey et al., 1995; Carrington and Pressey, 1996; Pressey, 1983). β-Galactosidase proteins have been purified and characterized in a number of other fruits including kiwifruits (Ross et al., 1993), coffee (Golden et al., 1993), persimmon (Kang et al., 1994), and apple (Ross et al., 1994).

Carey et al. (1995) were able to purify three previously identified β-galactosidases from ripening tomato fruit (Pressey, 1983), but only one (β-galactosidase II) was active against β(1→4)galactan. Even though they were able to identify putative β-galactosidase cDNA clones, none of the cDNA's deduced amino acid sequences matched the amino terminal sequence of the β-galactosidase II protein. Although β-galactosidase II, a protein present in tomato (*Lycopersicon esculentum* Mill.) fruit during ripening and capable of degrading tomato fruit galactan has been purified, cloning of the corresponding gene has been elusive.

The modification of plant gene expression has been achieved by several methods. The molecular biologist can choose from a range of known methods to decrease or increase gene expression or to alter the spatial or temporal expression of a particular gene. For example, the expression of either specific antisense RNA or partial (truncated) sense RNA has been utilized to reduce the expression of various target genes in plants (as reviewed by Bird and Ray, 1991, Biotechnology and Genetic-Engineering Reviews 9:207–227). These techniques involve the incorporation into the genome of the plant of a synthetic gene designed to express either antisense or sense RNA. They have been successfully used to down-regulate the expression of a range of individual genes involved in the development and ripening of tomato fruit (Gray et al, 1992, Plant Molecular Biology, i9:69–87). Methods to increase the expression of a target gene have also been developed. For example, additional genes designed to express RNA containing the complete coding region of the target gene may be incorporated into the genome of the plant to "over-express" the gene product. Various other methods to modify gene expression are known; for example, the use of alternative regulatory sequences. The complete disclosure of each of the references cited above is fully incorporated herein by reference.

The need therefore exists to clone a gene for β-galactosidase II and related polypeptides, and using known methods of modification of plant gene expression, thereby to provide methods for modifying quality of fruits, particularly by modifying the cell wall, thereby directly affecting the ripening of the fruit;

SUMMARY OF THE INVENTION

The present invention is based on the discovery of novel DNA sequences derived from cDNA clones from a family of genes encoding β-galactosidases. The phylogenic tree based on the shared amino acid sequence identities for the DNA sequences of the present invention is shown in FIGS. 1A,B. Five cDNA and two RT-PCR clones, designated herein as TBG1, TBG2, TBG3, TBG4, TBG5, TBG6, and TBG7 and having the nucleic acid sequences designated SEQ ID NOs 1–7, respectively as shown in FIG. 2, were identified which had a high degree of shared sequence identity to other known β-galactosidases. The corresponding amino acid sequences are designated herein as SEQ ID NOs 8–16, respectively and are shown in FIGS. 2 and 3. The nucleotide sequences for SEQ ID NOs 1–7 are recorded in Gen Bank with the following respective Accessions Numbers:

| SEQ ID NO:1 | TGB1 | AF023847 | deposit Sep. 10, 1997 |
| SEQ ID NO:2 | TGB2 | AF154420 | deposited May 19, 1999 |
| SEQ ID NO:3 | TGB3 | AF154421 | deposited May 20, 1999 |
| SEQ ID NO:4 | TGB4 | AF020390 | deposited Aug. 21, 1997 |
| SEQ ID NO:5 | TGB5 | AF154423 | deposited May 20, 1999 |
| SEQ ID NO:6 | TGB6 | AF154424 | deposited May 20, 1999 |
| SEQ ID NO:7 | TGB7 | AF154422 | deposited May 20, 1999 |

Throughout the following discussion, wherever TBG4 is indicated in the description of the invention, it is to be understood that TBG1-3 and 5-7 are also to be included in that description, unless otherwise indicated.

A method of providing a DNA sequence of the invention, either by cloning a cDNA (for instance, pZBG2-1-4) that codes for a protein of the present invention, such as β-galactosidase II, or by deriving the DNA sequence from genomic DNA, or by synthesis of a DNA sequence ab initio using the cDNA sequence as a guide is also provided.

A method for modifying cell wall metabolism which involves modifying the activity of at least one galactosidase, and thus modifying the quality of the fruit is also provided.

Also provided by the present invention is a DNA construct including some or all of an exemplary β-galactosidase DNA sequence under control of a transcriptional initiation region operative in plants, so that the construct can generate RNA in plant cells.

Also discovered is an enhancer/promoter associated with expression of the genes encoding β-galactosidase.

The present invention also relates to recombinant vectors, which include the isolated nucleic acid molecules of the present invention, and to host cells containing the recombinant vectors, as well as to methods of making such vectors and host cells and for using them for production of β-galactosidase polypeptides or peptides by recombinant techniques.

The present invention also provides plant cells containing DNA constructs of the present invention; plants derived therefrom having modified β-galactosidase gene expression; and seeds produced from such plants.

The β-galactosidase II protein of the present invention has demonstrated enzyme activity in cell wall disassembly leading to loss of tissue integrity and fruit softening. The β-galactosidase II protein also may be involved in cell wall turnover, which could be involved in cell extension and/or expansion and therefore plant growth and development.

By hydrolyzing galactose from the cell wall, the enzyme may allow ripening to commence and/or progress, since galactose may be involved in stimulating ethylene production alone or in conjunction with unconjugated N-glycans.

The β-galactosidase of the invention may be involved in conversion of chloroplasts (green—chlorophyll) to chromoplasts (red—lycopene) during fruit ripening by degrading chloroplast membrane galactolipids.

The family of genes represented by the nucleotide sequences shown in FIG. 2 is expected to code for a group of similar enzymes with the same type of hydrolytic activity but with different tissue and/or substrate specificity's or cellular compartmentation profiles.

The β-galactosidase II protein of the present invention as well as other proteins encoded in the nucleotide sequences shown in FIG. 2 may be used for preparation of pectin and other cell wall derived polymers with lowered galactosyl content for use in biofilms and solutions (for example in clarification of fruit juices) requiring lower or higher cross-linking or viscomertric properties.

The present invention also provides β-galactosidase enzymes for use as components of enzyme mixtures for protoplast isolation.

BRIEF DESCRIPTION OF THE FIGURES

FIGS. 1A and 1B shows a phylogenic tree based on shared amino acid sequence identity among tomato β-galactosidase clones TBG1–7 and other known plant β-galactosidase polypeptides.

FIGS. 2A–(1–5), 2B–(1–5), 2C–(1–5), 2D–(1–5), 2E–(1–5), 2F–(1–5), 2G–(1–5) show cDNA sequences SEQ ID Nos: 1–7 for the seven β-galactosidase genes of the invention: TBG1, TBG2, TBG3, TBG4, TBG5, TBG6, and TBG7, respectively.

FIGS. 3A, 3B, 3C, 3D, 3E, 3F, and 3G show the multiple sequence alignment of the deduced amino acid sequences of tomato fruit β-galactosidase for cDNA clones TBG1, TBG2, TBG3, TBG4, TBG5, TBG6, and TBG7 (SEQ ID Nos: 8–16, respectively) and various plant β-galactosidase cDNA clones.

FIG. 4 shows autoradiograph of northern blot analysis of TBG expression in various plant tissues (flowers, leaves, roots and stems).

FIG. 5 shows Autoradiograph of northern blot analysis of TBG expression in fruit tissues at different stages of development.

FIG. 6 shows autogradiograph of northern blot analysis of TBG expression in fruit tissues (mature green or turning stage fruit peel, outer pericarp, inner paricarp and locular).

FIG. 7 shows autoradiograph of northern blot analysis of TBG expression in normal and mutant fruit tissues.

FIG. 8 shows autoradiograph of northern blot analysis of TBG expression in response to ethylene treatment of mature green fruit tissues.

FIG. 9 shows Western blot analysis of TBG4 expression by yeast.

FIGS. 11A–E(1-4) shows the comparative results of texture measurements for fruit from tomato plants containing antisense constructs to suppress TBG4 mRNA and fruit from the parental line.

FIGS. 12A–B show Northern blot analysis of TBG4 expression in transgenic fruit containing TBG4 antisense construct.

FIG. 13 shows a Binary construct used to transform plants and express TBG4 (pZBG2-1-4) in the antisense orientation.

DETAILED DESCRIPTION

Figure 10:
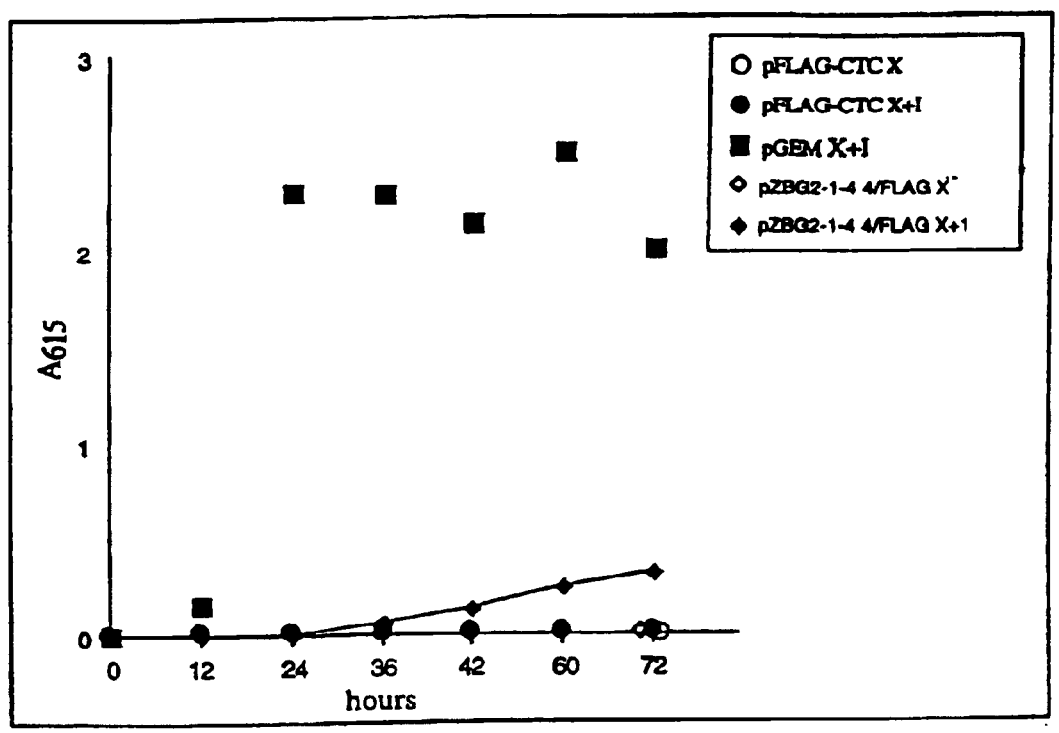
FIG. 10 shows detection of β-galactosidase activity from pZBG2-1-4 expression in E. coli.

The following detailed description is directed to a preferred embodiment of the present invention and is intended as illustrative of each of other DNA sequences of the present invention.

The present invention provides isolated nucleic acid molecules comprising a polynucleotide encoding β-galactosidase polypeptides, particularly a β-galactosidase II polypeptide having the amino acid sequence shown in FIG. 2. The DNA sequence of the exemplary β-galactosidase II cDNA clone of the invention, which was determined from a cDNA clone, pZBG2-1-4, encoding β-galactosidase II, is recorded in GenBank as Accession Number AF020390. Not all β-galactosidases possess in vitro activity against extracted cell wall material via the release of galactose from wall polymers containing β(1→4)-D-galactan. The polypeptide expressed from the exemplary β-galactosidase II clone, pZBG2-1-4, has been shown to exhibit β-galactosidase activity and exogalactinase activity.

The exemplary β-galactosidase II protein of the present invention, as shown in FIG. 2, shares sequence homology with the amino acid sequence deduced from β-galactosidase cDNA clones of TBG2–7 and cDNA clones of the fruits of asparagus (accession number P45582), apple (accession number P48981), and carnation (accession number Q00662), as well as with β-galactosidase cDNA clones of a previously published sequence of a tomato β-galactosidase cDNA clone designated pTomβgal1 (accession number P48980) isolated from ripe 'Ailsa Craig' fruit (Carey et al., 1995). The ORF of the clone TBG1 disclosed herein by the inventors (accession number AF023847) is nearly identical to the cDNA previously described by Carey et al. As shown in FIG. 2, the shared deduced sequence identity is high among all the published plant β-galactosidases of the seven clones (TBG1-7) and the other plant β-galactosidases.

BLAST searches of the database also indicated significant shared sequence identity between domains of the plant β-galactosidases and mammalian and fungal β-galactosidases, however little share sequence identity was detected with bacterial β-galactosidases.

As shown in FIG. 1, the shared amino acid identity of TBG1 and TBG3 was high. TBG4 was also very similar to both TBG1 and 3. The amino acid sequences of TBG2 and 7 were unique because several regions of amino acid insertions appear throughout their sequence (FIG. 3).

Nucleic Acid Molecules

Unless otherwise indicated, all nucleotide sequences determined by sequencing a DNA molecule herein were determined using a PCR-based dideoxynucleotide terminator protocol and an ABI automated DNA sequencer (such as the Model 373 from Applied Biosystems, Inc., Foster City, Calif.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

By "nucleotide sequence" of a nucleic acid molecule or polynucleotide is intended, for a DNA molecule or polynucleotide, a sequence of deoxyribonucleotides, and for an RNA molecule or polynucleotide, the corresponding sequence of ribonucleotides (A, G, C and U), where each thymidine deoxyribonucleotide (T) in the specified deoxyribonucleotide sequence is replaced by the ribonucleotide uridine (U).

Using the information provided herein, such as the exemplary nucleotide sequence shown in FIG. 2 [SEQ ID NO: 4], a nucleic acid molecule of the present invention encoding a β-galactosidase II polypeptide may be obtained using standard cloning and screening procedures, such as those for cloning cDNAs using mRNA as starting material. Illustrative of the invention, the nucleic acid molecule described in FIG. 2 [SEQ ID NO: 4] was discovered in a cDNA library derived from breaker, turning and pink fruit pericarp from 'Rutgers' tomato plants.

The complete sequence of the cDNA insert of pZBG2-1-4 is accessible in the GenBank (no. AF020390) and is provided in FIG. 2 [SEQ ID NO: 4]. The cDNA insert is 2532 nucleotides (nt) long and contains a single, long open reading frame (ORF) predicted to start with the first in-frame ATG at nt 64 and end with TAA at nt 2238. This ORF codes for a 79 kD protein 724 amino acids long. The deduced amino acid sequence of pZBG2-1-4 shared significant amino acid identity to all published plant β-galactosidase sequences in the database (FIGS. 1A,B). When the entire ORF of each β-galactosidase gene was compared to pZBG2-1-4, the shared sequence identity was about 64% for tomato pTomβgal 1 (P48980), about 67.6% for apple (P48981), about 63% for asparagus (P45582) and about 55% for carnation (Q00662). As one of ordinary skill would appreciate, due to the possibilities of sequencing errors discussed above, the actual complete β-galactosidase II polypeptide encoded by the deposited cDNA, which comprises about 724 amino acids, may be somewhat longer or shorter. More generally, the actual open reading frame may be anywhere in the range of ±20 amino acids, more likely in the range of ±10 amino acids, of that predicted from either the first methionine codon from the N-terminus shown in FIG. 2 [SEQ ID NO: 4]. In any event, as discussed further below, the invention further provides polypeptides having various residues deleted from the N-terminus of the complete polypeptide, including polypeptides lacking one or more amino acids from the N-terminus of the β-galactosidase II polypeptide described herein.

Leader and Mature Sequences

Analysis of the deduced amino acid sequence of pZBG2-1-4 suggested a high probability for secretion based on the presence of a hydrophobic leader sequence, a leader sequence cleavage site and three possible N-glycosylation sites. The programs PSORT V6.4 (Nakai and Kanehisa, 1992, incorporated herein by reference) and SignalP V1.1 (Nielsen et al., 1997, incorporated herein by reference), were used to predict that the ORF contains a hydrophobic leader sequence that would be cleaved between the alanine and serine residues at positions 23 and 24 respectively, and that the mature polypeptide has an extracellular location. The mature polypeptide contains three possible N-glycosylation sites at asparagine numbers 282, 459 and 713, however the asparagine at position 713 is unlikely to be glycosylated due to the proline at position 714. The predicted molecular mass of the unglycosylated mature polypeptide was 75 kD with a pI of 8.9.

Accordingly, the amino acid sequence of the complete β-galactosidase II protein of the invention includes a leader sequence and a mature protein, as shown in FIG. 3 [SEQ ID NO: 4]. More in particular, the present invention provides nucleic acid molecules encoding a mature form of the β-galactosidase II protein. Thus, according to the signal hypothesis, secreted proteins have a signal or secretory leader sequence which is cleaved from the complete polypeptide to produce a secreted "mature" form of the protein. In some cases, cleavage of a secreted protein is not entirely uniform, which results in two or more mature species of the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature β-galactosidase II polypeptide having the amino acid sequence encoded by the cDNA shown in FIG. 2 [SEQ ID NO: 4] and provided in GenBank (Accession No. AF20390). By the "mature β-galactosidase II polypeptide having the amino acid sequence encoded by the cDNA clone shown in FIG. 2 [SEQ ID NO: 4] is meant the mature form(s) of the β-galactosidase II protein produced by expression in a plant cell of the complete open reading frame encoded by the cDNA sequence of the clone shown in FIG. 2 [SEQ ID NO: 4] and provided in GenBank (Accession No. AF20390).

The exemplary β-galactosidase II cDNA of the present invention (TBG4) has been expressed in *E. coli* strain XLI blue MR (lacZ) (Stratagene, La Jolla, Calif.), as described hereinbelow (see Example).

Analysis of the deduced amino acid sequence of cDNA clones representing the other β-galactosidase genes of the invention also revealed open reading frames and, in some cases, suggested a high probability for secretion of the encoded proteins. All the full-length cDNA clones were predicted to have a signal sequence (FIG. 2). Using the two prediction programs SignalP and PSORT, TBG4 was predicted to be secreted by both programs. TBG1, 2 and 3 were predicted to have cleavable signal sequences by SignalP, but uncleavable signal sequences by PSORT. TBG7 was suggested to be targeted to the chloroplast by PSORT. Particular observations for each of the seven clones are as follows, based on the presence of a hydrophobic leader predicted by the programs PSORT V6. and SignalP V1.1: TBG1: initiation codon at 306 [SEQ ID NO: 1], ORF=835 amino acids [SEQ ID NO: 8], signal sequence at 1–24; TBG2: initiation codon not determined [SEQ ID NO: 2], ORF=888 amino acids [SEQ ID NO: 9], signal sequence at 1–25; TBG3: initiation codon at 32 [SEQ ID NO: 3], ORF=838 amino acids [SEQ ID NO: 10], signal sequence at 1–22; TBG5: initiation codon not determined [SEQ ID NO: 5], ORF=251 amino acids [SEQ ID NO: 12], signal sequence not determined; TBG6: initiation codon not determined [SEQ ID NO:6], ORF=248 amino acids [SEQ ID NO: 13], signal sequence not determined; TBG7: initiation codon at 104 [SEQ ID NO: 7], ORF=870 amino acids [SEQ ID NO: 14], signal sequence at 1–35.

The deduced amino acid sequences of the seven clones was also subjected to analysis using the program DNAsis and the predictions for molecular mass, cellular targeting, pI and potential N-linked glycosylation sites are summarized in Table I.

TABLE I

Tomato β-galactosidase (TBG) cDNA sequence data. Fiv full-length and 2 partial-length cDNAs were cloned and sequenced. The DNA and deduced amino acid sequence data is presented below

| CLONE | mRNA(kb) | kD | pI | N-LINK | TARGET |
|---|---|---|---|---|---|
| TBG1 | 3.2 | 90.8 | 6.2 | 2 | ER/OUT |
| TBG2 | 3.0 | 97.0 | 6.2 | 6 | PM |
| TBG3 | 2.8 | 90.5 | 8.2 | 1 | ER/OUT |
| TBG4 | 2.6 | 77.9 | 8.9 | 3 | OUT |
| TBG5 | ~3 | | | | |
| TBG6 | ~3 | | | | |
| TBG7 | 3.0 | 93.3 | 8.0 | 6 | CHLOR |

N-LINK = possible N-linked glycosylation sites;
ER = endoplasmic reticulum;
out = secreted;
PM = tethered to plasma membrane;
CHLOR = chloroplast As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules comprising an open reading frame (ORF) with an initiation codon at position 64 of the nucleotide sequence shown in FIG. 2 [SEQ ID NO: 4]. Also included are DNA molecules comprising the coding sequence for the mature β-galactosidase II protein shown at positions 135–2532 of FIG. 2 [SEQ ID NO: 4].

In addition, isolated nucleic acid molecules of the invention include DNA molecules which comprise a sequence substantially different from those described above but which, due to the degeneracy of the genetic code, still encode the β-galactosidase II protein. Of course, the genetic code and species-specific codon preferences are well known in the art. Thus, it would be routine for one skilled in the art to generate the degenerate variants described above, for instance, to optimize codon expression for a particular host (e.g., change codons in the plant mRNA to those preferred by a bacterial host such as *E. coli*). Preferably, this nucleic acid molecule will encode the mature polypeptide encoded by the above-described deposited cDNA clone.

The invention further provides an isolated nucleic acid molecule having the nucleotide sequence shown in FIG. 2 [SEQ ID NO: 4] or a nucleic acid molecule having a sequence complementary to the above sequence. Such isolated molecules, particularly DNA molecules, are useful as probes for gene mapping, by in situ hybridization with chromosomes, and for detecting expression of the β-galactosidase II gene in plant tissue, for instance, by Northern blot analysis.

The present invention is further directed to nucleic acid molecules encoding portions of the nucleotide sequences described herein as well as to fragments of the isolated nucleic acid molecules described herein. In particular, the invention provides a polynucleotide having a nucleotide sequence representing the portion of FIG. 2 [SEQ ID NO: 4] which consists of positions 1–2538 of FIG. 2 [SEQ ID NO: 4].

In addition, the invention provides additional nucleic acid molecules having nucleotide sequences related to extensive portions of FIG. 2 [SEQ ID NO: 4] which have been determined from the following related cDNA clones: TBG1-3 and TBG5-7 as shown in FIG. 3, SEQ. NO's 1–3 and 5–7

In another aspect, the invention provides an isolated nucleic acid molecule comprising a polynucleotide which hybridizes under stringent hybridization conditions to a portion of the polynucleotide in a nucleic acid molecule of the invention described above, for instance, the cDNA clone shown in FIG. 2 [SEQ ID NO: 4]. By "stringent hybridization conditions" is intended overnight incubation at 42° C. in a solution comprising: 50% formamide, 5×SSC (150 mM NaCl, 15 mM trisodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C.

As indicated, nucleic acid molecules of the present invention which encode a β-galactosidase II polypeptide may include, but are not limited to those encoding the amino acid sequence of the mature polypeptide, by itself; and the coding sequence for the mature polypeptide and additional sequences, such as those encoding the about 1–23 amino acid leader sequence, such as a pre-, or pro- or preproprotein sequence; the coding sequence of the mature polypeptide, with or without the aforementioned additional coding sequences.

Also discovered is an enhancer/promoter associated with expression of the genes encoding β-galactosidase. The inventors have characterized the expression profile of TBG2 mRNA and have cloned a lambda genomic cDNA. TBG2 is expressed before the onset of fruit ripening and continues at uniform level throught all the ripening stages. TBG2 has been found to be expressed in all fruit tissues and has also been found to be fruit specific. Experiments have shown TBG2 to be unaffected by ethylene. TBG2 is expressed in the ripening mutants rin, nor and Nr at the normal chronological time after anthesis. The promoter discovered would be useful to express any gene in the sense or antisense orientation, specifically in tomato fruit, in all tomato fruit tissues, starting before and continuing throughout the entire ripening process. The promoter could also be used to express any gene in the ripening mutants rin, nor and Nr without the need to gas the fruit with exogenous ethylene.

Variant and Mutant Polynucleotides

The present invention further relates to variants of the nucleic acid molecules of the present invention, which encode portions, analogs or derivatives of the β-galactosidase II protein. Variants may occur naturally, such as a natural allelic variant. By an "allelic variant" is intended one of several alternate forms of a gene occupying a given locus on a chromosome of an organism. Genes II, Lewin, B., ed., John Wiley & Sons, New York (1985). Non-naturally occurring variants may be produced using art-known mutagenesis techniques.

Such variants include those produced by nucleotide substitutions, deletions or additions. The substitutions, deletions or additions may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and activities of the β-galactosidase II protein or portions thereof. Also especially preferred in this regard are conservative substitutions.

Most highly preferred are nucleic acid molecules encoding the mature protein having the amino acid sequence shown in FIG. 2 as pZBG2-1-4 or the mature β-galactosidase II amino acid sequence encoded by the deposited cDNA clone.

Further embodiments include an isolated nucleic acid molecule comprising a polynucleotide having a nucleotide sequence at least 90% identical, and more preferably at least 95%, 96%, 97%, 98% or 99% identical to a polynucleotide selected from the group consisting of: (a) a nucleotide sequence encoding the β-galactosidase II polypeptide having the complete amino acid sequence in FIG. 2 [SEQ ID NO: 4] (b) a nucleotide sequence encoding the mature β-galactosidase II polypeptide shown in FIG. 2 [SEQ ID NO: 4]; (c) a nucleotide sequence complementary to any of the nucleotide sequences in (a) or (b) above.

Vectors and Host Cells

The present invention also relates to vectors which include the isolated DNA molecules of the present invention, host cells which are genetically engineered with the recombinant vectors, and the production of β-galactosidase II polypeptides or fragments thereof by recombinant techniques. The vector may be, for example, a phage, plasmid, viral or retroviral vector. Retroviral vectors may be replication competent or replication defective. In the latter case, viral propagation generally will occur only in complementing host cells.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

The DNA insert should be operatively linked to an appropriate promoter, such as the phage lambda PL promoter, the E. coli lac, lrp, phoA and tac promoters the SV40 early and late promoters and promoters of retroviral LTRs, to name a few. Other suitable promoters will be known to the skilled artisan. The expression constructs will further contain sites for transcription initiation, termination and, in the transcribed region, a ribosome binding site for translation. The coding portion of the transcripts expressed by the constructs will preferably include a translation initiating codon at the beginning and a termination codon (UAW, UGA or UAG) appropriately positioned at the end of the polypeptide to be translated.

As indicated, the expression vectors will preferably include at least one selectable marker. Such markers include dihydrofolate reductase, G418 or neomycin resistance for eukaryotic cell culture and tetracycline, kanamycin or ampicillin resistance genes for culturing in E. coli and other bacteria. Representative examples of appropriate hosts include, but are not limited to, bacterial cells, such as E. coli, StrepZBG2-1-4yces and Salmonella typhimurium cells; fungal cells, such as yeast cells; insect cells such as Drosophila S2 and Spodoptera Sf9 cells; animal cells such as CHO, COS, 293 and Bowes melanoma cells; and plant cells.

Appropriate culture mediums and conditions for the above-described host cells are known in the art.

Among vectors preferred for use in bacteria include pQE70, pQE60 and pQE-9, available from QIAGEN, Inc., supra; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Other suitable vectors will be readily apparent to the skilled artisan.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic Methods In Molecular Biology.* (1986).

EXAMPLE

Tomato (*Lycopersicon esculentum* Mill., cv. 'Rutgers') plants were grown in a greenhouse using standard cultural practices. The ripening mutants, ripening inhibitor (rin), non-ripening (nor) and never ripe (Nr) (Tigchelaar et al., 1978), were all in the 'Rutgers' background. Flowers were tagged at anthesis and fruit were harvested according to the number of days post-anthesis (dpa) or based on their surface color using ripeness stages as previously described (Mitcham et al., 1989), the complete disclosure of which is hereby fully incorporated herein by reference. For gene expression studies, a variety of leaf, flower, and stem tissues were harvested from greenhouse-grown plants and roots were harvested from seedlings grown in basal tissue culture medium for 4 weeks after seed germination.

RNA Extraction

Fruits were processed immediately after harvest in the greenhouse by chilling on ice, excising the various tissues and freezing them in liquid nitrogen. Tissue samples were ground using a mortar and pestle and stored at −80° C. RNA was extracted using the method described in Verwoerd et al. (1989). Poly(A)RNA was purified from total RNA using oligo(dT) columns (Pharmacia, Piscataway, N.J.). RNA was quantified by measuring $A_{260}$ using a dual beam spectrophotometer.

RT-PCR

Degenerate primers were designed based on the highest shared deduced amino acid sequence identity we found between an apple (accession number P48980), asparagus (P45582) and carnation (Q00662) β-galactosidase cDNA clones. The two primers used for the first reaction were BG5'E1 (WSNGGNWSNATHCAYTAYCC) and BG3'E (CCRTAYTCRTCNADNGGNGG). A second reaction was done on the products of the first reaction using BG5'I1 (ATHCARACNTAYGTNTTYTGG) and BG3'E. The degeneracy code for the primer sequences is N=a+t+c+g; H=a+t+c; B=t+c+g; D=a+t+g; V=a+c+g; R=a+g; Y=c+t; M=a+c; K=t+g; S=c+g; and W=a+t. The 5' and 3' primers corresponded to amino acids 72–78 and 321–315 of the apple clone, respectively. Amplification was done using AmpliTaq DNA polymerase (Perkin Elmer, Norwalk, Conn.) and standard PCR conditions using the cDNA made for the first cDNA library described below as a template (Ausubel et al., 1987). PCR products were separated in an agarose gel and fragments of the expected size (approximately 750 bp) were purified, cloned into pCRscript (Stratagene, La Jolla, Calif.), and sequenced.

cDNA Library

Two cDNA libraries were constructed. The first comprised poly(A) RNA isolated from breaker, turning and pink fruit pericarp from 'Rutgers' plants. The cDNA synthesis and library construction was done exactly according to the manufacturers instructions for the ZAP-cDNA Gigapack II Gold Cloning Kit (Stratagene), the complete disclosure of which is fully incorporated herein by reference. First-strand cDNA synthesis was primed using a poly(dT) primer and inserts were directionally cloned into the Uni-Zap XR vector using EcoRI and XhoI restriction sites. The second library comprised poly(A) RNA isolated from all fruit tissues (except seeds) from immature green, mature green, breaker, turning, pink, red-ripe and over-ripe fruit of 'Rutgers' plants. The cDNA synthesis and library construction was done exactly according to the manufacturers instructions for the SuperScript Lambda System for cDNA synthesis and . Cloning (GibcoBRL, Gaithersburg, Md.). First-strand cDNA synthesis was primed using a oligo(dT) primer and cDNA inserts were directionally cloned into the . ZipLox cloning vector using SalI and NotI restriction sites. Both libraries were amplified and maintained using the host strains provided by the manufacturer, according to their instructions.

One of the clones (RT-PCR2-1) was used to screen $10^6$ plaques from the tomato fruit cDNA libraries at low stringency (hybridization at 45° C., no formamide and final wash with 0.2×SSC at 42° C.). Thirty positive cDNA clones were identified and partially sequenced. Complete sequencing and characterization of the RT-PCR and cDNA clones revealed the possibility of seven unique β-galactosidase genes.

DNA and RNA Gel Blot Analysis

Southern analysis was done using the 3' UTR of each full length clone and the RT-PCR clones as probes against restriction enzyme digested genomic DNA. DNA gel blot analysis was done essentially as described in Smith and Fedoroff (1995) except that 3 μg of genomic DNA was used for each digest. The genes corresponding to the clones appeared to be present as single copies (data not shown). The same probes were used to map 6 of the 7 genes using RFLPs of recombinant inbred lines and the loci names and map positions are shown in Table II (James Gioviannone, Texas A&M University, personal communication).

TABLE II

TBG loci map positions. Genes were maped by Southern analysis using RFLPs of recombinant inbred lines.

| Gene | chromosome | map position |
|------|------------|--------------|
| TBG1 | 12* | overlap of IL 12-2, IL 12-3 |
| TBG2 | 9 | IL 9-3 |
| TBG3 | 3 | IL 3-5 |
| TBG4 | 12* | overlap of IL 12-2, IL 12-3 |
| TBG5 | 11 | IL 11-3 |
| TBG6 | 2 | overlap of IL 2-4, IL 2-5 |
| TBG7 | no RFLP | |

*TBG1 and 4 are loosely linked

Total RNA (20 μg/lane) was separated in a formaldehyde/Mops agarose gel, transferred to Hybond-N$^+$ nylon membrane (Amersham, Arlington Heights, Ill.), fixed by incubating for 2 h at 80° C., hybridized overnight in a hybridization incubator (Robbins Scientific, Sunnyvale, Calif.) using a buffer described by Church and Gilbert (1984) washed to a final stringency of 0.1×SSC with 0.2% SDS at 65° C., and autoradiographed essentially as described by Ausubel et al. (1987). An RNA ladder standard (GibcoBRL) was used to estimate the length of the RNAs.

Probes were synthesized using a random priming kit with $^{32}$p-dATP as the label (Boehringer Mannheim, Indianapolis, Ind.). Northern analysis was done using the 3' UTR of each full length clone and the RT-PCR clones as templates for probe synthesis. As a loading control, RNA blots were stripped and re-probed at a reduced hybridization and washing stringency using a soybean 26S rDNA fragment (Turano et al., 1997). For all hybridizations, $^{32}$P(dATP)-labeled probe was diluted to $1-2\times10^6$ dpm/mL. The complete disclosures of the above references are fully incorporated herein by reference.

Sequence Analysis

Sequencing was done at the Iowa State University Sequencing Facility (Ames, Iowa) using a PCR-based dideoxynucleotide terminator protocol and an ABI automated sequencer (Applied Biosystems, Foster City, Calif.). The sequencing of both cDNA insert strands was done by primer walking. Nucleotide and deduced amino acid sequence comparisons against the databases were done using BLAST searches (Altschul et al., 1990). Sequence data were analyzed and aligned using DNA Strider 1.2 (Marck, 1988) and MacDNAsis (Hitachi, San Bruno, Calif.) software. The complete disclosures of the above references are fully incorporated herein by reference.

Northern Blot Analysis

Tissue Specific Expression

Northern blot analysis was done to reveal which, if any, of the β-galactosidase genes had a fruit-specific expression pattern. With the exception of TBG2, transcripts of all clones were detected in non-fruit tissues (FIG. 4). Transcripts of TBG 1, 4, 5 and 6 were detected in all the tissues tested. TBG3 transcript was detected at low levels in root and stem tissues, while TBG7 transcript was detected in flower and stem tissues.

Temporal Expression Pattern in Fruit

The temporal expression pattern of the seven genes in fruit tissue was examined using RNA extracted from all fruit tissues except seeds. Transcripts for all seven genes were detected during some stage of fruit development (FIG. 5). TBG1 and 3 had similar expression patterns and their transcripts were detected throughout the breaker to over-ripe stages. TBG2 had a unique expression pattern and its transcript was detected at a constant level from 30 dpp to the over ripe stage. TBG4 expression pattern was similar to TBG1 and 3, but differed in that the transcript level was significantly higher at the turning stage. TBG5 had a similar expression pattern to TBG4 during the ripening stages of development, however TBG5 transcript was also detected throughout all the earlier stages of fruit development. TBG6 had an interesting expression pattern and its transcript was only detected at high levels in all pre-ripening stages tested. TBG7 also had a unique expression pattern and its transcript was detected at very low levels throughout all the stages tested, and at moderate levels at 10 dpp and the over-ripe stage.

Spatial Expression Pattern in Fruit

Northern blot analysis was also done to determine transcript accumulation in various fruit tissues. Since there were temporal differences in the expression patterns of the TBG genes both the mature green and turning fruit stages were used for RNA extractions (FIG. 6). Both TBG2 and TBG6 transcripts were detected in all mature green fruit tissues tested. TBG7 transcript was present in all fruit tissues tested except for locules. Both TBG1 and TBG4 transcripts were detected in RNA samples extracted from all turning stage fruit tissues. TBG4 transcript was notably more abundant in the peel. TBG3 and TBG5 expression.patterns were unique and their transcripts were detected in all tissues except the outer pericarp and locular respectively.

Expression in Normal Versus Mutant Fruit

In order to better understand the potential roles of the TBG products and transcriptional regulatory mechanisms, northern analysis was performed using fruit tissue from the ripening mutants rin, nor and N$^r$. This analysis was important because it might give clues for preliminary determination of any potential ripening and/or softening role any of the TBGs might possess.

The results of mutant fruit Northern analysis suggested that the transcriptional regulation of TBG1, 2, 3, 5 and 7 was unaffected in mutant fruit tissue and that their transcripts were present in a normal chronological (dpp) pattern (FIG. 7). The abundance of TBG4 and 6 transcripts were however different in the mutant fruit. TBG4 transcript was not detected in fruit tissue of N$^r$ and was detected at much lower levels in rin and nor than wild type fruit tissues. Normally TBG6 transcripts are detectable at high levels throughout the early stages of fruit development but are not detectable after the mature green stage (40–42 dpp). TBG6 transcripts persisted even to 50 dpp in fruit of all three mutants.

Transcriptional Regulation by Ethylene

The northern analysis done using mutant and wild type fruit suggested that TBG4 expression might be up-regulated by ethylene and that TBG6 expression might be down-regulated by ethylene. In order to evaluate this hypothesis mature green fruit were harvested and subjected to a continuous flow of 10 ppm ethylene mixed in air. Control and ethylene-treated fruit were used for RNA extractions at 1, 2, 12 and 24 hours. The results of this experiment confirmed the findings from the mutant fruit northern analysis. As expected, the presence and abundance of TBG1, 2, 3, 5 and 7 transcripts was essentially unaffected in mature green tissues subjected to exogenous ethylene treatment (FIG. 8). However, TBG4 transcript abundance was increased in mature green tissues in the presence of ethylene. From the data presented it was unclear whether TBG6 transcript abundance was reduced by exogenous ethylene treatment since its transcript level was normally reduced at this stage of fruit development.

Enzyme Activity

In order to determine the role of the TBG encoded products we initiated experiments to express the cDNA encoded enzymes using heterologous expression systems. Several E. coli expression systems were tested, but the yield of product was very low due to toxicity (See the example below). Therefore we used a yeast expression system which secretes a mature amino-terminal-FLAG fusion protein into the culture medium. The TBG4 cDNA was tested first and resulted in the production of approximately 1 mg TBG4 active protein per 50 mls culture. TBG4 was used first because the cDNA codes for the enzyme β-galactosidase II which was purified from tomato fruit and has been characterized in some detail (Carey et al 1995, Smith et al 1998). Therefore we could compare the activity of the heterologous system-expressed protein to the native enzyme purified from tomato. The TBG4 protein was successfully affinity purified using an anti-FLAG affinity resin (FIG. 9).

The affinity-purified TBG4 enzyme was shown to have β(1→4)-D-galactosidase activity by virtue of its ability to hydrolyze the synthetic substrate p-nitrophenyl-β-D-galactopyranoside (Smith et al. 1998). The enzyme can cleave galactosyl residues from a variety of cell wall substrates and therefore has exo-galactanase activity (Table III). The remaining full-length cDNA clones are currently being tested for successful expression of active enzyme. Preliminary results have shown that TBG1 codes for an enzyme which also has both β-D-galactosidase and exo-galactanase activity (Table III).

TABLE III

Cell wall degrading activity of TBG4 and TBG1 expressed in yeast. Removal of galactosyl residues from chelator soluble (CSP) and alkali soluble (ASP) pectin and hemicellulosic (HCF) cell wall fractions purified from tomato fruit.

| | | μg galactose released | |
|---|---|---|---|
| enzyme | substrate | boiled | live |
| [a]TBG4 | CSP | 0 | 5 |
| | ASP | 0 | 14.5 |
| | HCF | 0 | 4 |
| [b]TBG1 | ASP | 0 | 1.2 |

2 mg substrate; 4 hours at 37° C.
[a].005 units enzyme/rx
[b].005 units enzyme/rx pZBG2-1-4 Codes for a β-Galactosidase The TBG4 ORF was cloned in-frame into the repressible/inducible bacterial expression vector pFLAG-CTC. The host strain XL1-Blue MR is a mutant strain containing no endogenous β-galactosidase activity nor α-complementation. Induction of gene transcription by (IPTG) caused the immediate cessation of *E. coli* growth at 30 to 37° C. However, induction at 20° C. did allow for some limited *E. coli* growth. When clones containing the pZBG2-1-4 4 ORF were grown at 20° C. and induced with IPTG, the cells slowly turned blue after 36 hrs growth in medium containing the β-galactosidase substrate X-GAL, (FIG. 10). If not induced with IPTG, no blue color was seen, even after extended growth in media containing X-GAL. As an additional negative control, clones consisting of XL1-Blue MR transformed with the FLAG vector alone never showed any β-galactosidase activity with or without IPTG-induction, even after 7-days growth (FIG. 10). As a positive control for maximal β-galactosidase (derived from *E. coli* β-galactosidase) activity the cloning vector pGEM was transformed into the host strain DH5α and the results are also shown in FIG. 10. FIG. 10 shows the detection of β-galactosidase activity from pZBG2-1-4 expression in *E. coli*. Cells were harvested and extracts were prepared every 12 hours and the $A_{615}$ measured. Cultures were grown with the addition of the chromogenic substrate X-GAL (open symbols) or X-GAL and the transcriptional inducer IPTG (closed symbols) in the medium. The vector used as a positive control for *E. coli* β-galactosidase activity was pGEM (■) and the vector used as a negative control and for expression was pFLAG-CTC either without (○,●) or containing the pZBG2-1-4 ORF (Δ,▲).

Effects on Plant Tissue Texture

To further demonstrate the function of TBG4 encoded β-galactosidase II the following experiments were carried out.

Fruit from tomato plants containing antisense constructs to suppress TBG4 mRNA were up to 40% firmer [compare means of parental line #1 with antisense line #2 in FIGS. 11A–11E(1-4)] than fruit from the parental line. Among the transformants the line with the firmest fruit also had the lowest overall levels of TBG4 mRNA (FIGS. 12A,B). This correlation suggests that a reduction in TBG4 mRNA is associated with increased fruit firmness. Firmer fruit might result in (1) less shipping damage (a) less loss due to damage and (b) ability to harvest at later stage resulting in better flavor at market (2) longer shelf life for both market and consumer. (3) better quality fruit for fresh slice market; fruit cut better at the pink/red stage when firmer.

Methods

To determine the function of TBG4 encoded β-galactosidase II, antisense constructs were made using the constitutively expressed 35S CaMV promoter to express TBG4 antisense RNA (FIG. 13). Constructs were moved into tomato using Agrobacterium-mediated transformation. Four tomato cultivars have been transformed in order to evaluate the effect of TBG4 suppression on processing tomato (cv 'UC82b') fruit paste quality and three fresh pick cultivars. Of the fresh pick cultivars one is a soft fruit large cherry tomato (cv 'Ailsa Craig'), the second is a soft fruit old breeding line (cv 'Rutgers') and the third is a recently developed somewhat firm cultivar 'New Rutgers'. Among the lines where TBG4 mRNA is suppressed we expect to observe an increase in firmness and paste viscosity.

Texture

Figure 11A:
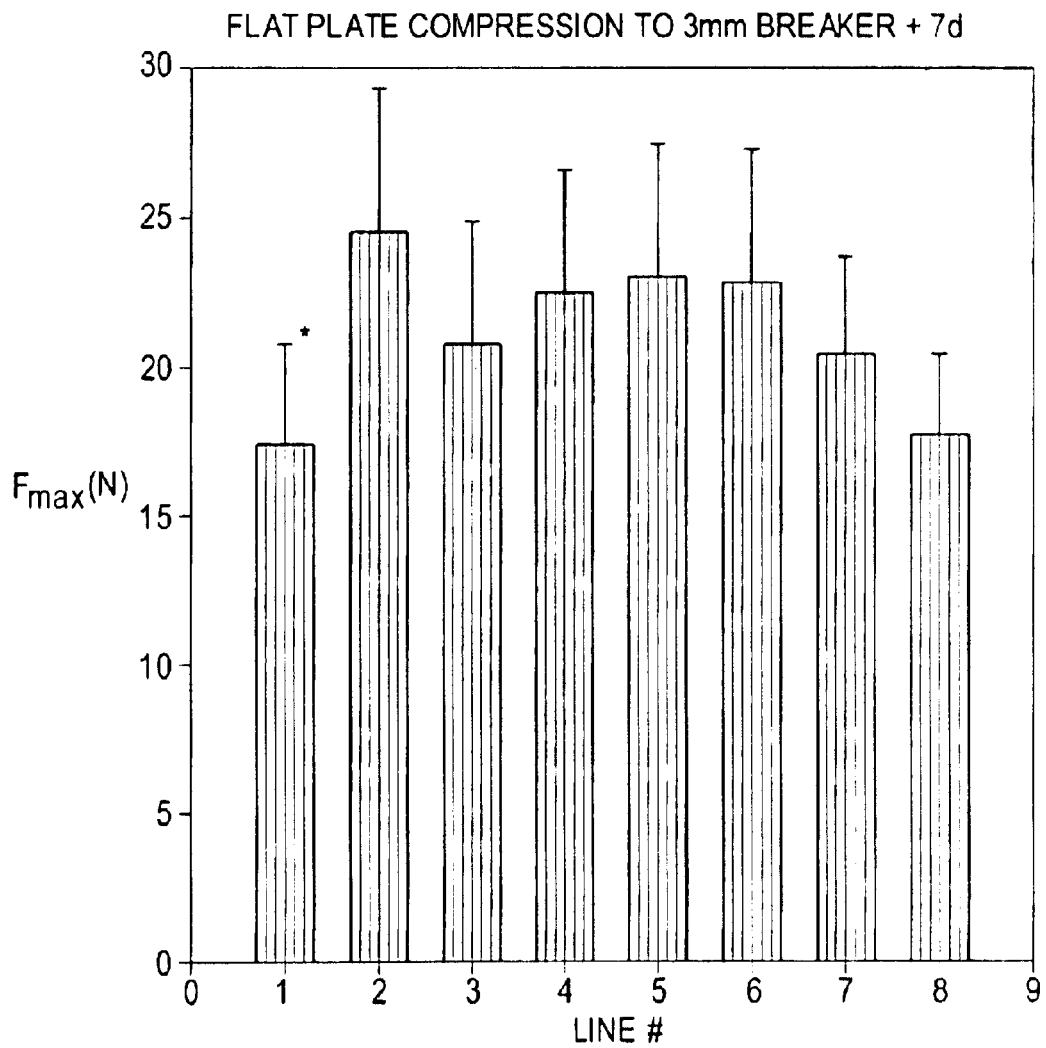
Figure 11B:
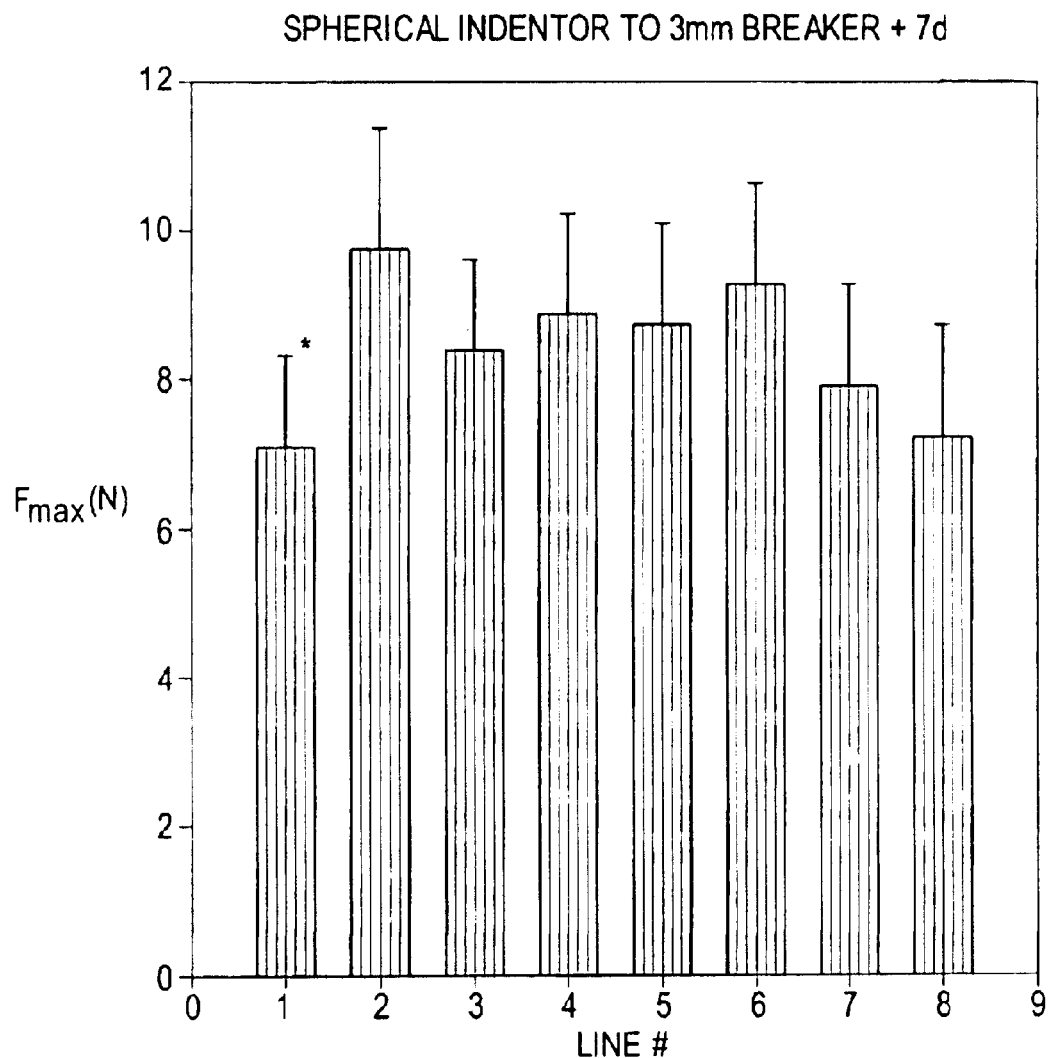
Figure 11C:
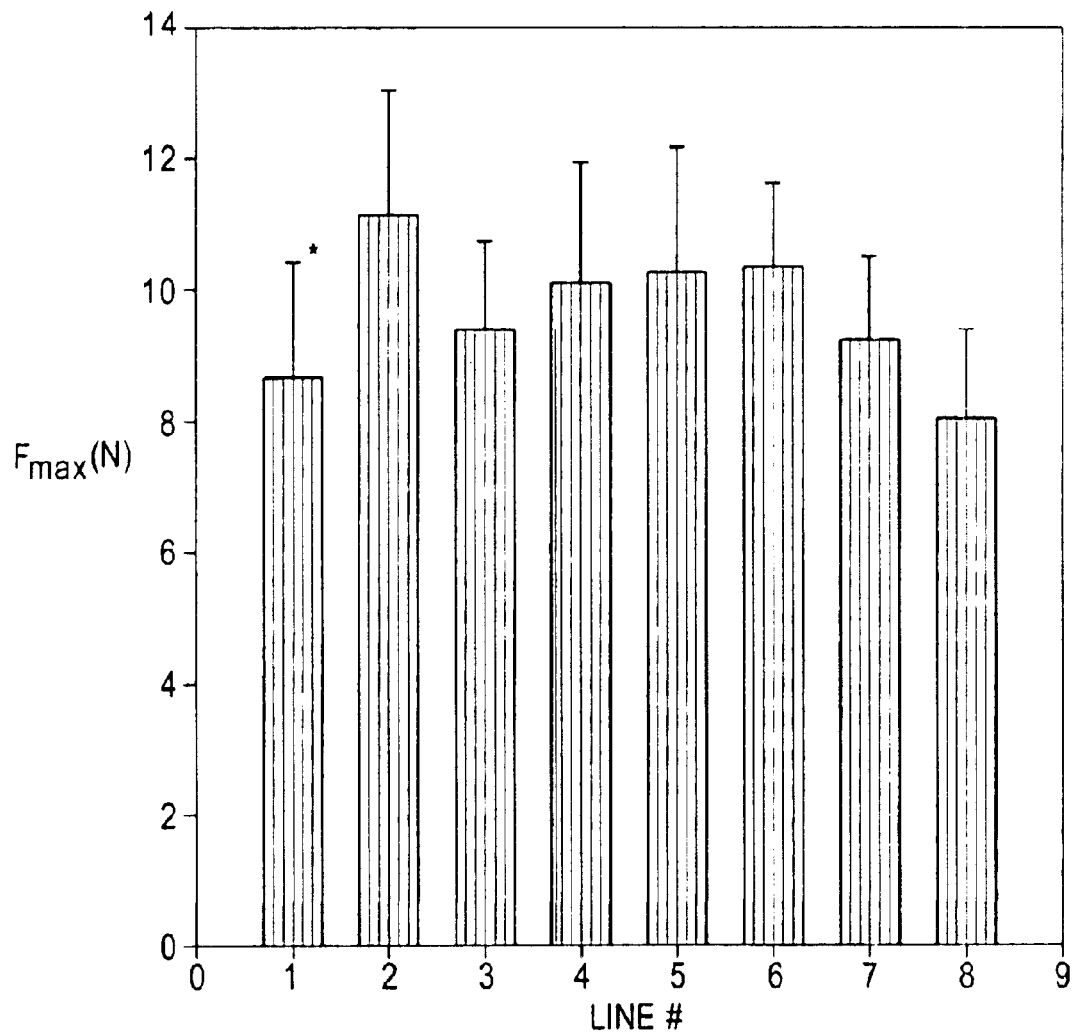
Figure 11D:
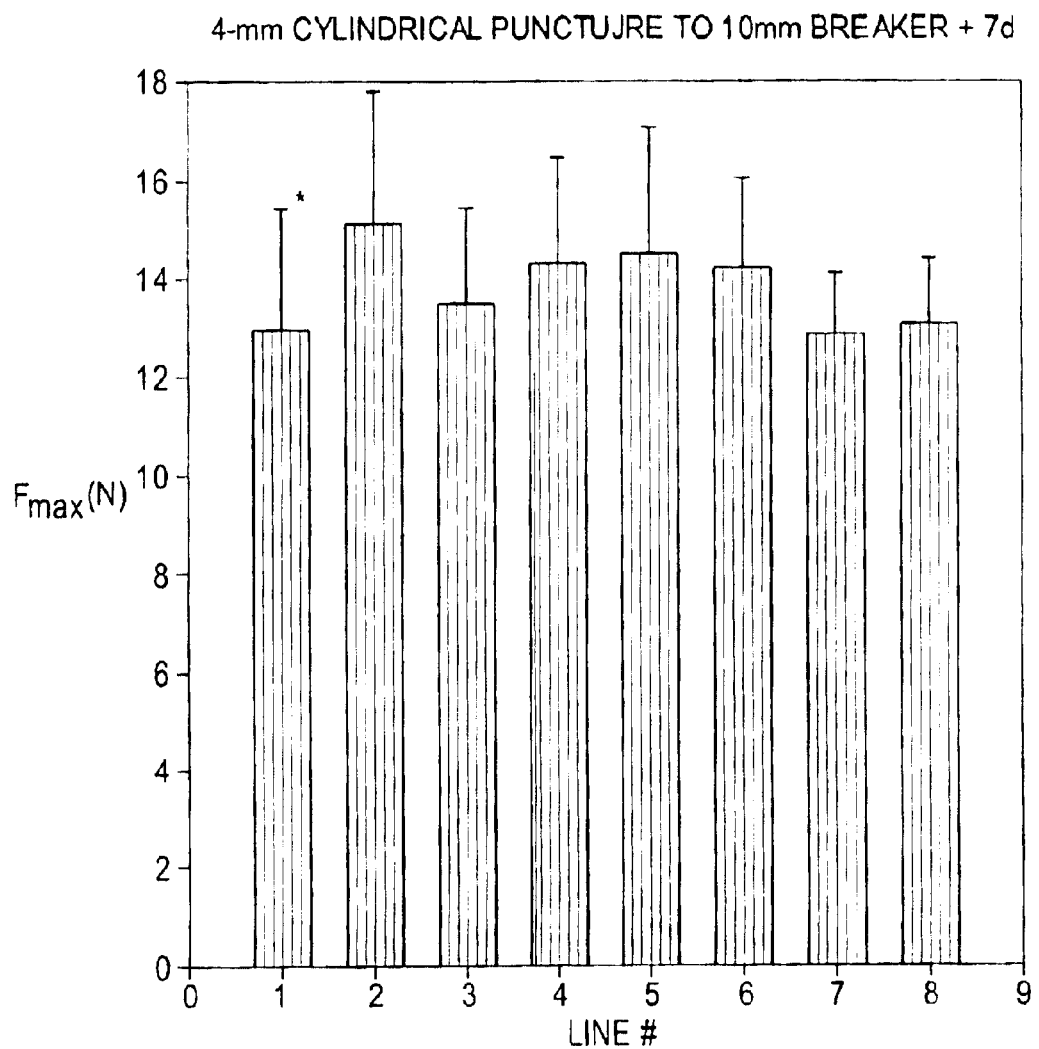

Although this project is nearly finished the complete biochemical and molecular analysis is not finished. The preliminary results on the analysis of the 'New Rutgers' cultivar is presented in FIGS. 11A–E(1-4) and 12A,B. In this example a fresh pick cultivar called 'New Rutgers' was used. Plants of the purchased seed were grown and allowed to self and the resulting seed was used as the parental control (line 1). Seven independent transformed plants (lines 2–8) containing TBG4 antisense constructs were grown and allowed to self. Transformation (T-DNA insertion) was confirmed by southern analysis (data not shown). From each transformed line, five plants were grown along with 10 parental line plants. Fruit were tagged at the breaker stage ($1^{st}$ onset of color change) and were harvested at breaker plus 7 days. Data were taken using 15–20 fruit from each line. Each type of texture measurement was done twice for each fruit and fruit were subjected to 4 types of texture measurements using a Stable Micro System's TA-XT2i texture analyzer. The 4 measurements were; 1, 2-inch flat plate compression to 3 mm (FIG. 1A), 2, 4 mm spherical indenter compression to 3 mm (FIG. 11B), 3, 4 mm cylindrical indenter compression to 3 mm (FIG. 11C) and 4, 4 mm cylindrical indenter puncture to 10 mm (FIG. 11D). The summary of this data is shown in FIG. 11E(1-4). In FIGS. 11A–E (1-4) line 1 was the parental line and lines 2–8 each represent an independent transformant containing one T-DNA copy of the TBG4 antisense construct. Statistical analysis (Duncans and Scheffé) of the data revealed that fruit from the transformed lines 3, 7 and 8 were not significantly different from the parental line but that transformed lines 2, 4, 5 and 6 were significantly firmer than the parental fruit. Most noteworthy is that fruit from transformed line 2 had fruit with a mean firmness that was 40% firmer than that of the parental line (FIGS. 11A–D).

Northern Blot Analysis

We are currently investigating any changes in the biochemical composition of fruit where TBG4 mRNA levels have been suppressed. These experiments are designed to show a link between increased fruit firmness and TBG4 mRNA suppression, TBG4 encoded enzyme activity suppression, possible cell wall modification (e.g. increased galactosyl residue content) and a decrease in free galactose levels during fruit ripening.

These experiments are not complete, however some preliminary Northern blot experiments were done and the data is shown in FIGS. 12A,B. There is no parental or azygous control fruit RNA shown in FIGS. 12A,B because these plants were the last to grow, and RNA extractions are just being done now. As a comparison of normal fruit TBG4 mRNA levels refer to FIG. 5 above. The data from FIG. 5 showed that TBG4 mRNA levels are low at the mature green stage, peak at the turning stage and are reduced at the red stage. All the lines except for 2 and 3 expressed antisense TBG4 mRNA (FIGS. 12A,B). The antisense transcripts appear as two bands, smaller in length than the endogenous mRNA. The two bands probably resulted from 1, the expected transcriptional stop signal provided by the NOS-terminator and 2, a cryptic transcriptional stop signal in the antisense TBG4 cDNA. The most notable result was in line 2 where no TBG4 mRNA was detected at the turning stage. Line 2 also had the firmest red fruit (see FIGS. 11A–D). The absence of detectable TBG4 mRNA probably was the result of cosupression of both the endogenous and antisense mRNAs. When compared to earlier blots (e.g. FIG. 4), all of the lines appeared to have an overall reduced level of TBG4 mRNA, but it is impossible to assign numbers to this statement without the parental and azygous control RNA on the same Northern blot.

The specification discloses that β-galactosidase II polypeptide is involved in the degradation of cell wall pectin during fruit ripening. In the present invention, the role of β-galactosidases in tomato during fruit ripening and softening and the description of the cloning of a β-galactosidase cDNA clone that codes for a β(1→4)galactan degrading enzyme, which is expressed in ripening tomato fruit tissues, has been shown.

The present work indicates that pZBG2-1-4 is a cDNA derived from the transcript of the TBG4 gene which codes for β-galactosidase II for the following reasons:

First, the deduced amino acid sequence of the highly conserved amino-terminal portion of the expected mature pZBG2-1-4 translation product matches almost exactly (28 of 30 amino acids) with the amino-terminal sequence of β-galactosidase II as purified by Carey et al. (1995) and designated TOMAA. Importantly, the two amino acids (KY) in the β-galactosidase II sequence (TOMAA), that do not match the pZBG2-1-4 deduced amino acid sequence of the present invention are believed to be incorrect since all plant β-galactosidase sequences in the database and four additional β-galactosidase-related cDNAs that were identified from tomato all match or have conserved substitutions with the deduced amino acid sequence of pZBG2-1-4 at these same two amino acid (ST) positions (FIG. 3).

Second, the transcript detected by pZBG2-1-4 is present in normal ripening fruit at the same time that β-galactosidase II activity was detected (FIG. 5; Carey et al., 1995). Moreover, little or no transcript was detected in fruit at 45 and 50 dpa from the mutants nor, rin and Nr (FIG. 7). This observation also coincides with the data presented by Carey et al. (1995) that β-galactosidase II activity remained at levels equal to mature green fruit and did not rise in fruit 45–65 dpa from nor or rin plants. Interestingly, Carrington and Pressey (1996) have reported that β-galactosidase II activity was only detected in 'Rutgers' fruit after the turning stage of ripeness. The Northern data in the present invention indicates that maximum β-galactosidase II activity occurs only after the turning stage, assuming mRNA levels predict extractable enzyme activity (FIG. 5).

Third, the apparent molecular weight of 77.9 kD and pI of 8.9 for the mature protein predicted from the pZBG2-1-4 sequence is similar to that determined for β-galactosidase II., Pressey (1983), estimated a molecular weight of 62 kD by gel-filtration column chromatography and a pI of 7.8 by isoelectric focusing, while Carey et al. (1995) estimated a molecular weight of 75 kD by SDS-PAGE and a pI of 9.8 by isoelectric focusing.

Fourth, enzyme produced from pZBG2-1-4 ORF using a heterologous yeast expression system has both β-galactosidase activity and exogalactinase activity.

Literature Cited

Altschul S F, Gish W, Miller W, Meyers E W, Lipman D J (1990) Basic local alignment search tool. J Mol Biol 215:403–410

Ausubel F, Brent R, Kingston R, Moore D, Seidman J, Smith J, Struhl K, eds, (1987) Current Protocols in Molecular Biology. John Wiley and Sons, New York Carey A T, Holt K, Picard S, Wilde R, Tucker G A, Bird C R, Schuch W, Seymour G B (1995) Tomato exo-(1→4)-β-D-galactanase. Isolation, changes during ripening in normal and mutant tomato fruit, and characterization of a related clone. Plant Physiol 108:1099–1107

Carrington C M, Pressey R (1996) β-galactosidase II activity in relation to changes in cell wall galactosyl composition during tomato ripening. J Amer Soc Hort Sci 121:132–136

Church G M, Gilbert W (1984) Genomic sequencing. Proc Natl Acad Sci USA 81:1991–1995

DeVeau E J, Gross K C, Huber D J, Watada A E (1993) Degradation and solubilization of pectin by β-galactosidases purified from avocado mesocarp. Physiol Plant 87:279–285

Fischer R L, Bennett A B (1991) Role of cell wall hydrolases in fruit ripening. Annu Rev Plant Physiol Plant Mol Bio 42:675–703

Giovannoni J J, DellaPenna D, Bennett A B, Fischer R L (1989) Expression of a chimeric polygalacturonase gene in transgenic rin (ripening inhibitor) tomato fruit results in polyuronide degradation but not fruit softening. Plant Cell 1:53–63

Golden K D, John M A, Kean E A (1993) β-Galactosidase from *Coffea arabica* and its role in fruit ripening. Phytochemistry 34:355–360

Gross K C (1984) Fractionation and partial characterization of cell walls from normal and non-ripening mutant tomato fruit. Physiol Plant 62:25–32

Gross K C, Sams C E (1984) Changes in cell wall neutral sugar composition during fruit ripening: A species survey. Phytochemistry 23:2457–2461

Gross K C, Wallner S J (1979) Degradation of cell wall polysaccharides during tomato fruit ripening. Plant Physiol 63:117–121

Hall L N, Tucker G A, Smith C J S, Watson C F, Seymour G B, Bundick Y, Boniwell J M, Fletcher J D, Ray J A, Schuch W, Bird C R, Grierson D. (1993) Antisense inhibition of pectin esterase gene expression in transgenic tomatoes. Plant J 3:121–129

Huber D J (1983) The role of cell wall hydrolases in fruit softening. Hort Rev 5:169–219

Kang I K, Suh S G, Gross K C, Byun J K (1994) N-terminal amino acid sequence of persimmon fruit β-galactosidase. Plant Physiol 105: 975–979 Kim J, Gross K C, Solomos T (1991) Galactose metabolism and ethylene production during development and ripening of tomato fruit. Postharv Biol Technol 1:67–80

Marck C (1988) DNA Strider: a "C" program for the fast analysis of DNA and protein sequences on the Apple Macintosh family of computers. Nucleic Acids Res 16:1829–1836

Mitcham E J, Gross K C, Ng T J (1989) Tomato fruit cell wall synthesis during development and senescence. In vivo radiolabeling of cell wall fractions using [$^{14}$C] sucrose. Plant Physiol 89:477–481

Nakai K, Kanehisa M (1992) A knowledge base for predicting protein localization sites in eukaryotic cells. Genomics 14:897–911

Nielsen H, Engelbrecht J, Brunak S, von Heijne G (1997) Identification of prokaryotic and eukaryotic signal peptides and prediction of their cleavage sites. Protein Engineering 10:1–6

Pressey R (1983) β-Galactosidases in ripening tomatoes. Plant Physiol 71:132–135

Ross G S, Redgwell R J, MacRae E A (1993) Kiwifruit β-galactosidase: isolation and activity against specific fruit cell-wall polysaccharides. Planta 189:499–506

Ross G S, Wegrzyn T, MacRae E A, Redgwell R J, (1994) Apple β-galactosidase. Activity against cell wall polysaccharides and characterization of a related cDNA clone. Plant Physiol 106:521–528

Seymour G B, Gross K C (1996) Cell wall disassembly and fruit softening. Postharvest News Info 7:45N–52N Smith C J S, Watson C F S, Ray J, Bird C R, Morris P C, Schuch W, Grierson D (1988) Antisense RNA inhibition of polygalacturonase gene expression in transgenic tomatoes. Nature 334:724–726

Smith D L, Fedoroff N V (1995) LRP1, a gene expressed in lateral and adventitious root primordia of Arabidopsis. Plant Cell 7: 735–745

Smith D L, Starrett D A and Gross K C (1998) A gene coding for tomato fruit β-galatosidase II is expressed during fruit ripening. Plant Physiol. 117: 417–423

Tieman D M, Harriman R W, Ramamohan G, Handa A K (1992) An antisense pectin methylesterase gene alters pectin chemistry and soluble solids in tomato fruit. Plant Cell 4:617–679

Tigchelaar E C, McGlasson W B, Buescher R W (1978) Genetic regulation of tomato fruit ripening. HortScience 13:508–513

Turano F J, Thakkar S S, Fang T, Weisemann J M (1997) Characterization and expression of NAD(H) dependent glutamate dehydrogenase genes in *Arabidopsis thaliana*. Plant Physiol 113: 1329–1341

Verwoerd T C, Dekker B M M, Hoekema A (1989) A small-scale procedure for the rapid isolation of plant RNAs. Nuc Acids Res 17: 2362

Wegrzyn T F, MacRae E A (1992) Pectinesterase, polygalacturonase, and β-galactosidase during softening of ethylene-treated kiwifruit. HortScience 27:900–902

SEQUENCE LISTING

<160> NUMBER OF SEQ ID NOS: 14

<210> SEQ ID NO 1
<211> LENGTH: 3224
<212> TYPE: DNA
<213> ORGANISM: Lycopersicon esculentum

<400> SEQUENCE: 1

```
ttttttcttt gttcttttgc tcagcactag agcctagaag aaggaaaaaa agaagtatgg      60
actaatggaa taaacataaa aaagagagaa aaaaaaaaaa gaagaaaatt cttcagacaa     120
caaaaacagc tgtttcccct tcactacttt tttttccca atctctatat aattgcaaga     180
atagaataaa gtttgcaact tgattaaaaa aaaagaataa taagctgtgg gggtagggag     240
gaagttagtt cattagttca ttgccttgta aaggcacaat cttgattctt gatttgttga     300
caaatatggg ttttggatg gcaatgttgc tgatgttgtt attgtgttta tgggtttctt      360
gtggaattgc ttctgtttca tatgaccata aagctatcat tgtaaatgga caagaaaaa     420 ttctcatttc tggatccatt cactacccta gaagcacccc tgagatgtgg ccagatctta     480
ttcagaaggc aaaagaaggg ggagttgatg ttatacagac ttatgttttc tggaatgggc     540
atgagcctga agaagggaaa tattattttg aagagaggta tgatttagtg aagttcatta     600
aagtggtgca agaagcagga cttatgtgc atcttaggat tggaccttat gcatgtgctg     660
aatggaattt tgggggtttt cctgtttggc tgaagtatgt tccaggtatt agtttcagaa     720
caaacaatga gccattcaag gctgcaatgc aaaagttcac tactaagatt gttgatatga     780
tgaaagcaga aaagctctat gaaactcagg gtggtccaat tattctatct cagatagaaa     840
atgaatatgg acctatggag tgggaactag gtgaacctgg taaagtttac tcagaatggg     900
cagccaaaat ggctgtggat cttggcactg gtgtcccatg gatcatgtgc aagcaagatg     960
atgtccctga tcctattatt aatacttgca atggtttcta ctgtgactac ttcacaccaa    1020
ataaggctaa taaacccaag atgtggactg aagcctggac tgcctggttt accgaatttg    1080
gaggtccagt tccttaccgt cctgcagagg atatggcatt tgctgtcgca agatttatac    1140
```

```
aaacgggagg ctccttcatc aattactata tgtatcatgg aggaacaaac tttggaagga    1200
cttctggtgg cccatttatt gctactagtt atgattatga tgcaccccta gatgaatttg    1260
ggtcattacg gcagcctaaa tggggtcatc tgaaagatct acatagagca ataaagctct    1320
gtgagccagc tttagtatct gtagatccaa ctgtgacatc cttaggaaac tatcaagagg    1380
cacgtgtttt caagtcagag tctggggcct gcgctgcctt cctagcaaat tacaaccagc    1440
actcttttgc taaagtggca tttgggaaca tgcattataa cttgccaccc tggtctatca    1500
gcattcttcc cgactgcaag aacactgtct ataatactgc aagggttggt gctcaaagtg    1560
ctcagatgaa gatgactcca gtcagtagag gattctcatg ggagtcattc aatgaagacg    1620
cagcatcgac tgaagacgac actttcacag ttgttgggtt attggagcag attaatatca    1680
caagagatgt atctgattac ttgtggtata tgactgacat tgagattgat ccaacagaag    1740 gattttttgaa tagtggaaat tggccttggc ttactgtctt ttctgctggc catgcattgc    1800
atgtattcgt gaatggtcaa ttagcaggaa ctgtgtacgg aagtttagaa acccaaaac     1860 taactttcag caacggtata aatctgagag ctggtgtgaa caagatttct ctgctaagca    1920
ttgctgttgg tcttccgaac gttggccctc attttgagac atggaatgct ggtgttcttg    1980
gaccagtttc acttaatgsa cttaatgaag gaacaagaga tttaacatgg cagaaatggt    2040
tctacaaggt tggtctaaaa ggagaagccc tgagtcttca ttcactcagt ggtagcccat    2100
ccgtggagtg ggtggaaggc tctttagtgg ctcagaagca gccactcagt tggtataaga    2160
ctacattcaa tgctccagat ggaaatgaac ctttggcttt agatatgaat accatgggca    2220
aaggtcaagt atggataaat ggtcagagcc tcggacgcca ctggcctgca tataaatcat    2280
ctggaagttg tagtgtctgt aactatactg gctggtttga tgagaaaaag tgcctaacta    2340
actgtggtga gggctcacaa agatggtacc acgtaccccg gtcttggctg tatcctactg    2400
gaaatttgtt agttgtattc gaggaatggg gaggagatcc ttatgaatc actttagtca    2460 aaagagaaat agggagtgtt tgtgctgata tatatcagtg gcaaccacag ttattgaatt    2520
ggcagaggct agtatctggt aagtttgaca gacctctcag acctaaagcc catcttaagt    2580
gtgcacctgg tcagaagatt tcttcaatca aatttgcaag ctttggaaca ccagagggag    2640
tttgtgggaa cttccagcag ggaagctgcc atgctccgcg ctcatatgat gctttcaaaa    2700
agaattgtgt tgggaaagag tcttgctcag tacaggtaac accagagaat tttggaggtg    2760
atccatgtcg aaacgttcta aagaaactct cagtggaagc catttgtagt tgatgattct    2820
gagtatacaa gtgaaaaaat acttgaacca ctcatataaa cattttttcaa acgagctact    2880 agacatccat taacccacac taccattttt tggctttgct ggggttgaag ttgtacagtt    2940
aagcaacaca cctctttgat caaagctcac ctgattatga agatgattga cgaaagattc    3000
tgtacatgta aggtttcgtc taattacaca tacagatatg attcttgatg aatcgatgtg    3060
caaattttgt ttgtgttagg gtgagagaga cttgaaaagc attttgcttt catgatgttc    3120
tacattatac aatcataatg taagtaagca agcaataatt cattgctttg cacattgaaa    3180
aatgcatttt actatgttgc agtacaaaaa aaaaaaaaa aaaa                      3224

<210> SEQ ID NO 2
<211> LENGTH: 2984
<212> TYPE: DNA
<213> ORGANISM: Lycopersicon esculentum

<400> SEQUENCE: 2
ggagcagaag aaaaacactg aatttttccgt taatactaac ggtgttaact atccactttg      60
```

-continued

| | | | | |
|---|---|---|---|---|
| tgatcgtcgc | cggcgagtat | ttcaagccgt | tcaatgtcac | ctacgataac cgagctctca | 120 |
| tcatcggcgg | taaacgccgt | atgcttatct | ccgccggaat | tcactaccct cgcgccactc | 180 |
| ctgagatgtg | gcccacattg | atagctagga | gcaaagaagg | tggtgcagat gtcatcgaga | 240 |
| cttatacatt | ttggaatggt | catgagccaa | ccaggggaca | gtacaatttt gaaggaagat | 300 |
| atgatattgt | caagttcgca | aagctagtcg | gatctcatgg | actgttcctc tttattcgaa | 360 |
| taggtcctta | tgcctgtgca | gaatggaact | tcggggatt | ccccatatgg cttcgtgata | 420 |
| tacctggaat | agaatttcga | acagataatg | caccattcaa | ggaggagatg gagcgctatg | 480 |
| ttaaaaagat | agttgatctt | atgatatctg | agtcgctctt | ttcgtggcaa ggtggtccta | 540 |
| tcattttgct | gcagattgaa | aatgaatatg | gaaatgttga | aagctcattc ggtcccaagg | 600 |
| ggaagttata | tatgaaatgg | gctgctgaaa | tggctgttgg | tcttggtgct ggtgttccat | 660 |
| gggtcatgtg | caggcaaact | gatgctccag | aatacatcat | agatacttgt aatgcatact | 720 |
| attgtgatgg | gttcacgccg | aattccgaga | agaaaccgaa | aatttggact gagaattgga | 780 |
| atggatggtt | tgcagattgg | ggtgaaagac | ttccatatag | accttccgag gatattgcat | 840 |
| ttgcaattgc | tcgtttcttt | caacgtgggg | gcagcttaca | gaactattat atgtattttg | 900 |
| gtgggacaaa | ttttgccgg | actgctggtg | gcccaactca | aatcactagc tatgattatg | 960 |
| atgctccact | ggatgaatat | ggactactac | gtcaacctaa | atggggccat ttgaaggatc | 1020 |
| tgcatgctgc | tataaagctt | tgtgaaccag | ctcttgttgc | tgctgattca cctcagtata | 1080 |
| ttaaactggg | accaaaacag | gaggcacatg | tctatcgtgg | aacatccaac aacattggcc | 1140 |
| aatatatgtc | cttaaatgaa | ggcatatgcg | cagcatttat | tgcaaatatt gatgaacatg | 1200 |
| aatcagcaac | agtgaaattt | tacggtcaag | agttcacttt | acctccatgg tcagtggtat | 1260 |
| tctgccagat | tgcagaaata | cagctttcaa | cacagctaag | gtgggggcac aaacttcaat | 1320 |
| caaaacagtg | ggctcagatt | ctgtttcagt | tgggaataat | tctttctttc tacaagttat | 1380 |
| cactaaaagc | aagctcggaa | agttttttcac | aatcttggat | gacattgaag gagccacttg | 1440 |
| gtgtgtgggg | tgacaagaat | ttcacttcta | aggaatact | ggagcatctg aatgtgacaa | 1500 |
| aagaccagtc | tgattacctg | tggtatctga | ccaggatata | tatttctgat gatgacatct | 1560 |
| cattttggga | ggaaaatgat | gttagtccaa | caattgatat | tgatagcatg cgtgattttg | 1620 |
| ttcgcatttt | tgttaatggg | cagcttgcag | gtagtgtgaa | aggcaaatgg atcaaggtgg | 1680 |
| ttcaacctgt | taagctggtt | cagggataca | acgacatact | gctattatct gagacggtgg | 1740 |
| gattgcagaa | ttatggtgcc | ttcttggaga | aggatggggc | aggttttaaa ggtcagataa | 1800 |
| agcttacagg | atgcaaaagc | ggggatatca | atctcacaac | atctttatgg acctaccagg | 1860 |
| tggggcttag | aggcgaattc | ctggaagtat | atgatgtcaa | tagtactgaa agtgcaggat | 1920 |
| ggactgagtt | tcccactggt | acaactccgt | cagtcttttc | gtggtacaag acaaagtttg | 1980 |
| atgccccagg | cgggacagat | ccagttgctc | ttgattttag | tagcatggga aaaggtcagg | 2040 |
| catgggttaa | tggccaccat | gtaggaagat | attggacttt | ggttgcacca ataatggat | 2100 |
| gtggaagaac | ttgtgattat | cgtggtgctt | accactctga | taaatgtagg acaaactgtg | 2160 |
| gagagattac | tcaggcctgg | taccatatac | ctagatcatg | gctaaagaca ttaaataatg | 2220 |
| tactagttat | ctttgaagaa | acagataaaa | ctccgtttga | tatttccatt tctacgcgtt | 2280 |
| ctactgaaac | catttgtgct | caagtatcgg | aaaagcacta | tccacctcta cataagtggt | 2340 |
| ctcattcgga | gtttgacaga | aagttgtctc | tgatggataa | aacaccagaa atgcacttgc | 2400 |

-continued

```
agtgtgacga aggacataca atctcttcta ttgaatttgc aagctatgga agtccgaatg    2460
gcagctgtca aaagttctca aaggaaaat gccatgctgc aaattccttg tctgttgtat    2520
ctcaggcttg tataggaaga actagttgca gcattggcat ttccaatggt gtatttggag    2580
atccatgtcg acacgttgtg aagagtttgg ctgttcaagc aaaatgctca ccaccaccag    2640
acctcagcac ttcagcttcc tcgtgaggag actctggtaa cacgttaacc ttttagaacg    2700
aaacgatccc ttaaagtcca ctcgttcccc tgccccgag ccctctgcta catttctcag    2760
atcgcatcgt tacaatcagg cggagaaaac gtacatggac gattttactt gtaaatattt    2820
ggttactgta tataaatga aaggaataat gttgcttatg catatgagct gcaaattata    2880
tgacaaagta acaaatgaaa atagaaaact cctgtctgtc aaagaattt aacaacacca    2940 tttattaaaa gttagttaac atgattaaaa aaaaaaaaa aaaa                    2984
```

<210> SEQ ID NO 3
<211> LENGTH: 3069
<212> TYPE: DNA
<213> ORGANISM: Lycopersicon esculentum

<400> SEQUENCE: 3

```
agagttcatt attttttttg cattttgaaa agaggaaaa aaataaagtt aaggggggg      60 gaaaaagttt tcattttgcc ttaaaaaggc acaatcttga tagaaaagga gataatttta    120
catgggttgt acgcttatac taatgttgaa tgtgttgttg gtgttgttgg gttcatgggt    180
tttttctgga acagcttctg tttcatatga ccataggct attattgtaa atggacaaag     240
aagaatactt atttctggtt ctgttcatta tccaagaagc actcctgaga tgtggccagg    300
tattattcaa aaggctaaag aaggaggtgt ggatgtgatt cagacttatg ttttctggaa    360
tggacatgag cctcaacaag ggaaatatta ttttgaaggg agatatgatt tagtgaagtt    420
tattaagctg gtgcaccaag caggactta tgtccatctt agagttggac cttatgcttg    480
tgctgaatgg aattttgggg gctttcctgt ttggctgaaa tatgttccag gtatcagttt    540
cagaacagat aatggacctt tcaaggctgc aatgcaaaa tttactgcca agattgtcaa    600
tatgatgaaa gcggaacgtt tgtatgaaac tcaagggggg ccaataattt tatctcagat    660
tgagaatgaa tatggaccca tggaatggga actgggagca ccaggtaaat cttacgcaca    720
gtgggccgcc aaaatggctg tgggtcttga cactggtgtc ccatgggtta tgtgcaagca    780
agacgatgcc cctgatccta ttataaatgc ttgcaatggc ttctactgtg actacttttc    840
tccaaacaag gcttataaac caaagatatg gactgaagcc tggactgcat ggtttactgg    900
ttttggaaat ccagttcctt accgtcctgc tgaggacttg gcattttctg ttgcaaaatt    960
tatacagaag ggaggttcct tcatcaatta ttacatgtat catggaggaa caaacttgg    1020 acggactgct ggtggtccat ttattgctac tagttatgac tatgatgcac cacttgatga    1080
atatggatta ttgcgacaac caaaatgggg tcacctgaaa gatctgcata gagcaataaa    1140
gctttgtgaa ccagctttag tctctggaga tccagctgtg acagcacttg acaccagca    1200 ggaggcccat gttttaggt cgaaggctgg ctcttgtgct gcattccttg ctaactacga    1260
ccaacactct tttgctactg tgtcatttgc aaacaggcat acaacttgc catggtggtc    1320 aatcagcatt cttcccgact gcaagaacac tgtatttaat acagcacgga tcggtgctca    1380
aagtgctcag atgaagatga ctccagtcag cagaggattg ccctggcagt cattcaatga    1440
agagacatca tcttatgaag acagtagttt tacagttgtt gggctattgg aacagataaa    1500
tacaacaaga gacgtgtctg attatttgtg gtattcaaca gatgtcaaga ttgattcaag    1560
```

-continued

```
agaaaagttt tgagaggcg gaaaatggcc ttggcttacg atcatgtcag ctgggcatgc    1620
attgcatgtt tttgtgaatg gtcaattagc aggaactgca tatggaagtt tagaaaaacc    1680
gaaactaact ttcagtaaag ccgtaaatct gagagcaggt gttaacaaga tttctctact    1740
gagcattgct gttggccttc cgaatatcgg cccacatttt gagacatgga atgctggtgt    1800
tcttgggcca gtctcactaa ctggtcttga cgagggggaaa agagatttaa catggcagaa    1860
atggtcttac aaggttggtc taaaaggaga agccttgagc ctccattcac tcagtggtag    1920
ctcgtcagtt gagtgggtcg agggttcttt agtggctcag agacagccac tcacatggta    1980
caagagcact tttaatgctc cagctggaaa tgatcctttg gctttagact tgaataccat    2040
gggcaaagga caagtgtgga taaatggtca agcctcggac cgctattggc ctggatataa    2100
agcatctggt aactgcggtg cctgtaacta tgcaggctgg tttaatgaga aaaaatgcct    2160
aagtaactgt ggagaggctt cacaacgatg gtatcatgtt ccccgttctt ggctgtatcc    2220
tactggaaat ttgttagttc tatttgagga atggggagga gagcctcatg gaatctcttt    2280
ggtaaaaaga gaagttgcaa gtgtttgtgc agatataaac gaatggcaac cacagttggt    2340
gaattggcaa atgcaagcat ctggtaaagt tgacaaacca ctgagaccta aagctcacct    2400
ctcgtgtgct tctggtcaga agattacttc aatcaaattt gcaagctttg gaccaccaca    2460 agggggtctgc ggaagcttcc gtgaaggaag ctgccacgcc ttccactcat atgatgcttt    2520
tgaaaggtat tgcatcgggc aaaactcgtg ctcagtacct gtaacaccag agatctttgg    2580
aggtgatcca tgtccacatg ttatgaagaa actctcagtt gaggttattt gcagttgatg    2640
acactgagga gaaacaaata aaagtggttt cagttagttg tctgaacata tcaaaaagtt    2700
ggctttgatg gaggtgaagt tgtacagata tgcaacacac ctttccattt gaggcacata    2760
tgaattgcaa tggcccaaga ttctgtacat atatgttggt tactgtcaag ttggtattgg    2820
tttgcaaatg taaaacagta gtatagtcat tggttcaagt gcgcatcgag attgtgctag    2880
tgggaggtag taggtaccga tcgatctatc gttgtttgca caagctgggc ctagattcca    2940
ctattattat aacaaagaaa gcacaatgag actgattctt gattagtcca tgtgtagata    3000
ttgttactgt tggatttgca aatcttgtga tttcagcaaa aaaaaaaaaa aaaaaaaaa    3060 aaaaaaaaa                                                             3069
```

<210> SEQ ID NO 4
<211> LENGTH: 2554
<212> TYPE: DNA
<213> ORGANISM: Lycopersicon esculentum

<400> SEQUENCE: 4

```
aaaaaaagtt tcaatttttt ttctaaaata aaaaaaaatt catttttttt gaatgtggaa      60
aaaatgctaa ggactaatgt gttgttgtta ttagttattt gttattgga ttttttttct      120 tcagtgaaag ctagtgtttc ttatgatgac agagctataa tcataaatgg gaaaagaaaa     180
attcttattt ctggttcaat tcattatcca agaagcactc cacagatgtg gcctgatctt     240
atacaaaagg ctaaagatgg aggcttagat gttattgaaa cttatgtttt ctggaatgga     300
catgagcctt ctcctggaaa atataatttt gaaggaagat atgatcttgt tagattcatc     360
aaaatggtac aaagagcagg actttatgtc aatttacgta ttggcccttta cgtctgtgct     420 gaatggaact ttgggggatt ccctgtttgg ctaaaatatg tgcctggtat ggaatttaga     480
acaaacaatc agcctttttaa ggtggctatg caaggatttg ttcagaaaat agtcaacatg     540
```

-continued

```
atgaagtcag aaaatttgtt tgaatctcaa ggaggaccaa taattatggc ccagatacaa      600
aatgagtatg gaccagtaga atgggaaatt ggtgctcctg gtaaagctta tacaaaatgg      660
gcagctcaaa tggctgtagg tttgaaaact ggtgtcccat ggatcatgtg taagcaagag      720
gatgctcctg atcctgtgat tgatacttgt aatggcttct actgcgaagg gttccgtcct      780
aataagcctt acaaacctaa aatgtggaca gaagtatgga ctggctggta tacgaaattc      840
ggtggtccaa ttcctcaaag accagccgaa gacattgcat tttcagttgc caggtttgtt      900
cagaacaatg gttcattctt caattactac atgtatcatg gaggaacaaa ttttggccgg      960
acatcatcag ggcttttcat tgcaactagc tacgattatg atgctcctct cgatgaatat     1020
gggttgctga atgaaccaaa gtatgggcac ttgagagact tacataaagc tatcaagcta     1080
tctgaaccgg ctttagtttc atcatatgct gcggtgacta gtcttggaag taatcaagag     1140
gctcatgttt atagatcaaa atctggagct tgtgctgctt ttttatccaa ctatgactct     1200
agatattcag taaagtcac ctttcagaat aggccataca atctgcctcc atggtccatc     1260
agcattcttc ccgactgcaa aactgccgtt acaacactg cacaggttaa ctctcaaagc     1320
tcgagcataa agatgacgcc tgcaggtggt ggattctctt ggcagtcata caatgaagaa     1380
acgcctactg ctgatgacag cgatacactt acagctaacg gactatggga acagaaaaac     1440
gtcacaagag attcatcaga ctatctgtgg tacatgacaa atgtaaatat agcatctaat     1500
gaaggatttc taaagaacgg aaaggatcct tatctcactg ttatgtccgc tggtcatgtc     1560
ttgcatgttt tcgtcaatgg aaaactatca ggaactgttt atggtacatt ggataatcca     1620
aaacttacat acagtggcaa cgtgaagtta agagctggta ttaacaagat ttctctgctc     1680
agtgtttccg ttggtctccc gaacgttggc gtgcattatg atacatggaa tgcaggagtt     1740
ctaggtccag tcacgttgag cggtctcaat gaagggtcaa gaaacttggc gaaacagaaa     1800
tggtcttaca aggttggtct gaaaggcgaa tcgttaagtc ttcactcctt aagtgggagt     1860
tcttctgttg aatgggttcg aggttcacta atggctcaaa gcagcccct gacttggtac     1920 aaggctacat ttaacgcgcc tggaggaaat gatccactag ctttagacat ggcaagtatg     1980
ggaaaaggtc agatatggat aaatggtgaa ggcgtaggtc gccattggcc tggatacata     2040
gcacaaggcg actgcagcaa atgcagttat gctggaacgt tcaacgagaa gaagtgcgga     2100
actaactgcg gacaaccttc tcagagatgg taccatgttc cacgatcgtg gctgaaacca     2160
agtggaaact tgttagtagt attcgaagaa tggggaggta atccaacagg aatttctcta     2220
gtcaggagat caagataaag aactcgaaaa gtaaaacttg ttcagtaact atggtgcttg     2280
aattcgcgcc gaaaaataca tacacgaagc taacaatgga ggctacagtt tgcaaattgc     2340
agctgaataa aacattagaa gataaagaaa tatttgatta aaaggagtat ataaatttac     2400
agagaatttt ctttattctt tgtaaaactt tggtttataa agtttataca gaattttctg     2460
ttatttggat tatgagattg aagaagattg tacagcttcc aaatactatt agaatacaaa     2520
taaatttcat gtaaaaaaaa aaaaaaaaaa aaaa                                 2554
```

<210> SEQ ID NO 5
<211> LENGTH: 755
<212> TYPE: DNA
<213> ORGANISM: Lycopersicon esculentum

<400> SEQUENCE: 5

```
atccagactt acgttttctg gaaccttcat gaacctgttc gaaatcagta tgattttgaa       60
ggaaggaaag atttgattaa ttttgtgaag ttggtggaga gagctggctt atttgttcat      120
```

```
ataaggattg ggccttatgt ttgtgcagaa tggaactatg gtgggtttcc tctttggttg      180
catttcattc ctggaattga atttcgaacc gacaatgaac cgttcaaggc agaaatgaag      240
cgattcacag ctaaaattgt tgacatgatc aagcaagaaa atctatatgc atcccagggt      300
gggccggtta tcttgtctca gatagaaaat gagtatggca atggtgatat tgagtctcgt      360
tatggtcctc gtgccaaacc ttacgtgaac tgggcagcat caatggctac gtctttaaat      420
acgggagtgc catgggttat gtgtcagcaa ccagatgccc ctccttccgt tattaacact      480
tgcaatggat tttattgtga ccaattcaag caaaattccg ataaaacacc caagatgtgg      540
actgagaatt ggaccggatg gtttctgtcg tttggtggtc ctgtcccta cagaccagtg      600 gaagacatcg ctttcgctgt ggctcgattt tccagcgag gcggaacttt ccagaactat       660
tacatgtacc acggggaac taactttggg agaaccagtg gtggaccgtt tattgcaact       720
agctatgact atgatgcccc tctcgacgaa tacgg                                 755
```

```
<210> SEQ ID NO 6
<211> LENGTH: 749
<212> TYPE: DNA
<213> ORGANISM: Lycopersicon esculentum

<400> SEQUENCE: 6
atccagacat atgttttttg gaatgttcat gagccttctc ctggcaatta caattttgaa      60
ggaagatatg acctggtgag gtttgtaaaa acgattcaga aagcagggct gtatgctcat      120
cttcgaattg gccccttacgt ttgtgcagag tggaattttg gagggtttcc agtatggctg     180
aagtatgtac ctggcattag cttcagagct gataatgaac cttttcaagaa cgcaatgaaa    240 gggtatgctg agaaaattgt taacttgatg aagatcataa tcttttcgag tctcagggtg     300
gtccaatcat actctcacag attgagaatg agtatgggcc tcaagccaag gtacttggag     360
caccgggaca tcagtattca acatgggctg caaatatggc agttggattt gaacacaggc     420
gtccatgggg tgatgtgcaa ggaagaagat gcaccagatc ctgtgatcaa cacatgcaat     480
ggtttctact gtgataattt cttcccaaac aaaccataca aacctgcaat ttggactgaa     540
gcttggagtg gatggttctc ggaatttggc ggtccccttc atcagagacc agttcaggat     600
ttggcatttg ctgttgccca atttatacaa agaggaggat cttttgttaa ctattacatg     660
tacatggggg gcacgaactt tggacgcact gcgggtgggc cattcatcac taccagctat     720
gattatgatg ccccccctcga cgagtatgg                                       749
```

```
<210> SEQ ID NO 7
<211> LENGTH: 2972
<212> TYPE: DNA
<213> ORGANISM: Lycopersicon esculentum

<400> SEQUENCE: 7
gcaacttctc cggtgaataa caccggtaaa cggccaatgc caactctcgt cggaatctga      60
atagtgattt aagcagctta gctagctaac ttttgcctct gcaatgaaca caatgagttg      120
tttgtcctct aatttcaagt tcgttttcct tgcctcgact gtgatatgga tgacggtaat      180
gtcgtcgtcg ttagcagcag tagatgcttc caatgttact actattcgta ctgatagtgt      240
gacttacgat cgacgctcgt tgattattaa cggccagagg aagctgctca tctccgcttc      300
cattcactat cctcgcagtg tccctgccat gtggcctggt ctggttcgat tggcgaagga      360
aggaggagtg gatgttattg aaacgtatgt tttctggaac ggtcacgaac cttctccggg      420
```

-continued

| | |
|---|---|
| caattattac tttggaggaa ggtttgatct agtcaaattt tgtaagatca ttcagcaggc | 480 |
| tggaatgtat atgattcttc ggattggacc atttgtagct gcagaatgga actttggtgg | 540 |
| acttcctgtg tggttgcatt atgtgccagg taccacctttt cggactgata gtgaaccatt | 600 |
| taagtatcac atgcagaagt tcatgacata tacagtgaac ttaatgaaga gagagaggct | 660 |
| ttttgcatct caaggaggtc caatcatctt gtcacaggta gaaaatgagt acggctacta | 720 |
| tgaaaatgca tatggagaag gagggaaaag gtatgcctta tgggctgcta aaatggccct | 780 |
| ttctcaaaat actggtgtac cttggataat gtgccagcag tatgatgctc ctgatcctgt | 840 |
| gattgacaca tgcaattcat tttactgcga ccaatttaaa ccaatctctc caaacaagcc | 900 |
| caaaatttgg acagagaact ggccgggatg gttcaagaca tttggggcca gagatcctca | 960 |
| caggcctcac gaagatgttg cttattccgt ggctcgtttt ttccaaaaag gaggaagcgt | 1020 |
| gcagaattat tacatgtacc atggtgggac gaactttggc aggacagcag gtggcccttt | 1080 |
| cattaccaca agttatgact atgatgcccc aattgacgaa tatggtttac caaggtttcc | 1140 |
| aaaatgggt caccttaaag aacttcataa agtcataaaa tcgtgtgagc atgctctgct | 1200 |
| gaacaatgat ccaactcttc tttcattagg tcctctacaa gaggctgatg tttatgaaga | 1260 |
| tgcttcaggc gcttgtgctg ccttttctcgc gaatatggat gacaaaaatg caaggtggt | 1320 |
| acagttccga catgtatcat accacttgcc agcatggtct gttagcattt tgccagactg | 1380 |
| caaaaatgta gcgttcaaca cagcaaaggt tggatgtcaa acttctattg tcaatatggc | 1440 |
| acccatagat ttgcatccca ccgcaagttc accaaagaga gacatcaagt ctcttcagtg | 1500 |
| ggaagtcttc aaggaaacag ctggagtatg ggcagttgct gatttcacta aaaacggatt | 1560 |
| tgtagatcac attaacacca caaaagatgc tacagactac ctctggtaca caacaagtat | 1620 |
| ttttgttcat gcagaggagg atttcctaag aaacagaggc actgcaatgc ttttcgttga | 1680 |
| atcaaagggt catgctatgc atgtcttcat caataaaaag cttcaagcca gtgcatctgg | 1740 |
| aaatggcaca gtgccacagt tcaagtttgg aactcctatt gctctaaagg cagggaagaa | 1800 |
| tgaaatttcc ttgttaagca tgactgtggg cctacaaaca gctggagcgt tttatgaatg | 1860 |
| gattggagct ggtccaacaa gtgtcaaagt tgcagggttc aagactggga ctatggactt | 1920 |
| gactgcgtct gcttggacct ataagattgg attgcaagca gaacatttga ggatacagaa | 1980 |
| gtcatataac ttgaagagta aaatttgggc accaacttcg cagccaccaa agcaacagcc | 2040 |
| cctcacatgg tataaggcag tagtagatgc gcctcctggt aatgaacctg ttgcacttga | 2100 |
| tatgattcat atgggaaaag gaatggcttg gttgaatgca caagaaattg gcagatattg | 2160 |
| gccgaggaga acttctaaat atgagaattg tgttactcaa tgtgactaca gagccaaatt | 2220 |
| taaccctgat aagtgtgtca ctggctgtgg acaacctaca cagagatggt atcatgtgcc | 2280 |
| acgatcttgg ttcaagccat caggaaatgt cttaattatc tttgaggaaa taggtggaga | 2340 |
| tccctctcaa attagattct caatgcgaaa ggtttctgga gcttgtggtc atctttcagt | 2400 |
| ggaccatcca tcctttgatg ttgaaaatct gcaagcaagt gaaattgaga cgacaaaaa | 2460 |
| cagcccaact ctaagtttca atgccccac aaatactaat atttcctctg tcaaatttgc | 2520 |
| cagctttgga atcctaatg gtacatgtgg ctcctacatc ctaggagact gccacgatca | 2580 |
| gaattctgca gcactggtcg aaaaggtttt cctgaaccaa aatgagtgtg cattagaaat | 2640 |
| gtccagcgca aactttaaca tgcaattgtg tccaagtaca gtaaagaaac ttgcagttga | 2700 |
| agtgaattgc agctgagtgt cattgcccaa aatgaatgac atattctaat ttatatagtt | 2760 |
| tgctacggag atgctcattc ttaaaccttt cttatatagc agaaaaatct gctattcctt | 2820 |

-continued

```
ctttcgtcta tgatttgaag tttaagatat gagtactgat gtcttattaa gcatcaccag    2880
ataaccttgg atattcatgt ttgaaagact aagtattcat atttattcag tcgagatgca    2940
agatttattt gtgaaaaaaa aaaaaaaaaa aa                                  2972
```

<210> SEQ ID NO 8
<211> LENGTH: 835
<212> TYPE: PRT
<213> ORGANISM: Lycopersicon esculentum

<400> SEQUENCE: 8

```
Met Gly Phe Trp Met Ala Met Leu Leu Met Leu Leu Leu Cys Leu Trp
 1               5                  10                  15

Val Ser Cys Gly Ile Ala Ser Val Ser Tyr Asp His Lys Ala Ile Ile
            20                  25                  30

Val Asn Gly Gln Arg Lys Ile Leu Ile Ser Gly Ser Ile His Tyr Pro
        35                  40                  45

Arg Ser Thr Pro Glu Met Trp Pro Asp Leu Ile Gln Lys Ala Lys Glu
    50                  55                  60

Gly Gly Val Asp Val Ile Gln Thr Tyr Val Phe Trp Asn Gly His Glu
65                  70                  75                  80

Pro Glu Glu Gly Lys Tyr Tyr Phe Glu Arg Tyr Asp Leu Val Lys
                85                  90                  95

Phe Ile Lys Val Val Gln Glu Ala Gly Leu Tyr Val His Leu Arg Ile
            100                 105                 110

Gly Pro Tyr Ala Cys Ala Glu Trp Asn Phe Gly Gly Phe Pro Val Trp
        115                 120                 125

Leu Lys Tyr Val Pro Gly Ile Ser Phe Arg Thr Asn Asn Glu Pro Phe
    130                 135                 140

Lys Ala Ala Met Gln Lys Phe Thr Thr Lys Ile Val Asp Met Met Lys
145                 150                 155                 160

Ala Glu Lys Leu Tyr Glu Thr Gln Gly Gly Pro Ile Ile Leu Ser Gln
                165                 170                 175

Ile Glu Asn Glu Tyr Gly Pro Met Glu Trp Glu Leu Gly Glu Pro Gly
            180                 185                 190

Lys Val Tyr Ser Glu Trp Ala Ala Lys Met Ala Val Asp Leu Gly Thr
        195                 200                 205

Gly Val Pro Trp Ile Met Cys Lys Gln Asp Asp Val Pro Asp Pro Ile
    210                 215                 220

Ile Asn Thr Cys Asn Gly Phe Tyr Cys Asp Tyr Phe Thr Pro Asn Lys
225                 230                 235                 240

Ala Asn Lys Pro Lys Met Trp Thr Glu Ala Trp Thr Ala Trp Phe Thr
                245                 250                 255

Glu Phe Gly Gly Pro Val Pro Tyr Arg Pro Ala Glu Asp Met Ala Phe
            260                 265                 270

Ala Val Ala Arg Phe Ile Gln Thr Gly Gly Ser Phe Ile Asn Tyr Tyr
        275                 280                 285

Met Tyr His Gly Gly Thr Asn Phe Gly Arg Thr Ser Gly Gly Pro Phe
    290                 295                 300

Ile Ala Thr Ser Tyr Asp Tyr Asp Ala Pro Leu Asp Glu Phe Gly Ser
305                 310                 315                 320

Leu Arg Gln Pro Lys Trp Gly His Leu Lys Asp Leu His Arg Ala Ile
                325                 330                 335

Lys Leu Cys Glu Pro Ala Leu Val Ser Val Asp Pro Thr Val Thr Ser
```

```
                340                 345                 350
Leu Gly Asn Tyr Gln Glu Ala Arg Val Phe Lys Ser Glu Ser Gly Ala
            355                 360                 365
Cys Ala Ala Phe Leu Ala Asn Tyr Asn Gln His Ser Phe Ala Lys Val
    370                 375                 380
Ala Phe Gly Asn Met His Tyr Asn Leu Pro Pro Trp Ser Ile Ser Ile
385                 390                 395                 400
Leu Pro Asp Cys Lys Asn Thr Val Tyr Asn Thr Ala Arg Val Gly Ala
                405                 410                 415
Gln Ser Ala Gln Met Lys Met Thr Pro Val Ser Arg Gly Phe Ser Trp
            420                 425                 430
Glu Ser Phe Asn Glu Asp Ala Ala Ser His Glu Asp Thr Phe Thr
        435                 440                 445
Val Val Gly Leu Leu Glu Gln Ile Asn Ile Thr Arg Asp Val Ser Asp
    450                 455                 460
Tyr Leu Trp Tyr Met Thr Asp Ile Glu Ile Asp Pro Thr Glu Gly Phe
465                 470                 475                 480
Leu Asn Ser Gly Asn Trp Pro Trp Leu Thr Val Phe Ser Ala Gly His
                485                 490                 495
Ala Leu His Val Phe Val Asn Gly Gln Leu Ala Gly Thr Val Tyr Gly
            500                 505                 510
Ser Leu Glu Asn Pro Lys Leu Thr Phe Ser Asn Gly Ile Asn Leu Arg
        515                 520                 525
Ala Gly Val Asn Lys Ile Ser Leu Leu Ser Ile Ala Val Gly Leu Pro
    530                 535                 540
Asn Val Gly Pro His Phe Glu Thr Trp Asn Ala Gly Val Leu Gly Pro
545                 550                 555                 560
Val Ser Leu Asn Gly Leu Asn Glu Gly Thr Arg Asp Leu Thr Trp Gln
                565                 570                 575
Lys Trp Phe Tyr Lys Val Gly Leu Lys Gly Glu Ala Leu Ser Leu His
            580                 585                 590
Ser Leu Ser Gly Ser Pro Ser Val Glu Trp Val Glu Gly Ser Leu Val
        595                 600                 605
Ala Gln Lys Gln Pro Leu Ser Trp Tyr Lys Thr Thr Phe Asn Ala Pro
    610                 615                 620
Asp Gly Asn Glu Pro Leu Ala Leu Asp Met Asn Thr Met Gly Lys Gly
625                 630                 635                 640
Gln Val Trp Ile Asn Gly Gln Ser Leu Gly Arg His Trp Pro Ala Tyr
                645                 650                 655
Lys Ser Ser Gly Ser Cys Ser Val Cys Asn Tyr Thr Gly Trp Phe Asp
            660                 665                 670
Glu Lys Lys Cys Leu Thr Asn Cys Gly Glu Gly Ser Gln Arg Trp Tyr
        675                 680                 685
His Val Pro Arg Ser Trp Leu Tyr Pro Thr Gly Asn Leu Leu Val Val
    690                 695                 700
Phe Glu Glu Trp Gly Gly Asp Pro Tyr Gly Ile Thr Leu Val Lys Arg
705                 710                 715                 720
Glu Ile Gly Ser Val Cys Ala Asp Ile Tyr Glu Trp Gln Pro Gln Leu
                725                 730                 735
Leu Asn Trp Gln Arg Leu Val Ser Gly Lys Phe Asp Arg Pro Leu Arg
            740                 745                 750
Pro Lys Ala His Leu Lys Cys Ala Pro Gly Gln Lys Ile Ser Ser Ile
        755                 760                 765
```

-continued

```
Lys Phe Ala Ser Phe Gly Thr Pro Glu Gly Val Cys Gly Asn Phe Gln
    770                 775                 780

Gln Gly Ser Cys His Ala Pro Arg Ser Tyr Asp Ala Phe Lys Lys Asn
785                 790                 795                 800

Cys Val Gly Lys Glu Ser Cys Ser Val Gln Val Thr Pro Glu Asn Phe
                805                 810                 815

Gly Gly Asp Pro Cys Arg Asn Val Leu Lys Lys Leu Ser Val Glu Ala
            820                 825                 830

Ile Cys Ser
        835

<210> SEQ ID NO 9
<211> LENGTH: 887
<212> TYPE: PRT
<213> ORGANISM: Lycopersicon esculentum

<400> SEQUENCE: 9

Ser Arg Arg Lys Thr Leu Asn Phe Pro Leu Ile Leu Thr Val Leu Thr
  1               5                  10                  15

Ile His Phe Val Ile Val Ala Gly Glu Tyr Phe Lys Pro Phe Asn Val
                 20                  25                  30

Thr Tyr Asp Asn Arg Ala Leu Ile Ile Gly Gly Lys Arg Arg Met Leu
             35                  40                  45

Ile Ser Ala Gly Ile His Tyr Pro Arg Ala Thr Pro Glu Met Trp Pro
 50                  55                  60

Thr Leu Ile Ala Arg Ser Lys Glu Gly Gly Ala Asp Val Ile Glu Thr
 65                  70                  75                  80

Tyr Thr Phe Trp Asn Gly His Glu Pro Thr Arg Gly Gln Tyr Asn Phe
                 85                  90                  95

Glu Gly Arg Tyr Asp Ile Val Lys Phe Ala Lys Leu Val Gly Ser His
            100                 105                 110

Gly Leu Phe Leu Phe Ile Arg Ile Gly Pro Tyr Ala Cys Ala Glu Trp
        115                 120                 125

Asn Phe Gly Gly Phe Pro Ile Trp Leu Arg Asp Ile Pro Gly Ile Glu
130                 135                 140

Phe Arg Thr Asp Asn Ala Pro Phe Lys Glu Glu Met Glu Arg Tyr Val
145                 150                 155                 160

Lys Lys Ile Val Asp Leu Met Ile Ser Glu Ser Leu Phe Ser Trp Gln
                165                 170                 175

Gly Gly Pro Ile Ile Leu Leu Gln Ile Glu Asn Glu Tyr Gly Asn Val
            180                 185                 190

Glu Ser Ser Phe Gly Pro Lys Gly Lys Leu Tyr Met Lys Trp Ala Ala
        195                 200                 205

Glu Met Ala Val Gly Leu Gly Ala Gly Val Pro Trp Val Met Cys Arg
    210                 215                 220

Gln Thr Asp Ala Pro Glu Tyr Ile Ile Asp Thr Cys Asn Ala Tyr Tyr
225                 230                 235                 240

Cys Asp Gly Phe Thr Pro Asn Ser Glu Lys Lys Pro Lys Ile Trp Thr
                245                 250                 255

Glu Asn Trp Asn Gly Trp Phe Ala Asp Trp Gly Glu Arg Leu Pro Tyr
            260                 265                 270

Arg Pro Ser Glu Asp Ile Ala Phe Ala Ile Ala Arg Phe Phe Gln Arg
        275                 280                 285

Gly Gly Ser Leu Gln Asn Tyr Tyr Met Tyr Phe Gly Gly Thr Asn Phe
```

```
                290                 295                 300
Gly Arg Thr Ala Gly Pro Thr Gln Ile Thr Ser Tyr Asp Tyr Asp
305                 310                 315                 320

Ala Pro Leu Asp Glu Tyr Gly Leu Leu Arg Gln Pro Lys Trp Gly His
                325                 330                 335

Leu Lys Asp Leu His Ala Ala Ile Lys Leu Cys Glu Pro Ala Leu Val
                340                 345                 350

Ala Ala Asp Ser Pro Gln Tyr Ile Lys Leu Gly Pro Lys Gln Glu Ala
                355                 360                 365

His Val Tyr Arg Gly Thr Ser Asn Asn Ile Gly Gln Tyr Met Ser Leu
370                 375                 380

Asn Glu Gly Ile Cys Ala Ala Phe Ile Ala Asn Ile Asp Glu His Glu
385                 390                 395                 400

Ser Ala Thr Val Lys Phe Tyr Gly Gln Glu Phe Thr Leu Pro Pro Trp
                405                 410                 415

Ser Val Val Phe Cys Gln Ile Ala Glu Ile Gln Leu Ser Thr Gln Leu
                420                 425                 430

Arg Trp Gly His Lys Leu Gln Ser Lys Gln Trp Ala Gln Ile Leu Phe
                435                 440                 445

Gln Leu Gly Ile Ile Leu Cys Phe Tyr Lys Leu Ser Leu Lys Ala Ser
450                 455                 460

Ser Glu Ser Phe Ser Gln Ser Trp Met Thr Leu Lys Glu Pro Leu Gly
465                 470                 475                 480

Val Trp Gly Asp Lys Asn Phe Thr Ser Lys Gly Ile Leu Glu His Leu
                485                 490                 495

Asn Val Thr Lys Asp Gln Ser Asp Tyr Leu Trp Tyr Leu Thr Arg Ile
                500                 505                 510

Tyr Ile Ser Asp Asp Ile Ser Phe Trp Glu Glu Asn Asp Val Ser
                515                 520                 525

Pro Thr Ile Asp Ile Asp Ser Met Arg Asp Phe Val Arg Ile Phe Val
                530                 535                 540

Asn Gly Gln Leu Ala Gly Ser Val Lys Gly Lys Trp Ile Lys Val Val
545                 550                 555                 560

Gln Pro Val Lys Leu Val Gln Gly Tyr Asn Asp Ile Leu Leu Ser
                565                 570                 575

Glu Thr Val Gly Leu Gln Asn Tyr Gly Ala Phe Leu Glu Lys Asp Gly
                580                 585                 590

Ala Gly Phe Lys Gly Gln Ile Lys Leu Thr Gly Cys Lys Ser Gly Asp
                595                 600                 605

Ile Asn Leu Thr Thr Ser Leu Trp Thr Tyr Gln Val Gly Leu Arg Gly
                610                 615                 620

Glu Phe Leu Glu Val Tyr Asp Val Asn Ser Thr Glu Ser Ala Gly Trp
625                 630                 635                 640

Thr Glu Phe Pro Thr Gly Thr Thr Pro Ser Val Phe Ser Trp Tyr Lys
                645                 650                 655

Thr Lys Phe Asp Ala Pro Gly Gly Thr Asp Pro Val Ala Leu Asp Phe
                660                 665                 670

Ser Ser Met Gly Lys Gly Gln Ala Trp Val Asn Gly His His Val Gly
                675                 680                 685

Arg Tyr Trp Thr Leu Val Ala Pro Asn Asn Gly Cys Gly Arg Thr Cys
                690                 695                 700

Asp Tyr Arg Gly Ala Tyr His Ser Asp Lys Cys Arg Thr Asn Cys Gly
705                 710                 715                 720
```

-continued

```
Glu Ile Thr Gln Ala Trp Tyr His Ile Pro Arg Ser Trp Leu Lys Thr
                725                 730                 735
Leu Asn Asn Val Leu Val Ile Phe Glu Glu Thr Asp Lys Thr Pro Phe
            740                 745                 750
Asp Ile Ser Ile Ser Thr Arg Ser Thr Glu Thr Ile Cys Ala Gln Val
        755                 760                 765
Ser Glu Lys His Tyr Pro Pro Leu His Lys Trp Ser His Ser Glu Phe
    770                 775                 780
Asp Arg Lys Leu Ser Leu Met Asp Lys Thr Pro Glu Met His Leu Gln
785                 790                 795                 800
Cys Asp Glu Gly His Thr Ile Ser Ser Ile Glu Phe Ala Ser Tyr Gly
                805                 810                 815
Ser Pro Asn Gly Ser Cys Gln Lys Phe Ser Gln Gly Lys Cys His Ala
            820                 825                 830
Ala Asn Ser Leu Ser Val Val Ser Gln Ala Cys Ile Gly Arg Thr Ser
        835                 840                 845
Cys Ser Ile Gly Ile Ser Asn Gly Val Phe Gly Asp Pro Cys Arg His
    850                 855                 860
Val Val Lys Ser Leu Ala Val Gln Ala Lys Cys Ser Pro Pro Asp
865                 870                 875                 880
Leu Ser Thr Ser Ala Ser Ser
                885
```

<210> SEQ ID NO 10
<211> LENGTH: 838
<212> TYPE: PRT
<213> ORGANISM: Lycopersicon esculentum

<400> SEQUENCE: 10

```
Met Gly Cys Thr Leu Ile Leu Met Leu Asn Val Leu Val Leu Leu
  1               5                  10                  15
Gly Ser Trp Val Phe Ser Gly Thr Ala Ser Val Ser Tyr Asp His Arg
                 20                  25                  30
Ala Ile Ile Val Asn Gly Gln Arg Ile Leu Ile Ser Gly Ser Val
             35                  40                  45
His Tyr Pro Arg Ser Thr Pro Glu Met Trp Pro Gly Ile Ile Gln Lys
         50                  55                  60
Ala Lys Glu Gly Gly Val Asp Val Ile Gln Thr Tyr Val Phe Trp Asn
 65                  70                  75                  80
Gly His Glu Pro Gln Gln Gly Lys Tyr Tyr Phe Glu Gly Arg Tyr Asp
                 85                  90                  95
Leu Val Lys Phe Ile Lys Leu Val His Gln Ala Gly Leu Tyr Val His
                100                 105                 110
Leu Arg Val Gly Pro Tyr Ala Cys Ala Glu Trp Asn Phe Gly Gly Phe
            115                 120                 125
Pro Val Trp Leu Lys Tyr Val Pro Gly Ile Ser Phe Arg Thr Asp Asn
        130                 135                 140
Gly Pro Phe Lys Ala Ala Met Gln Lys Phe Thr Ala Lys Ile Val Asn
145                 150                 155                 160
Met Met Lys Ala Glu Arg Leu Tyr Glu Thr Gln Gly Gly Pro Ile Ile
                165                 170                 175
Leu Ser Gln Ile Glu Asn Glu Tyr Gly Pro Met Glu Trp Glu Leu Gly
            180                 185                 190
Ala Pro Gly Lys Ser Tyr Ala Gln Trp Ala Ala Lys Met Ala Val Gly
```

-continued

```
                195                 200                 205
Leu Asp Thr Gly Val Pro Trp Val Met Cys Lys Gln Asp Ala Pro
    210                 215                 220
Asp Pro Ile Ile Asn Ala Cys Asn Gly Phe Tyr Cys Asp Tyr Phe Ser
225                 230                 235                 240
Pro Asn Lys Ala Tyr Lys Pro Lys Ile Trp Thr Glu Ala Trp Thr Ala
                245                 250                 255
Trp Phe Thr Gly Phe Gly Asn Pro Val Pro Tyr Arg Pro Ala Glu Asp
                260                 265                 270
Leu Ala Phe Ser Val Ala Lys Phe Ile Gln Lys Gly Gly Ser Phe Ile
                275                 280                 285
Asn Tyr Tyr Met Tyr His Gly Gly Thr Asn Phe Gly Arg Thr Ala Gly
    290                 295                 300
Gly Pro Phe Ile Ala Thr Ser Tyr Asp Tyr Asp Ala Pro Leu Asp Glu
305                 310                 315                 320
Tyr Gly Leu Leu Arg Gln Pro Lys Trp Gly His Leu Lys Asp Leu His
                325                 330                 335
Arg Ala Ile Lys Leu Cys Glu Pro Ala Leu Val Ser Gly Asp Pro Ala
                340                 345                 350
Val Thr Ala Leu Gly His Gln Gln Glu Ala His Val Phe Arg Ser Lys
                355                 360                 365
Ala Gly Ser Cys Ala Ala Phe Leu Ala Asn Tyr Asp Gln His Ser Phe
    370                 375                 380
Ala Thr Val Ser Phe Ala Asn Arg His Tyr Asn Leu Pro Pro Trp Ser
385                 390                 395                 400
Ile Ser Ile Leu Pro Asp Cys Lys Asn Thr Val Phe Asn Thr Ala Arg
                405                 410                 415
Ile Gly Ala Gln Ser Ala Gln Met Lys Met Thr Pro Val Ser Arg Gly
                420                 425                 430
Leu Pro Trp Gln Ser Phe Asn Glu Glu Thr Ser Ser Tyr Glu Asp Ser
                435                 440                 445
Ser Phe Thr Val Val Gly Leu Leu Glu Gln Ile Asn Thr Thr Arg Asp
    450                 455                 460
Val Ser Asp Tyr Leu Trp Tyr Ser Thr Asp Val Lys Ile Asp Ser Arg
465                 470                 475                 480
Glu Lys Phe Leu Arg Gly Gly Lys Trp Pro Trp Leu Thr Ile Met Ser
                485                 490                 495
Ala Gly His Ala Leu His Val Phe Val Asn Gly Gln Leu Ala Gly Thr
                500                 505                 510
Ala Tyr Gly Ser Leu Glu Lys Pro Lys Leu Thr Phe Ser Lys Ala Val
                515                 520                 525
Asn Leu Arg Ala Gly Val Asn Lys Ile Ser Leu Leu Ser Ile Ala Val
    530                 535                 540
Gly Leu Pro Asn Ile Gly Pro His Phe Glu Thr Trp Asn Ala Gly Val
545                 550                 555                 560
Leu Gly Pro Val Ser Leu Thr Gly Leu Asp Glu Gly Lys Arg Asp Leu
                565                 570                 575
Thr Trp Gln Lys Trp Ser Tyr Lys Val Gly Leu Lys Gly Glu Ala Leu
                580                 585                 590
Ser Leu His Ser Leu Ser Gly Ser Ser Val Glu Trp Val Glu Gly
                595                 600                 605
Ser Leu Val Ala Gln Arg Gln Pro Leu Thr Trp Tyr Lys Ser Thr Phe
    610                 615                 620
```

```
Asn Ala Pro Ala Gly Asn Asp Pro Leu Ala Leu Asp Leu Asn Thr Met
625                 630                 635                 640

Gly Lys Gly Gln Val Trp Ile Asn Gly Gln Ser Leu Gly Arg Tyr Trp
            645                 650                 655

Pro Gly Tyr Lys Ala Ser Gly Asn Cys Gly Ala Cys Asn Tyr Ala Gly
            660                 665                 670

Trp Phe Asn Glu Lys Lys Cys Leu Ser Asn Cys Gly Glu Ala Ser Gln
        675                 680                 685

Arg Trp Tyr His Val Pro Arg Ser Trp Leu Tyr Pro Thr Gly Asn Leu
    690                 695                 700

Leu Val Leu Phe Glu Glu Trp Gly Gly Glu Pro His Gly Ile Ser Leu
705                 710                 715                 720

Val Lys Arg Glu Val Ala Ser Val Cys Ala Asp Ile Asn Glu Trp Gln
                725                 730                 735

Pro Gln Leu Val Asn Trp Gln Met Gln Ala Ser Gly Lys Val Asp Lys
            740                 745                 750

Pro Leu Arg Pro Lys Ala His Leu Ser Cys Ala Ser Gly Gln Lys Ile
        755                 760                 765

Thr Ser Ile Lys Phe Ala Ser Phe Gly Thr Pro Gln Gly Val Cys Gly
    770                 775                 780

Ser Phe Arg Glu Gly Ser Cys His Ala Phe His Ser Tyr Asp Ala Phe
785                 790                 795                 800

Glu Arg Tyr Cys Ile Gly Gln Asn Ser Cys Ser Val Pro Val Thr Pro
                805                 810                 815

Glu Ile Phe Gly Gly Asp Pro Cys Pro His Val Met Lys Lys Leu Ser
            820                 825                 830

Val Glu Val Ile Cys Ser
        835

<210> SEQ ID NO 11
<211> LENGTH: 724
<212> TYPE: PRT
<213> ORGANISM: Lycopersicon esculentum

<400> SEQUENCE: 11

Met Leu Arg Thr Asn Val Leu Leu Leu Val Ile Cys Leu Leu Asp
 1               5                  10                  15

Phe Phe Ser Ser Val Lys Ala Ser Val Ser Tyr Asp Asp Arg Ala Ile
            20                  25                  30

Ile Ile Asn Gly Lys Arg Lys Ile Leu Ile Ser Gly Ser Ile His Tyr
        35                  40                  45

Pro Arg Ser Thr Pro Gln Met Trp Pro Asp Leu Ile Gln Lys Ala Lys
    50                  55                  60

Asp Gly Gly Leu Asp Val Ile Glu Thr Tyr Val Phe Trp Asn Gly His
65                  70                  75                  80

Glu Pro Ser Pro Gly Lys Tyr Asn Phe Glu Gly Arg Tyr Asp Leu Val
                85                  90                  95

Arg Phe Ile Lys Met Val Gln Arg Ala Gly Leu Tyr Val Asn Leu Arg
            100                 105                 110

Ile Gly Pro Tyr Val Cys Ala Glu Trp Asn Phe Gly Gly Phe Pro Val
        115                 120                 125

Trp Leu Lys Tyr Val Pro Gly Met Glu Phe Arg Thr Asn Asn Gln Pro
    130                 135                 140

Phe Lys Val Ala Met Gln Gly Phe Val Gln Lys Ile Val Asn Met Met
```

```
          145                 150                 155                 160
Lys Ser Glu Asn Leu Phe Glu Ser Gln Gly Gly Pro Ile Ile Met Ala
                165                 170                 175
Gln Ile Glu Asn Glu Tyr Gly Pro Val Glu Trp Glu Ile Gly Ala Pro
                180                 185                 190
Gly Lys Ala Tyr Thr Lys Trp Ala Ala Gln Met Ala Val Gly Leu Lys
                195                 200                 205
Thr Gly Val Pro Trp Ile Met Cys Lys Gln Glu Asp Ala Pro Asp Pro
        210                 215                 220
Val Ile Asp Thr Cys Asn Gly Phe Tyr Cys Glu Gly Phe Arg Pro Asn
225                 230                 235                 240
Lys Pro Tyr Lys Pro Lys Met Trp Thr Glu Val Trp Thr Gly Trp Tyr
                245                 250                 255
Thr Lys Phe Gly Gly Pro Ile Pro Gln Arg Pro Ala Glu Asp Ile Ala
                260                 265                 270
Phe Ser Val Ala Arg Phe Val Gln Asn Asn Gly Ser Phe Phe Asn Tyr
            275                 280                 285
Tyr Met Tyr His Gly Gly Thr Asn Phe Gly Arg Thr Ser Ser Gly Leu
        290                 295                 300
Phe Ile Ala Thr Ser Tyr Asp Tyr Asp Ala Pro Leu Asp Glu Tyr Gly
305                 310                 315                 320
Leu Leu Asn Glu Pro Lys Tyr Gly His Leu Arg Asp Leu His Lys Ala
                325                 330                 335
Ile Lys Leu Ser Glu Pro Ala Leu Val Ser Ser Tyr Ala Ala Val Thr
                340                 345                 350
Ser Leu Gly Ser Asn Gln Glu Ala His Val Tyr Arg Ser Lys Ser Gly
            355                 360                 365
Ala Cys Ala Ala Phe Leu Ser Asn Tyr Asp Ser Arg Tyr Ser Val Lys
        370                 375                 380
Val Thr Phe Gln Asn Arg Pro Tyr Asn Leu Pro Pro Trp Ser Ile Ser
385                 390                 395                 400
Ile Leu Pro Asp Cys Lys Thr Ala Val Tyr Asn Thr Ala Gln Val Asn
                405                 410                 415
Ser Gln Ser Ser Ser Ile Lys Met Thr Pro Ala Gly Gly Leu Ser
            420                 425                 430
Trp Gln Ser Tyr Asn Glu Glu Thr Pro Thr Ala Asp Asp Ser Asp Thr
        435                 440                 445
Leu Thr Ala Asn Gly Leu Trp Glu Gln Lys Asn Val Thr Arg Asp Ser
    450                 455                 460
Ser Asp Tyr Leu Trp Tyr Met Thr Asn Val Asn Ile Ala Ser Asn Glu
465                 470                 475                 480
Gly Phe Leu Lys Asn Gly Lys Asp Pro Tyr Leu Thr Val Met Ser Ala
                485                 490                 495
Gly His Val Leu His Val Phe Val Asn Gly Lys Leu Ser Gly Thr Val
            500                 505                 510
Tyr Gly Thr Leu Asp Asn Pro Lys Leu Thr Tyr Ser Gly Asn Val Lys
        515                 520                 525
Leu Arg Ala Gly Ile Asn Lys Ile Ser Leu Leu Ser Val Ser Val Gly
    530                 535                 540
Leu Pro Asn Val Gly Val His Tyr Asp Thr Trp Asn Ala Gly Val Leu
545                 550                 555                 560
Gly Pro Val Thr Leu Ser Gly Leu Asn Glu Gly Ser Arg Asn Leu Ala
                565                 570                 575
```

```
Lys Gln Lys Trp Ser Tyr Lys Val Gly Leu Lys Gly Glu Ser Leu Ser
            580                 585                 590

Leu His Ser Leu Ser Gly Ser Ser Val Glu Trp Val Arg Gly Ser
            595                 600                 605

Leu Met Ala Gln Lys Gln Pro Leu Thr Trp Tyr Lys Ala Thr Phe Asn
            610                 615                 620

Ala Pro Gly Gly Asn Asp Pro Leu Ala Leu Asp Met Ala Ser Met Gly
625                 630                 635                 640

Lys Gly Gln Ile Trp Ile Asn Gly Glu Gly Val Gly Arg His Trp Pro
                645                 650                 655

Gly Tyr Ile Ala Gln Gly Asp Cys Ser Lys Cys Ser Tyr Ala Gly Thr
            660                 665                 670

Phe Asn Glu Lys Lys Cys Gln Thr Asn Cys Gly Gln Pro Ser Gln Arg
            675                 680                 685

Trp Tyr His Val Pro Arg Ser Trp Leu Lys Pro Ser Gly Asn Leu Leu
            690                 695                 700

Val Val Phe Glu Glu Trp Gly Gly Asn Pro Thr Gly Ile Ser Leu Val
705                 710                 715                 720

Arg Arg Ser Arg

<210> SEQ ID NO 12
<211> LENGTH: 251
<212> TYPE: PRT
<213> ORGANISM: Lycopersicon esculentum

<400> SEQUENCE: 12

Ile Gln Thr Tyr Val Phe Trp Asn Leu His Glu Pro Val Arg Asn Gln
1               5                   10                  15

Tyr Asp Phe Glu Gly Arg Lys Asp Leu Ile Asn Phe Val Lys Leu Val
            20                  25                  30

Glu Arg Ala Gly Leu Phe Val His Ile Arg Ile Gly Pro Tyr Val Cys
        35                  40                  45

Ala Glu Trp Asn Tyr Gly Gly Phe Pro Leu Trp Leu His Phe Ile Pro
    50                  55                  60

Gly Ile Glu Phe Arg Thr Asp Asn Glu Pro Phe Lys Ala Glu Met Lys
65                  70                  75                  80

Arg Phe Thr Ala Lys Ile Val Asp Met Ile Lys Gln Glu Asn Leu Tyr
                85                  90                  95

Ala Ser Gln Gly Gly Pro Val Ile Leu Ser Gln Ile Glu Asn Glu Tyr
            100                 105                 110

Gly Asn Gly Asp Ile Glu Ser Arg Tyr Gly Pro Arg Ala Lys Pro Tyr
        115                 120                 125

Val Asn Trp Ala Ala Ser Met Ala Thr Ser Leu Asn Thr Gly Val Pro
130                 135                 140

Trp Val Met Cys Gln Gln Pro Asp Ala Pro Ser Val Ile Asn Thr
145                 150                 155                 160

Cys Asn Gly Phe Tyr Cys Asp Gln Phe Lys Gln Asn Ser Asp Lys Thr
                165                 170                 175

Pro Lys Met Trp Thr Glu Asn Trp Thr Gly Trp Phe Leu Ser Phe Gly
            180                 185                 190

Gly Phe Val Pro Tyr Arg Pro Val Glu Asp Ile Ala Phe Ala Val Ala
        195                 200                 205

Arg Phe Phe Gln Arg Gly Gly Thr Phe Gln Asn Tyr Tyr Met Tyr His
210                 215                 220
```

```
Gly Gly Thr Asn Phe Gly Arg Thr Ser Gly Gly Pro Phe Ile Ala Thr
225                 230                 235                 240

Ser Tyr Asp Tyr Asp Ala Pro Leu Asp Glu Tyr
            245                 250

<210> SEQ ID NO 13
<211> LENGTH: 249
<212> TYPE: PRT
<213> ORGANISM: Lycopersicon esculentum

<400> SEQUENCE: 13

Ile Gln Thr Tyr Val Phe Trp Asn Val His Glu Pro Ser Pro Gly Asn
 1               5                  10                  15

Tyr Asn Phe Glu Gly Arg Tyr Asp Leu Val Arg Phe Val Lys Thr Ile
                20                  25                  30

Gln Lys Ala Gly Leu Tyr Ala His Leu Arg Ile Gly Pro Tyr Val Cys
            35                  40                  45

Ala Glu Trp Asn Phe Gly Gly Phe Pro Val Trp Leu Lys Tyr Val Pro
        50                  55                  60

Gly Ile Ser Phe Arg Ala Asp Asn Glu Pro Phe Lys Asn Ala Met Lys
 65                 70                  75                  80

Gly Tyr Ala Glu Lys Ile Val Asn Leu Met Lys Ile Ile Phe Ser
                85                  90                  95

Ser Leu Arg Val Val Gln Ser Tyr Ser His Arg Leu Arg Met Ser Met
                100                 105                 110

Gly Leu Lys Pro Arg Tyr Leu Glu His Arg Asp Ile Ser Ile Gln His
            115                 120                 125

Gly Leu Gln Ile Trp Gln Leu Asp Leu Asn Thr Gly Val Pro Trp Val
        130                 135                 140

Met Cys Lys Glu Glu Asp Ala Pro Asp Pro Val Ile Asn Thr Cys Asn
145                 150                 155                 160

Gly Phe Tyr Cys Asp Asn Phe Phe Pro Asn Lys Pro Tyr Lys Pro Ala
                165                 170                 175

Ile Trp Thr Glu Ala Trp Ser Gly Trp Phe Ser Glu Phe Gly Gly Pro
                180                 185                 190

Leu His Gln Arg Pro Val Gln Asp Leu Ala Phe Ala Val Ala Gln Phe
            195                 200                 205

Ile Gln Arg Gly Gly Ser Phe Val Asn Tyr Tyr Met Tyr His Gly Gly
        210                 215                 220

Thr Asn Phe Gly Arg Thr Ala Gly Gly Pro Phe Ile Thr Thr Ser Tyr
225                 230                 235                 240

Asp Tyr Asp Ala Pro Leu Asp Glu Tyr
                245

<210> SEQ ID NO 14
<211> LENGTH: 870
<212> TYPE: PRT
<213> ORGANISM: Lycopersicon esculentum

<400> SEQUENCE: 14

Met Asn Thr Met Ser Cys Leu Ser Ser Asn Phe Lys Phe Val Phe Leu
 1               5                  10                  15

Ala Ser Thr Val Ile Trp Met Thr Val Met Ser Ser Ser Leu Ala Ala
                20                  25                  30

Val Asp Ala Ser Asn Val Thr Thr Ile Gly Thr Asp Ser Val Thr Tyr
            35                  40                  45
```

```
Asp Arg Arg Ser Leu Ile Ile Asn Gly Gln Arg Lys Leu Leu Ile Ser
         50                  55                  60

Ala Ser Ile His Tyr Pro Arg Ser Val Pro Ala Met Trp Pro Gly Leu
 65                  70                  75                  80

Val Arg Leu Ala Lys Glu Gly Val Asp Val Ile Glu Thr Tyr Val
                 85                  90                  95

Phe Trp Asn Gly His Glu Pro Ser Pro Gly Asn Tyr Tyr Phe Gly Gly
             100                 105                 110

Arg Phe Asp Leu Val Lys Phe Cys Lys Ile Ile Gln Gln Ala Gly Met
             115                 120                 125

Tyr Met Ile Leu Arg Ile Gly Pro Phe Val Ala Ala Glu Trp Asn Phe
     130                 135                 140

Gly Gly Leu Pro Val Trp Leu His Tyr Val Pro Gly Thr Thr Phe Arg
145                 150                 155                 160

Thr Asp Ser Glu Pro Phe Lys Tyr His Met Gln Lys Phe Met Thr Tyr
                 165                 170                 175

Thr Val Asn Leu Met Lys Arg Glu Arg Leu Phe Ala Ser Gln Gly Gly
             180                 185                 190

Pro Ile Ile Leu Ser Gln Val Glu Asn Glu Tyr Gly Tyr Tyr Glu Asn
         195                 200                 205

Ala Tyr Gly Glu Gly Gly Lys Arg Tyr Ala Leu Trp Ala Ala Lys Met
     210                 215                 220

Ala Leu Ser Gln Asn Thr Gly Val Pro Trp Ile Met Cys Gln Gln Tyr
225                 230                 235                 240

Asp Ala Pro Asp Pro Val Ile Asp Thr Cys Asn Ser Phe Tyr Cys Asp
                 245                 250                 255

Gln Phe Lys Pro Ile Ser Pro Asn Lys Pro Lys Ile Trp Thr Glu Asn
             260                 265                 270

Trp Pro Gly Trp Phe Lys Thr Phe Gly Ala Arg Asp Pro His Arg Pro
     275                 280                 285

Ala Glu Asp Val Ala Tyr Ser Val Ala Arg Phe Phe Gln Lys Gly Gly
     290                 295                 300

Ser Val Gln Asn Tyr Tyr Met Tyr His Gly Gly Thr Asn Phe Gly Arg
305                 310                 315                 320

Thr Ala Gly Gly Pro Phe Ile Thr Thr Ser Tyr Asp Tyr Asp Ala Pro
                 325                 330                 335

Ile Asp Glu Tyr Gly Leu Pro Arg Phe Pro Lys Trp Gly His Leu Lys
             340                 345                 350

Glu Leu His Lys Val Ile Lys Ser Cys Glu His Ala Leu Leu Asn Asn
     355                 360                 365

Asp Pro Thr Leu Leu Ser Leu Gly Pro Leu Gln Glu Ala Asp Val Tyr
     370                 375                 380

Glu Asp Ala Ser Gly Ala Cys Ala Ala Phe Leu Ala Asn Met Asp Asp
385                 390                 395                 400

Lys Asn Asp Lys Val Val Gln Phe Arg His Val Ser Tyr His Leu Pro
                 405                 410                 415

Ala Trp Ser Val Ser Ile Leu Pro Asp Cys Lys Asn Val Ala Phe Asn
             420                 425                 430

Thr Ala Lys Val Gly Cys Gln Thr Ser Ile Val Asn Met Ala Pro Ile
     435                 440                 445

Asp Leu His Pro Thr Ala Ser Ser Pro Lys Arg Asp Ile Lys Ser Leu
     450                 455                 460
```

```
Gln Trp Glu Val Phe Lys Glu Thr Ala Gly Val Trp Gly Val Ala Asp
465                 470                 475                 480

Phe Thr Lys Asn Gly Phe Val Asp His Ile Asn Thr Lys Asp Ala
            485                 490                 495

Thr Asp Tyr Leu Trp Tyr Thr Thr Ser Ile Phe Val His Ala Glu Glu
                500                 505                 510

Asp Phe Leu Arg Asn Arg Gly Thr Ala Met Leu Phe Val Glu Ser Lys
                515                 520                 525

Gly His Ala Met His Val Phe Ile Asn Lys Lys Leu Gln Ala Ser Ala
        530                 535                 540

Ser Gly Asn Gly Thr Val Pro Gln Phe Lys Phe Gly Thr Pro Ile Ala
545                 550                 555                 560

Leu Lys Ala Gly Lys Asn Glu Ile Ser Leu Leu Ser Met Thr Val Gly
                565                 570                 575

Leu Gln Thr Ala Gly Ala Phe Tyr Glu Trp Ile Gly Ala Gly Pro Thr
            580                 585                 590

Ser Val Lys Val Ala Gly Phe Lys Thr Gly Thr Met Asp Leu Thr Ala
        595                 600                 605

Ser Ala Trp Thr Tyr Lys Ile Gly Leu Gln Gly Glu His Leu Arg Ile
610                 615                 620

Gln Lys Ser Tyr Asn Leu Lys Ser Lys Ile Trp Ala Pro Thr Ser Gln
625                 630                 635                 640

Pro Pro Lys Gln Gln Pro Leu Thr Trp Tyr Lys Ala Val Val Asp Ala
                645                 650                 655

Pro Pro Gly Asn Glu Pro Val Ala Leu Asp Met Ile His Met Gly Lys
                660                 665                 670

Gly Met Ala Trp Leu Asn Gly Gln Glu Ile Gly Arg Tyr Trp Pro Arg
        675                 680                 685

Arg Thr Ser Lys Tyr Glu Asn Cys Val Thr Gln Cys Asp Tyr Arg Gly
    690                 695                 700

Lys Phe Asn Pro Asp Lys Cys Val Thr Gly Cys Gly Gln Pro Thr Gln
705                 710                 715                 720

Arg Trp Tyr His Val Pro Arg Ser Trp Phe Lys Pro Ser Gly Asn Val
                725                 730                 735

Leu Ile Ile Phe Glu Glu Ile Gly Gly Asp Pro Ser Gln Ile Arg Phe
                740                 745                 750

Ser Met Arg Lys Val Ser Gly Ala Cys Gly His Leu Ser Val Asp His
        755                 760                 765

Pro Ser Phe Asp Val Glu Asn Leu Gln Gly Ser Glu Ile Glu Asn Asp
770                 775                 780

Lys Asn Arg Pro Thr Leu Ser Leu Lys Cys Pro Thr Asn Thr Asn Ile
785                 790                 795                 800

Ser Ser Val Lys Phe Ala Ser Phe Gly Asn Pro Asn Gly Thr Cys Gly
                805                 810                 815

Ser Tyr Met Leu Gly Asp Cys His Asp Gln Asn Ser Ala Ala Leu Val
            820                 825                 830

Glu Lys Val Cys Leu Asn Gln Asn Glu Cys Ala Leu Glu Met Ser Ser
        835                 840                 845

Ala Asn Phe Asn Met Gln Leu Cys Pro Ser Thr Val Lys Lys Leu Ala
850                 855                 860

Val Glu Val Asn Cys Ser
865                 870
```

What we claim is:

1. An isolated nucleic acid molecule comprising a polynucleotide having at least 95% sequence identity to a sequence selected from the group consisting of:
   (a) a nucleotide sequence encoding the tomato β-galactosidase II polypeptide having the complete amino acid sequence of SEQ ID NO: 11 and designated TBG4;
   (b) a nucleotide sequence encoding the mature tomato β-galactosidase II polypeptide, wherein said mature polypeptide is produced by cleavage of the leader sequence from the complete polypeptide having the complete amino acid sequence of SEQ ID NO:11; and
   (c) a nucleotide sequence fully complementary to either of the nucleotide sequences in (a) or (b), above, wherein said nucleotide sequence having at least 95% sequence identity encodes a polypeptide having β-galactosidase II activity.

2. The nucleic acid molecule of claim 1 wherein said polynucleotide has the complete nucleotide sequence of SEQ ID NO: 4.

3. The nucleic acid molecule of claim 1 wherein said polynucleotide contains the fragment of SEQ ID NO:4 which encodes the complete β-galactosidase II polypeptide having the amino acid sequence designated TBG4.

4. The nucleic acid molecule of claim 1 wherein said polynucleotide contains a fragment of SEQ ID NO:4 which encodes a mature polypeptide, wherein said mature polypeptide is produced by cleavage of the leader sequence from the complete polypeptide.

5. An isolated nucleic acid molecule comprising a polynucleotide which hybridizes under stringent hybridization conditions to a polynucleotide having a nucleotide sequence identical to the nucleotide sequence in (a), (b), or (c) of claim 1, wherein said polynucleotide which hybridizes does not hybridize under stringent hybridization conditions to a polynucleotide having a nucleotide sequence consisting of only A residues or of only T residues, wherein stringent hybridization conditions are overnight incubation at 42° C. in a solution comprising 50% formamide, 5×SSC (150 mM NaCl, 15 mM trisodium citrate), 50 mM sodium phosphate (pH 7.6), 5×Denhardt's solution, 10% dextran sulfate and 20 μg/ml denatured, sheared salmon sperm DNA, followed by washing in 0.1×SSC at about 65° C., and wherein said polynucleotide has a nucleotide sequence which encodes a polypeptide having β-galactosidase activity.

6. A method for making a recombinant vector comprising inserting the isolated nucleic acid molecule of claim 1 into a vector.

7. A recombinant vector produced by the method of claim 6.

8. A method of making a recombinant host cell comprising introducing the recombinant vector of claim 7 into a host cell.

9. A recombinant host cell produced by the method of claim 8.

10. A recombinant method for producing a β-galactosidase II polypeptide, comprising culturing the recombinant host cell of claim 9 under conditions such that said polypeptide is expressed and recovering said polypeptide.

* * * * *